US006537803B1

(12) United States Patent
Amara et al.

(10) Patent No.: US 6,537,803 B1
(45) Date of Patent: *Mar. 25, 2003

(54) AMINO ACID TRANSPORTERS AND USES

(75) Inventors: Susan G. Amara; Jeffrey L. Arriza, both of Portland, OR (US)

(73) Assignee: Oregon Health Sciences University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/227,614

(22) Filed: Jan. 8, 1999

Related U.S. Application Data

(62) Division of application No. 09/042,929, filed on Mar. 17, 1998, which is a division of application No. 08/546,666, filed on Oct. 23, 1995, now Pat. No. 5,776,774, which is a division of application No. 08/140,729, filed on Oct. 20, 1993, now Pat. No. 5,658,782.

(51) Int. Cl.[7] ......................... C12N 1/00; C12N 15/00; C12N 5/00; C12N 1/20
(52) U.S. Cl. ................ 435/317.1; 435/69.1; 435/320.1; 435/455; 435/471; 435/252.3; 435/325; 530/350
(58) Field of Search ........................... 435/317.1, 69.1, 435/320.1, 455, 471, 252.3, 325; 530/350

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 5,385,831 A | 1/1995 | Mulvihill et al. | 435/69.1 |
| 5,424,185 A | 6/1995 | Lam et al. | 435/6 |

OTHER PUBLICATIONS

Arriza et al. (1994) J. Neurosci., vol. 14, No. 9, pp. 5559–5569.
Kanai et al. (1992) Nature, 360:467–471.
Kanai et al. (1993) Trends in Neurosci., vol. 16, No. 9, pp. 365–370.
Kanai et al., (1993) FASEB J., 7: 1450–1459.
Kanner, (1993), FEBS Lett., 325 (1,2): pp. 95–99.
Pines et al., (1992) Nature, 360: pp. 464–467.
Schloss et al. (1992) FEBS Lett., 307 (1): pp. 76–80.
Shashidharan et al., (1993), Biochim. Biophys. Acta., 1216: pp. 161–164.
Stelzner et al., (1993) FASEB J., 7(4/part 2): A575.
Storck et al., (1992), Proc. Natl. Acad. Sci., 89: pp. 10955–10959.
Uhl, (1992), Trends in Neurosci., 15(7): 265–268.
Anderson et al., (1989) J. Biol. Chem., 264: pp. 8222–822.
Arriza et al., (1992) J. Neurosci., 12:4045–4055.
Barish, (1983) J. Physiol., 342: 309–325.
Bertling et al., (1987) Bioscience Reports, 7: 107–112.
Blakely et al., (1991) Anal. Biochem., 194: 302–308.
Bouvier et al., (1992) Nature, 360: 471–474.
Bussolati et al., (1992) J. Biol. Chem., 267:8330–8335.
Choi et al., (1987) Neurosci., 7:357–358.
Chomczynski & Sacchi, (1987) Anal. Biochem., 162: 156–159.
Christensen (1990), Physiol. Rev., 70:43:77.
Christensen et al., (1967). J. Biol. Chem., 242:5237–5246.
Eisenberg et al., (1984), J. Molec. Biol., 179: 125–142.
Engelke et al., (1992) J. Bacteriol., 171:5551–5560.
Fairman, (1995) Human Excitatory Amino Acid Transporter 4, Genbank Accession Number U18244.
Felgner et al., (1987) Proc. Natl. Acad. Sci., 84: 7412–7417.
Gesogiou, (1988) AICHE Journal, vol. 34, No. 8, pp. 1233–1248.
Gluzman, (1981) Cell, 23: 175–182.
Guastella et al., (1992) Proc. Natl. Sci., 89: 7189–7193.
Guastella et al., (1990) Science, 249: 1303–1306.
Kanai et al., (1994) J. Biol. Chem., vol. 269, No. 32, pp. 20599–20606.
Kanner & Schuldiner, (1987), CRC Crit. Rev. Biochem., 22: 1–38.
Kavanaugh et al., (1992) J. Biol. Chem., 267: 22007–22009.
Kim et al., (1991) Nature, 352: 725–728.
Kong et al., (1993) J. Biol. Chem., 268: 1509–1512.
Kozak, (1987) Nucleic Acid Res., 15: 8125–8132.
Maenz et al., (1992), J. Biol. Chem., 267: 1510–1516.
Makowske & Christensen, (1982) J. Biol. Chem., 257: 14635–14638.
Nicholls & Atwell, (1990), TIPS, 11:462–468.
Olney et al., (1990) Science, 248: 596–599.
Quick and Lester, (1994) Methods in Neuroscience, 19: 261–279.
Saiki et al., (1988) Science, 239: 487–491.
Sanger et al., (1977) Proc. Natl. Acad. Sci., 74:5463.
Smith & Johnson, (1988) Gene, 67: 31–40.
Smithies et al., (1985) Nature, 317: 230–234.
Thomas & Capecchi, (1987) Cell, 51: 503–512.
Wallace et al., (1990) J. Bacteriol., 172: 3214–3220.
Wang et al., (1991) Nature, 352: 729–731.
Dreyer et al., (1996) Arch. Ophtalmol., 114: 299–305.
Honda, (1996) Nippon Ganka Gakkst Zasshi, 100:937–955.
Kalloniatis, (1995) J. Amer. Optom. Assoc., 66: 750–757.
Zerangue et al., (1995) J. Biol. Chem., 270: 6433–6435.
Kataoka et al., (1997) J. Neurosci., 17: 7017–7024.
Sheng et al., (1996) Neuron., 17:575–578.

Primary Examiner—Lisa J. Hobbs
(74) Attorney, Agent, or Firm—McDonnell Boehnen Hulbert & Berghoff

(57) ABSTRACT

The present invention relates to novel mammalian amino acid transporter proteins and the genes that encode such proteins. The invention is directed toward the isolation, characterization and pharmacological use of the human amino acid transporter proteins EAAT1, EAAT2, EAAT3 and ASCT1. The invention specifically provides isolated complementary DNA copies of mRNA corresponding to each of these transporter genes. Also provided are recombinant expression constructs capable of expressing each of the amino acid transporter genes of the invention in cultures of transformed prokaryotic and eukaryotic cells, as well as such cultures of transformed cells that synthesize the human amino acid transporter proteins encoded therein. The invention also provides methods for screening in vitro compounds having transport-modulating properties using preparations of transporter proteins from such cultures of cells transformed with recombinant expression constructs.

4 Claims, 42 Drawing Sheets

FIG. 1A

```
CACCTCTAGC TCGGAGCGGC GTGTAGCGCC                                                                          54

GGC TAC CTT GAC AGC GCT CAG GCG ATG GAG AAG AGC AAC GAG ACC AAC                                          102
Gly Tyr Leu Asp Ser Ala Gln Ala Met Glu Lys Ser Asn Glu Thr Asn
        10              15           1               5

CCG GGG ACC GCA GCG GGA CGC CCT GCG GGG GCC CCC GGA GCT                                                  150
Pro Gly Thr Ala Ala Gly Arg Pro Ala Gly Ala Pro Gly Ala
 25              30              35              40

CGC CAA GCG CTG GTG CTC ACC TCC CGT TGC CGG TTC CTG CGG                                                  198
Arg Gln Ala Leu Val Leu Thr Ser Arg Cys Arg Phe Leu Arg
             45              50              55

GGC CTG GGC GCG GCA GGG CTC AGC CTG GGG GCG GCG GCG GCG                                                  246
Gly Leu Gly Ala Ala Gly Leu Ser Leu Gly Ala Ala Ala Ala
     60              65              70

ACC TAC CTG GCC TTC CCC GGC GAG ATG CGC CTC CTG CAG GTC ATG                                              294
Thr Tyr Leu Ala Phe Pro Gly Glu Met Arg Leu Leu Gln Val Met
     75              80              85

ATC ATC CCG CTG GTC GTG AGC TGC CTG GGC GCC GCG TCG                                                      342
Ile Ile Pro Leu Val Val Ser Cys Leu Gly Ala Ala Ser
     90  Bval  95             100
```

FIG. 1B

```
CTC GAT GCC AGC TGC CTC GGG CGT CTG GGC GGC ATC CGT GTC GCC TAC    390
Leu Asp Ala Ser Cys Leu Gly Arg Leu Gly Gly Ile Arg Val Ala Tyr
105                 110                 115                 120

TTT GGC CTC ACC ACA CTG AGT GCC TCG GCG GCC CTC ATC GTG TTG GCG    438
Phe Gly Leu Thr Thr Leu Ser Ala Ser Ala Ala Leu Ile Val Leu Ala
                125                 130                 135

TTC ATC AAG CCA GGA TCC GGT GCG CAG ACC CTT TCC AGC GAC             486
Phe Ile Lys Pro Gly Ser Gly Ala Gln Thr Leu Ser Ser Asp
                140                 145                 150

CTG CTG GAG GAC TCG GGG CCT CCT GTC CTT TTT CCC AAA GTC GAG GTG    534
Leu Leu Glu Asp Ser Gly Pro Pro Val Leu Phe Pro Lys Val Glu Val
155                 160                 165

GAC TCT GAG CTC CTC AGA AAC GCA CTG TAT TAT CCC AAT CTT ACG GTG    582
Asp Ser Glu Leu Leu Arg Asn Ala Leu Tyr Tyr Pro Asn Leu Thr Val
            170                 175                 180

GTT GCT TTC CAT CGT ACG GCA ACC GAT TAT AAG CCC TCC ACC ACG CAG    630
Val Ala Phe His Arg Thr Ala Thr Asp Tyr Lys Pro Ser Thr Thr Gln
185                 190                 195                 200

AAC AGC TCT GGA AAT CGT GAA ATC AAG CCC GTG CAT ACC ATA GGC ACT    678
Asn Ser Ser Gly Asn Arg Glu Ile Lys Pro Val His Thr Ile Gly Thr
                205                 210                 215
```

*FIG. 1C*

| | | | | | | | | | | | | | | | | |
|---|---|---|---|---|---|---|---|---|---|---|---|---|---|---|---|---|
| GAG Glu | ATA Ile | GAA Glu | GGG Gly 220 | ATG Met | AAC Asn | ATT Ile | TTA Leu | GGA Gly 225 | TTG Leu | GTC Val | CTG Leu | TTT Phe | GCT Ala 230 | CTG Leu | GTG Val | 726 |
| TTA Leu | CGA Gly | GTG Val 235 | GCC Ala | TTA Leu | AAG Lys | AAA Lys | CTA Leu 240 | GGC Gly | TCC Ser | GAA Glu | GGA Gly | GAA Glu 245 | GAC Asp | CTC Leu | ATC Ile | 774 |
| CGT Arg | TTC Phe 250 | TTC Phe | AAT Asn | TCC Ser | CTC Leu | AAC Asn 255 | GAG Glu | GCG Ala | ACG Thr | ATG Met | GTG Val 260 | CTG Leu | GTG Val | TCC Ser | TGG Trp | 822 |
| ATT Ile 265 | ATG Met | TGG Trp | GTA Val | TAC Tyr | CCT Pro 270 | GTG Val | ATC Ile | GGC Gly | ATG Met | TTC Phe 275 | CCT Pro | GTT Val | GGA Gly | AGC Ser | AAG Lys 280 | 870 |
| ATC Ile | GTG Val | GAA Glu | AAA Lys | ATG Met 285 | GAC Asp | ATC Ile | ATC Ile | GTG Val | CTG Leu 290 | GTG Val | ACC Thr | AGC Ser | CTG Leu | GGG Gly 295 | AAA Lys | 918 |
| TAC Tyr | ATC Ile | TTC Phe | GCA Ala 300 | TCT Ser | ATA Ile | TTG Leu | GGC Gly | CAT His 305 | GTT Val | ATT Ile | CAT His | GGA Gly | GGA Gly 310 | ATT Ile | GTT Val | 966 |
| CTG Leu | CCA Pro | CTT Leu 315 | ATT Ile | TAT Tyr | TTT Phe | GTT Val | TTC Phe 320 | ACA Thr | CGA Arg | AAA Lys | AAC Asn | CCA Pro 325 | TTC Phe | AGA Arg | TTC Phe | 1014 |

FIG. 1D

```
CTC CTG GGC CTC CTC GCC CCA TTT GCA TTT GCT ACC GCG ACA GCA TTT GCT ACC TGC TCC   1062
Leu Leu Gly Leu Leu Ala Pro Phe Ala Phe Ala Thr Ala Thr Ala Phe Ala Thr Cys Ser
    330                 335             340

AGC TCA GCG ACC CTT CCC TCT ATG ATG AAG TGC GAA GAG AAC AAT                       1110
Ser Ser Ala Thr Leu Pro Ser Met Met Lys Cys Glu Glu Asn Asn
345                 350             355             360

GGT GTG GAC AAG AGG ATC AGC AGG TTT ATT TGC CCC GGG GCC                           1158
Gly Val Asp Lys Arg Ile Ser Arg Phe Ile Cys Pro Gly Ala
                365             370             375

GTG AAC ATG GAC GGA GCC ATC ATC TTC CAG CTC GTG CCG                               1206
Val Asn Met Asp Gly Ala Ile Ile Phe Gln Leu Val Ala
        380             385             390

ATT GCG CAA CTC AAC ATA GAG TCC GAG CAG GGA GCA GCC                               1254
Ile Ala Gln Leu Asn Ile Glu Ser Glu Gln Gly Ala Ala
                395             400             405

ATT CTA GTG ACT GCC ACA TCC AGT GTT GGA GCA ATT TTC ACC                           1302
Ile Leu Val Thr Ala Thr Ser Ser Val Gly Ala Ile Phe Thr
410             415             420

GCT GGG GTC CTC ATT ACC ATT GCC GAG CTG GGT ATT CCA GTG CTG                       1350
Ala Gly Val Leu Ile Thr Ile Ala Glu Leu Gly Ile Pro Val Leu
425             430             435             440
```

FIG. 1E

```
CCT ACT CAT GAC CTG CCT CTG ATC GCT GTG GAC TGG ATT GTG GAC          1398
Pro Thr His Asp Leu Pro Leu Ile Ala Val Asp Trp Ile Val Asp
            445             450             455

CGG ACC ACG GTG AAT GTG GTG GAT GGG GAG GCT CTG GGT GCA GGC          1446
Arg Thr Thr Val Asn Val Val Asp Gly Glu Ala Leu Gly Ala Gly
        460             465             470

ATT CTC CAC CTG AAT CAG AAG GCA ACA AAG AAA GGC GAG CAG GAA          1494
Ile Leu His Leu Asn Gln Lys Ala Thr Lys Lys Gly Glu Gln Glu
            475             480             485

CTT GCT GAG GTG AAA GAA GTG GCC ATC CCC AAC TGC GAG TCT GAG          1542
Leu Ala Glu Val Lys Glu Val Ala Ile Pro Asn Cys Glu Ser Glu
    490             495             500

ACA TCG CCC CTG GTG GTG GTG CAC CAG AAC CCC GGC GGT CCC GTG          1590
Thr Ser Pro Leu Val Val Val His Gln Asn Pro Gly Gly Pro Val
                505             510             515

AGT GCC CCA GAA TCC AAG GAG TCG GTT CTG TGATGGGGCT                   1636
Ser Ala Pro Glu Ser Lys Glu Ser Val Leu
                525             530
        520

GGGCTTTGGG CTTGCCTGCC AGCAGTGATG TCCCACCCTG TTCA                     1680
```

FIG. 2A

```
AAAGAAGAGA CCCTCCTAGA AAAGTAAAAT                                                        54
                                ATG ACT AAA AGC AAT GGA GAA GAG
                                Met Thr Lys Ser Asn Gly Glu Glu
                                  1                       5

CCC AAG ATG GGG GGC AGG ATG GAG AGA TTC CAG CAG GGA GTC CTG AAA        102
Pro Lys Met Gly Gly Arg Met Glu Arg Phe Gln Gln Gly Val Arg Lys
     10              15              20

CGC ACA CTT TTG GCC AGG AAG AAA AAT GTG CAG AAC ACA AAG GAG GTT        150
Arg Thr Leu Leu Ala Lys Lys Asn Val Gln Val Thr Thr Lys Glu Val
 25              30              35              40

GTT AAA AGT TAC CTG TTT CGG AAT GCT TTT TTT GTG CTG CTC ACA GTC        198
Val Lys Ser Tyr Leu Phe Arg Asn Ala Phe Phe Val Leu Leu Thr Val
             45              50              55

GCT GTC ATT GTG GGT ACA GGA ATC CTT TTT GGA TTT ACC ACC CGA CCA        246
Ala Val Ile Val Gly Thr Gly Ile Leu Phe Gly Phe Thr Thr Arg Pro
                 60              65              70

ATG AGC TAC CGG GAA GTC AAG TAC CTT TTC TCC TCT TTT CCT GAA GGG        294
Met Ser Tyr Arg Glu Val Lys Tyr Leu Phe Ser Ser Phe Pro Glu Gly
     75              80              85

ATG AGG TTA CAG ATG CTG GTC CCA CTT CTT ATC ATC AGT TCC AGT CTT        342
Met Arg Leu Gln Met Leu Val Pro Leu Leu Ile Ile Ser Ser Leu
     90              95              100
```

FIG. 2B

| | | | | | | | | | | | | | | | | |
|---|---|---|---|---|---|---|---|---|---|---|---|---|---|---|---|---|
| GTC Val 105 | ACA Thr | GGA Gly | ATG Met | GCG Ala | GCG Ala 110 | CTA Leu | GAT Asp | AGT Ser | AAG Lys | GCA Ala 115 | TCA Ser | GGG Gly | AAG Lys | TGG Trp | GAA Glu 120 | 390 |
| TGC Cys | GGA Gly | GCT Ala | GTA Val | GTC Val 125 | TAT Tyr | TAT Tyr | ATG Met | ACT Thr | ACC Thr 130 | CAT His | CCT Pro | ATC Ile | GCT Ala | GTG Val 135 | GTG Val | 438 |
| ATT Ile | GGC Gly | ATA Ile | ATC Ile | ATT Ile 140 | GTC Val | ATC Ile | ATC Ile 145 | ATC Ile | ATC Ile | CCT Pro | GGG Gly | AAG Lys | GGC Gly 150 | ACA Thr | AAG Lys | 486 |
| GAA Glu | AAC Asn | ATG Met | CAC His | GAA Glu | GGC Gly | ATT Ile | AAA Lys 160 | ATT Ile | GTA Val | CGA Arg | ACA Thr 165 | GCT Ala | GCA Ala | GAT Asp | | 534 |
| GCC Ala | TTC Phe 170 | CTG Leu | GAC Asp | TTG Leu | ATG Met | AGG Arg 175 | ATC Ile | ATG Met | TTA Leu | AAT Asn | CCA Pro 180 | AAT Asn | CTG Leu | GTA Val | GAA Glu | 582 |
| GCC Ala 185 | TGC Cys | TTT Phe | AAA Lys | TTT Phe | ATC Ile | TTT Phe 190 | AAA Lys | ACC Thr | TAT Tyr | GAG Glu | AAG Lys 195 | AAG Lys | AGA Arg | AGC Ser | TTT Phe | 630 |
| | | | | | | | | | | | | | | | Lys 200 | |
| GTG Val | CCC Pro | ATC Ile | GAG Gln | GCC Ala 205 | GGT Gly | GAA Glu | CCT Leu | ACG Thr 210 | ACG Thr | GAA Glu | GCT Ala | GTG Val | AGC Ser | ATA Ile | AAC Asn 215 | AAT Asn |
| | | | | | | | | | | | | | | | | 678 |

FIG. 2C

```
GTG TCT GAG GCC ATG GAG ACT CTT ACC CGA ATC ACA GAG CTG GTC      726
Val Ser Glu Ala Met Glu Thr Leu Thr Arg Ile Thr Glu Leu Val
            220                     225                 230

CCA GTT CCA GGA TCT AAT GGA GTC AAT GCC CTG GGT CTA GTT GTC      774
Pro Val Pro Gly Ser Asn Gly Val Asn Ala Leu Gly Leu Val Val
        235                 240                 245

TTC TCC ATG TGC TTC GGT TTT GTG ATT GGA ATG AAC AAG GAA CAG GGG  822
Phe Ser Met Cys Phe Gly Phe Val Ile Gly Met Asn Lys Glu Gln Gly
    250                 255                 260

GAG GCC CTG AGA GAG TTT TTC CTT TCT GAT AAC GAA GCC ATC ATG AGA  870
Glu Ala Leu Arg Glu Phe Phe Leu Ser Asp Asn Glu Ala Ile Met Arg
        265                 270                 275              280

CTG GTA GCA ATA ATG TGG TAT GCC CCC GTG GGT ATC CTC TTC          918
Leu Val Ala Ile Met Trp Tyr Ala Pro Val Gly Ile Leu Phe
                285                 290                 295

ATT GGG AAG ATT GAG ATG GAA GAC ATG GGT ATT GTG ATT GGG          966
Ile Gly Lys Ile Glu Met Glu Asp Met Gly Ile Val Ile Gly
        300                 305                 310

CTT GCC TAC ATG ACT ACC GTG ACT GTC GGC TTA CTC ATT CAC          1014
Leu Ala Tyr Met Thr Thr Val Thr Val Gly Leu Leu Ile His
        315             320                 325
```

FIG. 2D

```
GCA  GTC  ATC  GTC  TTG  CCA  CTC  CTC  TAC  TTC  TTG  GTA  ACA  CGG  AAA  AAC
Ala  Val  Ile  Val  Leu  Pro  Leu  Leu  Tyr  Phe  Leu  Val  Thr  Arg  Lys  Asn     1062
     330                      335                     340

CCT  TGG  GTT  TTT  ATT  GGA  GGG  TTG  CTG  CAA  GCA  TTG  CTC  ATC  ACC  GCT  CTG
Pro  Trp  Val  Phe  Ile  Gly  Gly  Leu  Leu  Gln  Ala  Leu  Leu  Ile  Thr  Ala  Leu  1110
345                      350                     355                          360

GGG  ACC  TCT  TCA  AGT  GCC  CTA  CCC  ACC  AAG  TGC  AAG  TTC  ATC  CTC  CTG
Gly  Thr  Ser  Ser  Ser  Ala  Leu  Pro  Thr  Lys  Cys  Lys  Phe  Ile  Leu  Leu     1158
               365                      370                     375

GAA  AAC  AAT  GGC  GTG  GAC  AAG  CGC  ACT  GTC  AGA  TTC  AAG  GTG  CTC  CCC
Glu  Asn  Asn  Gly  Val  Asp  Lys  Arg  Thr  Val  Arg  Phe  Lys  Val  Leu  Pro     1206
          380                      385                     390

GTA  GCC  ATT  AAC  ATG  GAT  GGG  ACT  GCC  TTT  CTC  TAT  GAG  GCT  TTG
Val  Ala  Ile  Asn  Met  Asp  Gly  Thr  Ala  Phe  Leu  Tyr  Glu  Ala  Leu          1254
395                      400                     405

GCT  ATT  TTC  ATT  GCT  CAA  GTT  AAC  TTT  GAA  CTG  AAC  TTC  GGA
Ala  Ile  Phe  Ile  Ala  Gln  Val  Asn  Phe  Glu  Leu  Asn  Phe  Gly               1302
410                      415                     420

CAA  ATT  ACA  ATC  AGC  GCC  ACA  GCT  GCC  AGT  ATT  GGG  GCA
Gln  Ile  Thr  Ile  Ser  Ala  Thr  Ala  Ala  Ser  Ile  Gly  Ala                    1350
425                 430                 435                 440
```

FIG. 2E

```
GCT ATT CCT CAG GCG GGC CTG GTC ACT ATG GTC ATT GTG CTG ACA   1398
Ala Gly Ile Pro Gln Ala Gly Leu Val Thr Met Val Ile Val Leu Thr
            445             450             455

TCT GTC GGC CTG CCC ACT GAC ATC CTC ACG ATC GCG GTG GAC         1446
Ser Val Gly Leu Pro Thr Asp Ile Leu Thr Ile Ala Val Asp
        460             465             470

TGG TTC TTG GAT CGC CTC ACC CGG ACC GTA ATC GGA GAC TCC         1494
Trp Phe Leu Asp Arg Leu Thr Arg Thr Val Ile Gly Asp Ser
        475             480             485

CTG GGA GCT ATT GGG GTG GAG CAC TTG CAT GAA CTG AAG AAC         1542
Leu Gly Ala Ile Gly Val Glu His Leu His Glu Leu Lys Asn
    490             495             500

AGA GAT GTT ATG GAA AAC TCA GTA CGA GAG ATT GAA ATG AAG         1590
Arg Asp Val Met Glu Asn Ser Val Arg Glu Ile Glu Met Lys
505             510             515

AAA CCA TAT CAA CTG ATT GCA CAG GAC AAT GAA ACT GAG CCC ATC     1638
Lys Pro Tyr Gln Leu Ile Ala Gln Asp Asn Glu Thr Glu Pro Ile
            525             530             535

GAC AGT GAA ACC AAG ATG TAGACTAACA TAAAGAAACA CTTT              1680
Asp Ser Glu Thr Lys Met
        540
```

FIG. 3A

```
                                                  GCGTTCCCAG ACC                                                       54
GATAGTGCTG AAGAGGAGG                                    ATG GCA TCT ACG GAA GGT GCC
                                                        Met Ala Ser Thr Glu Gly Ala
                                                         1           5

AAC AAT ATG CCC AAG CAG GTG GAA GTG CGA ATG CCA GAC AGT CAT CTT             102
Asn Asn Met Pro Lys Gln Val Glu Val Arg Met Pro Asp Ser His Leu
        10              15              20

GGC TCA GAG GAA CCC AAG CAC CGG CAC CTG CTG CGC CTG TGT GAC                 150
Gly Ser Glu Glu Pro Lys His Arg His Leu Leu Arg Leu Cys Asp
    25              30              35

AAG CTG GGG AAG AAT CTG CTC CTC ACG GTG TTT GGT ATC                         198
Lys Leu Gly Lys Asn Leu Leu Leu Thr Val Phe Gly Ile
40              45              50              55

CTG GGA GCA GTG TGT CGC CTT CTT CGC TCT CCC ATC CAC                         246
Leu Gly Ala Val Cys Arg Leu Leu Arg Ser Pro Ile His
                        65              70

CCT GAT GTT ATG TTA ATA GCC TTC CCA GGG GAT ATA CTC ATG AGG                 294
Pro Asp Val Met Leu Ile Ala Phe Pro Gly Asp Ile Leu Met Arg
        75              80              85

ATG CTA AAA ATG CTC CTG GGT ATT CTA TCC ATC TTA ATC ACA                     342
Met Leu Lys Met Leu Leu Gly Ile Leu Ser Ile Leu Ile Thr
    90              95              100
```

FIG. 3B

| | | | | | | | | | | | | | | | |
|---|---|---|---|---|---|---|---|---|---|---|---|---|---|---|---|
| GGG Gly | TTG Leu 105 | TCA Ser | GGC Gly | CTG Leu | GAT Asp | GCT Ala 110 | AAG Lys | GCT Ala | AGT Ser | GGC Gly | CGC Arg 115 | TTG Leu | GGC Gly | ACG Thr | AGA Arg | 390 |
| GCC Ala 120 | ATG Met | GTG Val | TAT Tyr | TAC Tyr | ATG Met 125 | TCC Ser | ACG Thr | ACC Thr | ATC Ile | ATT Ile 130 | GCT Ala | GCA Ala | GTA Val | CTG Leu | GGG Gly 135 | 438 |
| GTC Val | ATT Ile | CTG Leu | GTC Val | TTG Leu 140 | ATG Met | TCC Ser | ATC Ile | GCT Ala | ATC Ile | CAT His | CCA Pro | GGC Gly 145 | AAT Asn | CCC Pro | AAG Lys | 486 |
| CAG Gln | CTG Leu | GGG Gly | CCT Pro 155 | GGG Gly | ATT Ile | AAG Lys | AAG Lys | AAT Asn | GAT Asp 160 | GAA Glu | GTG Val | GGC Gly | CTC Leu | AAG Lys 150 | AAG Lys | 534 |
| TTC Phe | CTG Leu | GAC Asp 170 | CTT Leu | ATT Ile | CGA Arg | AAT Asn | CTC Leu 175 | TTC Phe | CCT Pro | TCC Ser | AGC Ser | CTG Leu 165 | AGC Ser | GAT Asp | GCC Ala | 582 |
| TGC Cys | TTT Phe 185 | CAA Gln | CAG Gln | CAG Gln | ATT Ile | ATT Ile | CAA Gln | ACA Thr 190 | ACG Thr | AAG Lys | AAA Lys | GTC Val 195 | CTG Leu | GTC Val | CAA Gln | 630 |
| CCG Pro 200 | CCA Pro | GAC Asp | GAG Glu | GAG Glu | GAG Glu | GCC Ala 205 | AAC Asn | GCA Ala | AGC Ser | GCT Ala 210 | GAA Glu | TCT Ser | GTT Val | CTG Leu | TTG Leu 215 | 678 |

FIG. 3C

| | | | | | | | | | | | | | | | | |
|---|---|---|---|---|---|---|---|---|---|---|---|---|---|---|---|---|
| AAC Asn | GAG Glu | ACT Thr | GTG Val | ACT Thr 220 | GAG Glu | CCG Pro | GAG Glu 225 | ACT Thr | AAG Lys | ATG Met | GTT Val | ATC Ile 230 | AAG Lys | | | 726 |
| AAG Lys | GGC Gly | CTG Leu | GAG Glu 235 | TTC Phe | AAG Lys | AAC Asn | ATG Met 240 | GGG Gly | GAT Asp | GTC Val | CTG Leu 245 | TTA Leu | GGT Gly | ATA Ile | GGG Gly | 774 |
| TTT Phe | ATT Ile 250 | GCT Ala | TTT Phe | GGC Gly | ATC Ile | GCT Ala 255 | ATG Met | AAG Lys | GGG Gly | GGA Gly 260 | GAT Asp | CAG Gln | GCC Ala | | | 822 |
| AAG Lys | CTG Leu 265 | ATG Met | GAT Asp | GTG Val | TTC Phe 270 | AAC Asn | TTG Leu | AAT Asn | GAG Glu 275 | ATT Ile | GTA Val | ATG Met | AAG Lys | | | 870 |
| TTA Leu 280 | GTG Val | ATC Ile | ATG Met | ATT Ile | GCA Ala | ATC Ile 285 | ATC Ile | TCT Ser | CCC Pro | CTG Leu 290 | GGT Gly | GCC Ala | TGC Cys | CTG Leu 295 | | 918 |
| ATC Ile | TGT Cys | GGA Gly | AAG Lys | ATC Ile 300 | GAC Asp 305 | TTA Leu | GAA Glu | GTG Val | GTT Val | GCT Ala 310 | AGG Arg | | | | | 966 |
| CAA Gln | CTG Leu | GGG Gly | ATG Met 315 | TAC Tyr | ATG Met | GTA Val | ACA Thr | GTG Val 320 | ATA Ile | GGC Gly | CTC Leu | ATC Ile 325 | CAC His | | | 1014 |

FIG. 3D

```
GGG  ATC  TTT  CCC  ATT  TAC  GTA  ACC  AGG  AAA  AAC                         1062
Gly  Gly  Ile  Phe  Leu  Pro  Leu  Ile  Tyr  Phe  Val  Val  Thr  Arg  Lys  Asn
     GGC  330       CTC            TTG  335                 340

CCC  TTC  TCC  CTT  TTT  GCT  GGC  ATT  TTC  CAA  GCT  TGG  ACT  GCC  CTG     1110
Pro  Phe  Ser  Leu  Phe  Ala  Gly  Ile  Phe  Gln  Ala  Trp  Thr  Ala  Leu
     345                      350                      355

GGC  ACC  GCT  TCC  AGT  GCT  ACT  TTG  CCT  GTC  TTT  CGT  TGC  CTG          1158
Gly  Thr  Ala  Ser  Ser  Ala  Thr  Leu  Pro  Val  Phe  Arg  Cys  Leu
360                 365                      370                 375

GAA  AAT  CTG  GGG  ACT  GAT  ATT  AAG  CGT  GTG  ACA  TTC  CGT  CTT          1206
Glu  Asn  Leu  Gly  Thr  Asp  Ile  Lys  Arg  Val  Thr  Phe  Arg  Leu
               380                      385                      390

GTT  GGA  GCA  ATG  AAC  GAT  ATG  AAT  GGT  TAT  TTC  AGA  CTT  GCC  GTG     1254
Val  Gly  Ala  Met  Asn  Asp  Met  Asn  Gly  Tyr  Phe  Arg  Leu  Ala  Val
               395                      400                      405

GCC  ATC  TTT  AGC  CAA  ATG  ATA  TTT  TAT  CTG  GTC  GAT  GCG  GGA          1302
Ala  Ile  Phe  Ser  Gln  Met  Ile  Phe  Tyr  Leu  Val  Asp  Ala  Gly
     410                      415                      420

CAG  ATT  GTA  ACT  AGC  CTC  ACA  GCC  ACC  CTG  GCA  AGC  GTC  GGA  GCG     1350
Gln  Ile  Val  Thr  Ser  Leu  Thr  Ala  Thr  Leu  Ala  Ser  Val  Gly  Ala
     425                      430                      435
```

FIG. 3E

```
GCC  AGT  ATC  CCC  AGT  GCC  GGG  CTG  GTC  ACC  ATG  CTC  CTC  ATT  CTG  ACA    1398
Ala  Ser  Ile  Pro  Ser  Ala  Gly  Leu  Val  Thr  Met  Leu  Leu  Ile  Leu  Thr
440                           445                550                      455

GCC  GTG  GGC  CTG  CCA  ACA  GAG  GAC  ATC  AGC  TTG  CTG  GTG  GCT  GTG  GAC    1446
Ala  Val  Gly  Leu  Pro  Thr  Glu  Asp  Ile  Ser  Leu  Leu  Val  Ala  Val  Asp
                    460                      465                      470

TGG  CTG  CTG  GAC  AGG  ATG  AGA  ACT  TCA  GTC  AAT  GTT  GTG  GGT  TCT         1494
Trp  Leu  Leu  Asp  Arg  Met  Arg  Thr  Ser  Val  Asn  Val  Val  Gly  Ser
               475                      480                      485

TTT  GGG  GCT  ATA  GTC  TAT  CAC  TCC  AAG  TCT  GAG  CTG  GAT  ACC                1542
Phe  Gly  Ala  Ile  Val  Tyr  His  Ser  Lys  Ser  Glu  Leu  Asp  Thr
          490                 495                 500

ATT  GAC  TCC  GAG  CAT  CGA  GTG  GAA  GAT  ATT  ATG  AAG  AAG  ACT               1590
Ile  Asp  Ser  Gln  His  Arg  Val  Glu  Asp  Ile  Met  Lys  Lys  Thr
     505                      510                     515

CAA  TCC  ATT  TAT  GAT  GAC  ATG  AAG  AAC  CAC  AGG  GAA  AGC  AAC  ACC  ATT    1638
Gln  Ser  Ile  Tyr  Asp  Asp  Met  Lys  Asn  His  Arg  Glu  Ser  Asn  Thr  Asn
520                           525                      530                535

CAA  TGT  GTC  TAT  GCT  GCA  CAC  AAC  TCT  GTC  ATA  GTA  GAT  GAA  TGC  AAG    1686
Gln  Cys  Val  Tyr  Ala  Ala  His  Asn  Ser  Val  Ile  Val  Asp  Glu  Cys  Lys
               540                      545                      550
```

FIG. 3F

```
GTA ACT CTG GCA GCC AAT GGA AAG TCA GCC GAC TGC AGT GTT GAG GAA
Val Thr Leu Ala Ala Asn Gly Lys Ser Ala Asp Cys Ser Val Glu Glu    1734
        555             560                 565

GAA CCT TGG AAA CGT GAG AAA TAAGGATATG AGTCTCAGCA AATTCTTGAA       1785
Glu Pro Trp Lys Arg Glu Lys
        570

TAAACTCCCC AGCGT                                                    1800
```

FIG. 4A

```
ATAGGGGCGA CAGCC                                                                                    51

ATG GGG AAA CCG GCG AGG AAA GGA TGC CCG AGT TGG                                                     99
Met Gly Lys Pro Ala Arg Lys Gly Cys Pro Ser Trp
 1            5                    10

AAG CGC TTC CTG AAG AAT AAC TGG GTG TTG CTG TCC ACC GTG GCC GCG                                    147
Lys Arg Phe Leu Lys Asn Asn Trp Val Leu Leu Ser Thr Val Ala Ala
          15              20                  25

GTG GTG CTA GGC ATT ACC ACA TTC TAC GGA GTC TTG CGA GAA CAC AGC AAC                                195
Val Val Leu Gly Ile Thr Thr Phe Tyr Gly Val Leu Arg Glu His Ser Asn
 30                      35                  40

CTC ACT CTA GAG AAA TTC TAC AAA TTT GCT CCT TTT GGA GAA ATT CTA                                    243
Leu Ser Thr Leu Glu Lys Phe Tyr Lys Phe Ala Pro Phe Gly Glu Ile Leu
 45                          50              55                  60

ATG GGG ATG CTG AAA CTC ATC GAT GCA CTG AAC GTA TCC ATA TCC AGC ATG                                291
Met Gly Met Arg Leu Lys Leu Ile Asp Ala Leu Asn Val Ser Ile Ser Met
                    65                  70                  75

ATT ACA GCT GTT GTA TAT TAT TCC TCC ACT ACC AAA AAA GAA ATT GGT                                    339
Ile Thr Ala Gly Val Tyr Tyr Leu Ala Ser Thr Thr Lys Lys Glu Ile Gly
         80                  85                  90

CTG CGC GCT GTC GTG TAT TTC TGT ACC ACC CTC ATT ATT GCT GTT ATT
Leu Arg Ala Val Val Tyr Phe Cys Thr Thr Leu Ile Ile Ala Val Ile
         95              100                 105
```

FIG. 4B

| | | | | | | | | | | | | | | | |
|---|---|---|---|---|---|---|---|---|---|---|---|---|---|---|---|
| CTA Leu | GGT Gly 110 | ATT Ile | GTG Val | CTG Leu | GTG Val 115 | AGC Ser | ATC Ile | AAG Lys | CCT Pro | GGT Gly 120 | GTC Val | ACC Thr | CAG Gln | AAA Lys | 387 |
| GTG Val 125 | GAA Glu | ATT Ile | GCG Ala | AGG Arg 130 | ACA Thr | AGC Ser | GGC Gly | ACC Thr | CCT Pro 135 | GAA Glu | GTC Val | AGT Ser | ACG Thr | GTG Val 140 | 435 |
| GAT Asp | ATG Met | TTA Leu | GCC Ala | CTC Leu | ATC Ile | AAT Asn | ATG Met 150 | TTC Phe | CCT Pro | GAG Glu | GTC Val | AAT Asn | CTT Leu 155 | GTC Val | 483 |
| CAG Gln | TGT Cys | TTT Phe 160 | GCC Ala | CAG Gln | TAC Tyr | AAA Lys | ACT Thr 165 | ATG Met | AGG Arg | AAG Lys | CGT Arg | GAA Glu | GTG Val 170 | AGT Ser | 531 |
| CCC Pro | GAT Asp 175 | CCA Pro | GCC Ala | ATG Met | AAC Asn | ATG Met 180 | AAA Lys | GAA Glu | TCC Ser | TTC Phe 185 | GAA Glu | GTG Val | AAG Lys | CCT Pro | 579 |
| ATG Met | ACT Thr | GCA Ala | ATT Ile | TCC Ser | AAG Lys 195 | AAC Asn | ACA Thr | GAA Glu | GAA Glu 200 | TAC Tyr | AAA Lys | ATT Ile | GCT Ala | GTC Val | 627 |
| GGC Gly 205 | TAT Tyr | TCA Ser | GAT Asp | GGC Gly 210 | ATA Ile | AAC Asn | AAA Lys | GTC Val | CTG Leu | GGC Gly 215 | TTG Leu | ATT Ile | TTT Phe | TGC Cys 220 | 675 |
| CTT Leu | TTT Phe | GGA Gly | CTT Leu 225 | GTC Val | ATT Ile | GGA Gly | AAA Lys | ATG Met 230 | GGA Gly | GAA Glu | AAG Lys | CAA Gln 235 | ATT Ile | | 723 |

FIG. 4C

| | | | | | | | | | | | | | | | | |
|---|---|---|---|---|---|---|---|---|---|---|---|---|---|---|---|---|
| CTG<br>Leu | GTG<br>Val | GAT<br>Asp | TTC<br>Phe<br>240 | TTC<br>Phe | AAT<br>Asn | GCT<br>Ala | TTG<br>Leu | AGT<br>Ser<br>245 | GAT<br>Asp | GCA<br>Ala | ACC<br>Thr | ATG<br>Met | AAA<br>Lys<br>250 | ATC<br>Ile | GTT<br>Val | 771 |
| CAG<br>Gln | ATC<br>Ile<br>255 | ATG<br>Met | TGT<br>Cys | TAT<br>Tyr | ATG<br>Met | CCA<br>Pro<br>260 | CTA<br>Leu | GGT<br>Gly | ATT<br>Ile | TTG<br>Leu | TTC<br>Phe<br>265 | CTG<br>Leu | ATT<br>Ile | GCT<br>Ala | | 819 |
| GGG<br>Gly | AAG<br>Lys<br>270 | ATC<br>Ile | ATA<br>Ile | GAA<br>Glu | GTT<br>Val | GAA<br>Glu<br>275 | GAC<br>Asp | TGG<br>Trp | GAA<br>Glu | ATA<br>Ile | TTC<br>Phe | CGC<br>Arg<br>280 | AAG<br>Lys | CTG<br>Leu | GGC<br>Gly | 867 |
| CTT<br>Leu<br>285 | TAC<br>Tyr | ATG<br>Met | GCC<br>Ala | ACA<br>Thr | GTC<br>Val<br>290 | GGG<br>Gly | ACT<br>Thr | CTT<br>Leu | GCA<br>Ala<br>295 | ATC<br>Ile | CAC<br>His | TCC<br>Ser | AAG<br>Lys | CTG<br>Leu | ATT<br>Ile<br>300 | 915 |
| ATT<br>Ile | CCG<br>Pro | CTG<br>Leu | ATA<br>Ile<br>305 | TTC<br>Phe | TAT<br>Tyr | GTA<br>Val<br>310 | GTC<br>Val | CTC<br>Leu | CGA<br>Arg | AAC<br>Asn | CCT<br>Pro | ATC<br>Ile | ATG<br>Met | TTC<br>Phe<br>315 | CGA<br>Arg | 963 |
| TTT<br>Phe | GCC<br>Ala | GGA<br>Gly<br>320 | ATG<br>Met | GCC<br>Ala | CAG<br>Gln | CTC<br>Leu<br>325 | CTC<br>Leu | ACA<br>Thr | GCT<br>Ala | AAC<br>Asn | CCT<br>Pro | ATG<br>Met | CTC<br>Leu<br>330 | ATC<br>Ile | TCT<br>Ser | 1011 |
| TCC<br>Ser<br>335 | AGT<br>Ser | TCA<br>Ser | ACA<br>Thr | GCA<br>Ala | CCT<br>Pro | CTG<br>Leu | ACC<br>Thr | GTC<br>Val<br>340 | TTC<br>Phe | CGC<br>Arg | TGT<br>Cys | GCT<br>Ala<br>345 | GAA<br>Glu | AAT<br>Asn | | 1059 |

FIG. 4D

| | | | | | | | | | | | | | | | |
|---|---|---|---|---|---|---|---|---|---|---|---|---|---|---|---|
| AAC Asn | CAG Gln 350 | GTG Val | GAC Asp | AAG Lys | AGG Arg | ATC Ile 355 | ACT Thr | CGA Arg | TTC Phe | CTG Val | TTA Leu 360 | CCC Pro | GTT Val | GGT Gly | GCA Ala | 1107 |
| ACA Thr 365 | ATC Ile | AAC Asn | ATG Met | GAT Asp | GGG Gly 370 | ACC Thr | GCG Ala | CTC Leu | TAT Tyr | GAA Glu 375 | GCA Ala | GTG Val | GCG Ala | GTG Val 380 | | 1155 |
| TTT Phe | ATT Ile | GCA Ala | CAG Gln | TTG Leu 385 | AAT Asn | GAC Asp | CTG Leu | TTG Leu 390 | GAC Asp | CTC Leu | ATT Ile | GGG Gly | CAG Gln | ATC Ile 395 | | 1203 |
| ACC Thr | ATC Ile | AGT Ser | ATC Ile 400 | GCT Ala | ACA Thr | TCT Ser | GCC Ala 405 | AGC Ser | ATC Ile | GGA Gly | GCT Ala 410 | GCT Ala | GGC Gly | | | 1251 |
| CCC Pro | CAG Gln | GCT Ala 415 | GAG Glu | GAT Asp | ACC Thr | ATG Met 420 | GTG Val | ATT Ile | CTG Leu | AGT Ser 425 | GAC Asp | GCC Ala | GTG Val | | | 1299 |
| CTG Leu | CCC Pro 430 | GCC Ala | GAG Glu | GAT Asp | ACC Thr 435 | CTG Leu | ATC Ile | ATT Ile | GCT Ala | GTC Val 440 | GAC Asp | TGG Trp | CTC Leu | CTG Leu | | 1347 |
| GAC Asp 445 | CGG Arg | TTC Phe | AGG Arg | ATG Met 450 | ACC Thr | AAC Asn | GTC Val | CTT Leu | GGT Gly 455 | GAT Asp | GCT Ala | TTT Phe | GGG Gly | ACT Thr 460 | | 1395 |

FIG. 4E

```
GGC ATT GTG GAA AAG CTC TCC AAG AAG GAG CTG GAG AAG ATG GAT GTT     1443
Gly Ile Val Glu Lys Leu Ser Lys Lys Glu Leu Glu Lys Met Asp Val
                465                 470                 475

TCA TCT GAA GTC AAC ATT GTG GAC AAT CCC TTT GCC TTG GAA TCC ACA ATC 1491
Ser Ser Glu Val Asn Ile Val Asp Asn Pro Phe Ala Leu Glu Ser Thr Ile
            480                 485                 490

CTT GAC AAC GAA GAC TCA GAC ACC AAG AAG TCT TAT GTC GAG ATG GGA GGC 1539
Leu Asp Asn Glu Asp Ser Asp Thr Lys Lys Ser Thr Val Glu Met Gly Gly
        495                 500                 505

TTT GCA GTA GAC AAG TCT GAC ACC ATC TCA TTC ACC ACC TCA CAG          1587
Phe Ala Val Asp Lys Ser Asp Thr Ile Ser Phe Thr Thr Ser Gln
    510                 515                 520

TTC TAGGGCCCCT GGCTGCAGAT GACTGGAAAC AAGGAAGGAC ATTTCGTGAG           1640
Phe
525

AGTCATCTCA AACACGGCTT AAGGAAAAGA GAAA                                 1674
```

FIG. 5A

```
ASCT1       MEKSNETNGLYDSAQAGPAAGPGAPGTAAGRARRCARFLRRQALVLL..TVSGVLAGAGLGAALR.GL
GLAST1   MTKSNGEEPRMGSRMTRFQQGVRKRTLLAKKKVQNITKEDVKSYLFRNAFVLL..TVSAVIVGTILGFALRPY.
GLT1        MASTEGANNMPKQVEVRMHDSHLSSEEPKHRNLGMRMCDKLGKNLLLSLTVFGVILGAVCGGLLRLAA
EAAC1                                MGKPARKGCDSKRFLKNNWLLLS.TVVAVVLGVIVIGVLVREYS

SLSRTQVTYLAFPGEMLRMIERVIILPLVVCSIVSQAASIDASCLQRLGGIRVAYFGL.TTLSASALAVALAFI
  66     KMSYREVKYFSFPGELLMRMLQVLVLPLIISSEVTGMAAIDSKASGKMGM.RAVVYMTTIIAVVIGIIIVII
  72     PIHPDVVMLIAFPGDILMRMLKVLILPLIISSLITGLSGLDAKASGRLGT.RAMVYYMSTTIIAAVIGIVLLA
  69     NLSTLDKFYFAFPGEILMRMLKLVIILPLIVSSMITGVAAIDSNVSGKIGL.RAVLYFCTTIIAVILGIVLVVS
  43

130     IKPGSGAQTLQSSDLGLEDSGPPVPKETVDSFLDLARNLFPSNLVVAAFRTYATDYKVV......TONSSS
 145     IHDGKGT.KENMYREGKIVQVTA......ADAFLDLIERNMFPPNLVEACFKQFKTSYEKRSFKVPIQANETLLG
 142     THPGNPKLKKQLGPKKNDEVSS......LDAFLDLIRNLFPENLVQACEQIQTVTKKVLVAPPS.EEANTTK
 116     IKPGVTQKVDEIDRTGSTPEVST......VDAMLDLIERNMFPENLVQACFQQYKTTREEV..TASDDTGKNGTE

205     GNVTHEKIPIGTEI..............EGMNILGVLFALVLGVALKKLGSEGEDLIRFFNSLNEATVLVSW
 212     AVINNVSEAMETLTRIREEMVPVPGSVN.GVNAIGLVVFESMCFGVIGNMKEQGGALREFFDSLNEAIVRLVAV
 209     AVISLINETMNEAPEETKIVIKKGLEFKDGMNVLGLIGFIAEGIAMCKMGVAGGADGVLOMSERDCHEVSDM
 182     ESVTAVMTTAVSENRIKEYRVVGLYS..DGINVLGLIVFCLVFGLVIGKMGEKGGILVDFFNALISDATVKIVQI

265     IMWYVPVGIMFLVGSRIVEMKDIIVLVTSIGKYIFASILGHVTHGGTIVPLIYFVFTRKNPFRFLLGLLAPFAT
 285     IMWYAPLGILFLIAGKILEMEDMGVIGGOIAMYTVTVIGLLIHAVIVPLIYFIVRKNPWVFIGGLLQALIT
 283     DHVVFPAGIACLICGKIIAIKDLEVAROIGMYMITVIVGLIHGGIELPLIYFVTRKNPESFAGIFQAWIT
 254     IMCYMPLGILFLIAGKILFIAGKIIEVEDWEIF.RKLGLYMVTVLSGLAIHSIVILPLIYFIVRKNPFRFAMGMTQALLT

339     AFATCSSSATIPSMMKCIEENNGVDKRISRFIEPICATVNMDGAAIFQCVAAVFIAGLNNIELNAGOIFGILVT
 350     AIGTSSSATLPITFKCLEENNGVDKRITFKFVLPVGATINMDGTALYEALAAIFIAGVNFEDENFGQEITSIT
 357     ALGTASSAGILPVTFRCLEDNLGIDKRVTREVLPVGATINMDGTALYEAVAAIFIAGMNGVILDGGQHVTVSLI
 327     ALMISSSSATLPVTFRCAEEKNRVDKRTTRFVLPVGATINMDGTALYEAVAAVFIAGLNDMDLSIGQIITESVT
```

FIG. 5B

```
413  ATASSVGAAGVPAGGVLTIAILEAIGIPTHDLPLILAVDWIVDRTTEVVNVEGDALGAGILHMENQKATKKGE
433  ATAASIGAAGIPOAGEVTMVIVLTSVGLPTDDITIIAVDWELDRLRTTNVLGDSLGAGIVEHLSRHELKNRD
431  ATLASIGAASIPSAGIVTMLLILTAVGLPTEDISLVAVDWLLDRMRTSVNVGDSFGAGIVYHLSKSELDTID
401  ATAASIGAAGVPOAGEVTMVIVLISAVGLPAEDVTLLIIAVDWLIDRFRTVVNVLGDAFGTGIVEKLSKKELEQMD

487  QELAEVKVEAIPNCKSEEETSPLVTHQNPAGPVASAPELESKESVL                532
507  VEMGNSVIEENEMKKPYQLIAQDNEPEKPVADSETKM                         543
505  SQHRMHEDIEMTKTQSVYDDTKNHRESNSNQCVYAAHNSVVIDECKVTLAANGKSADCSVEEEPWKREK  573
475  VSSEVNIVNPFALESATLDNEDSDTKKSYINGGFAVDKSDTISFTQTSQF             524
```

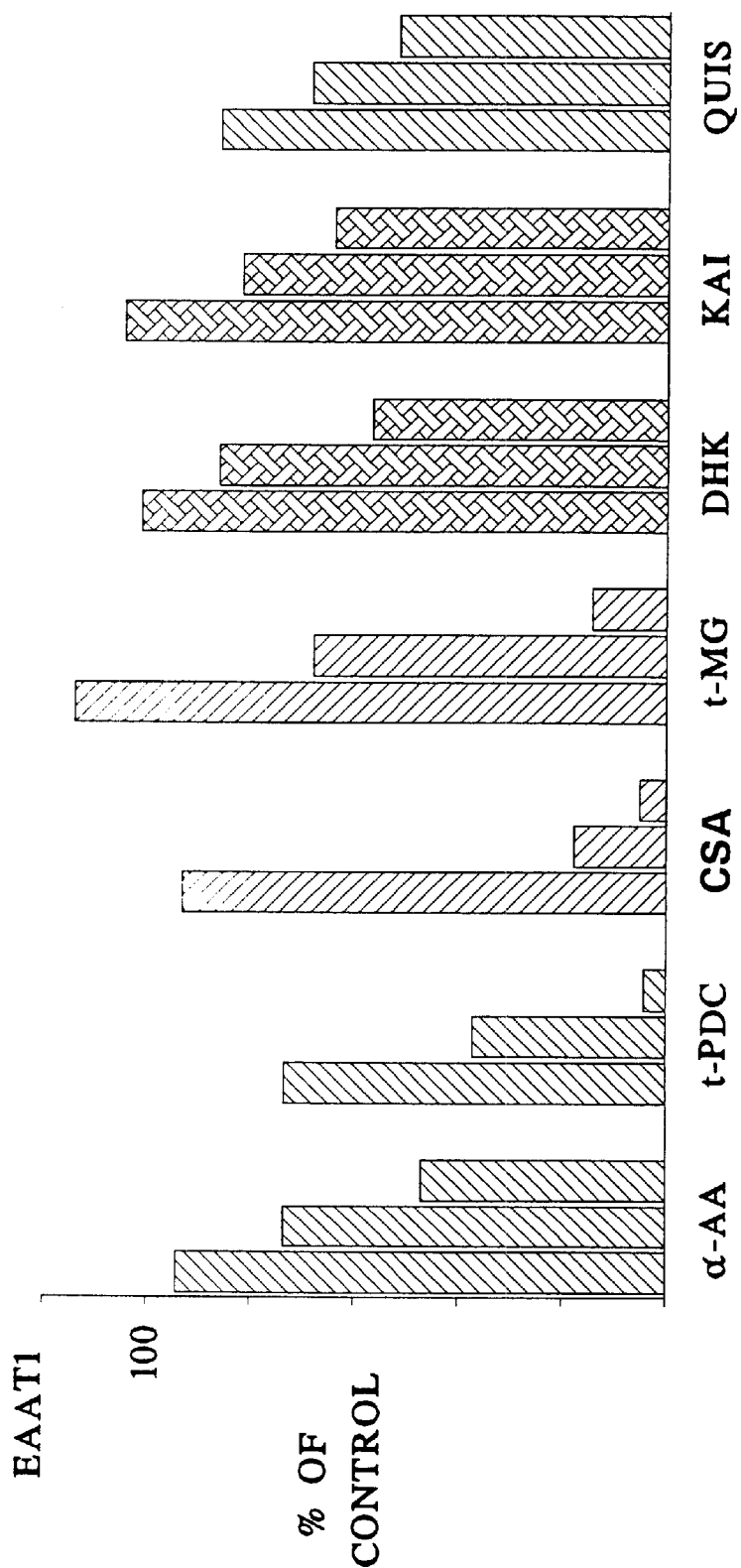

FIG. 11

```
EAAT1    MTKSNGEEPKMGGRMERFQQGVRKRTLLAKKKVQNTKKQVKSYLFGNPFVLI..TVTAVIVGI.LGFIIRPY.
EAAT2                                  MASTEGANNMPKQVEVRMPDSHLGSEEPKHRMLGLRLCDKLGKNLLLTLTVFGVLLGAVCGGLIRLAS
EAAT3                                                               MGKPARKGCPSWKRFLKNWVLIS.TVAAVLGITTGVEVFEHS
                                                                                              ———1———

72      RMSYREVKTFSFPGELIMRMLQMIVLPLITSSIVTGMAAIDSKASGKMGRAVVYMTTTIAVVIGILILLIVII
 69      PIMPDVMLIAFPGDLIMRMKMLIPLISSITGLSGIDAKASGRLGTRAMVYYMSTIIAAVLGVILLVLAI
 44      QNLSTLEKFYAFPGELLMRMLKLIILPLIISSMITGVAAIDSNVSGKIGLRAVVYFGTLLAVILGIVLVSI
                                 ———2———                                    ———3———

146      HPGKGT KENMHREGKIVRVTAADAFLDLTRNMFPNIVEACEKQEKIGYEKRSFKVPIQANBTLVGAVINNVS
143      HPGNPKLKKQLGPGKNDEVSSLDAFIDLTRNLFPENLVQACFQQIQTVKKVLVAPPPDEEANISAEVSLNN
118      KPGVTQKVGEIARTGSTPEVSTVDAMDLIRNMFPENIVQACFQQVKIKREV..KPESDPFMNMTEESFTAVM
                                                     ———4———                      ———5———

219      EAMETLTRITELVPVPGSVN.GVNALGIVVESMCFGFVIGNMKEQGQALREFFDSINEAIMRLVAVIMWYAPE
217      ETVTEVPEETKMVJKKGLEFKDGMNVLGLIGEFIAEGIAMGHMGDQAKLMVDEFILNEIVMKIVIMIMWYSPI
190      TTAISQNKTKEYKIVGMYS..DGINVLGLIVECLVFGLVIGKMGEKGQILNDFFNALISDATMKIVQIIMCVMPLI
                                                              ———6———

292      GILFLIAGKIVEMEDMGVIGGQIAMYTVTVIVGLLIHAVIVPLLYFLVTRKNPWFEIGGLLQALITAIGTSSS
291      GIACLICGKITAIKDLEVVARQHGMVMVTVIIGLIIHGGIFPLIIYTVTRQNPESLFAGIFQAWITALGTASS
261      GILFLIAGKIIEVEDWFIF.RKIGLMATVLTGLAIHSIVILPLIYFIVRKNPRFAMGMAQALIALMISSS
                                                    ———7———

366      SATIPITFKCLEENLGIDKRVTRFVLPVGATINMDGTALYEALAAIFIAQVNNFELNFGQIITISIATAASIG
385      AGTLPITFKCLEENLGIDKRVTRFVLPVGATINMDGTALYEAVAAIFIAQMNGVVIDGGQIVIVSLTAILASVG
334      SATIPITFKCAFENNQVDKRITRFVLPVGATINMDGTALYEAVAAVFIAQLNDLDIGIGQIITTSTAISASIG
                                     ———8———
```

FIG. 11A

```
  9  AAGIPQAGIVTMVIVITSVGIPTDDITLIAVDMFLDRLPTTNVLGDSLGAGIVEHLSRHEIKNRDVEMGNSV
440  AASIPSAGIVTMLLLILTAVGLPTEDISLLVADWLEDRMRISVNVGDSFGAGIVYHLSKSEDTIDSQMRVHE
439  AAGVPQAGIVTMVIVISAVGLPAEDVTLIIAVDWLIDRFRTMVNVIGDAFGTGIVEKISKKEIEQMDVSSEVNI
408

514  IEENEMKKPYQLIAQDN TEKPIDSETKM 542
513  DIEMTKTQSIYDDMKNHRESNSNQCVYAAHNSVIVDECKVTLAANGKSADCSVEEEPWKREK 574
482  VNPFALESTLDNEDSDTKKSYVNGGFAVDKSDTISFTQTSQF 525
```

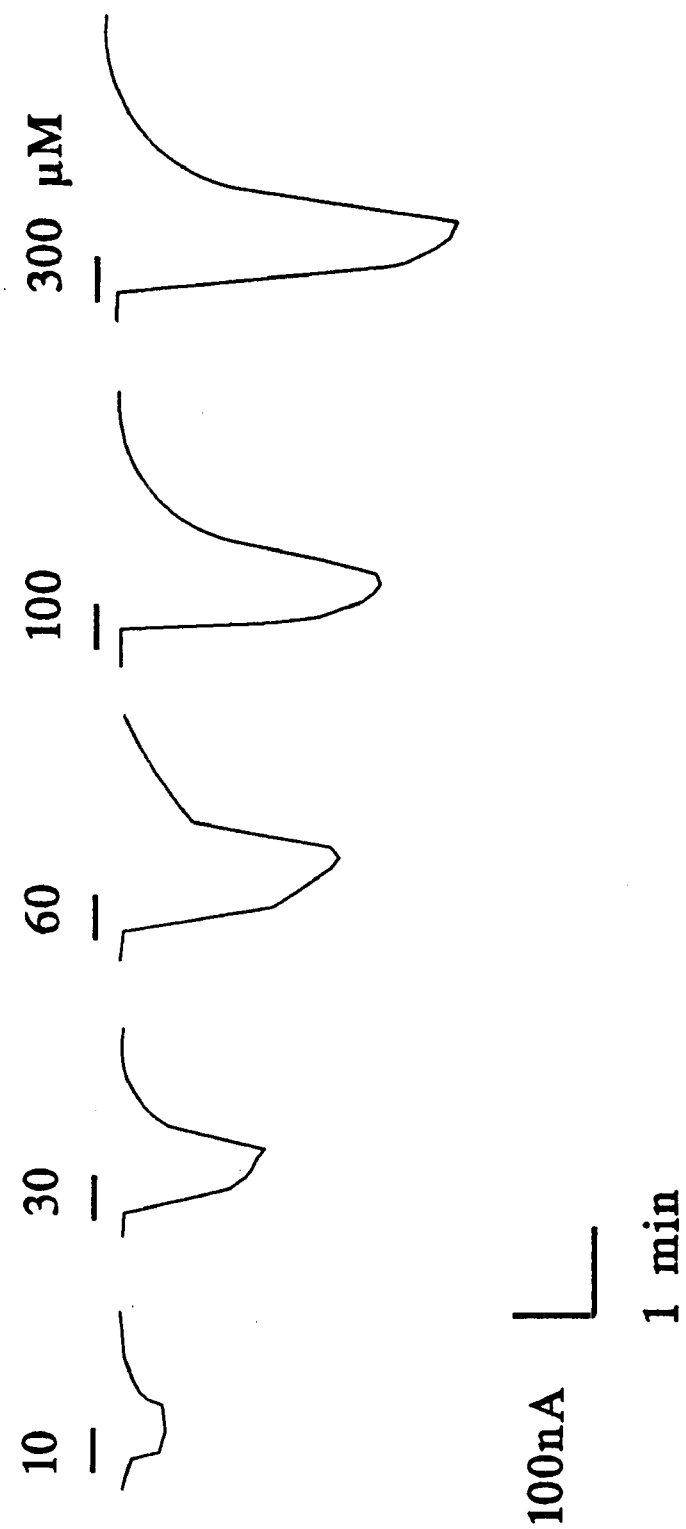

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 63 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CTGRGCRATG AARATGGCAG CCAGGGCYTC ATACAGGGCT GTGCCRTCCA TGTTRATGGT      60

RGC                                                                    63
```

(2) INFORMATION FOR SEQ ID NO:2:

(i) SEQUENCE CHARACTERISTICS:
      (A) LENGTH: 1680 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: 5'UTR
      (B) LOCATION: 1..30

(ix) FEATURE:
      (A) NAME/KEY: CDS
      (B) LOCATION: 31..1626

(ix) FEATURE:
      (A) NAME/KEY: 3'UTR
      (B) LOCATION: 1626..1680

(xi) SEQUENCE DESCRIPTION: SEQ ID NO:2:

```
CACCTCTAGC TCGGAGCGGC GTGTAGCGCC ATG GAG AAG AGC AAC GAG ACC AAC      54
                                 Met Glu Lys Ser Asn Glu Thr Asn
                                  1               5

GGC TAC CTT GAC AGC GCT CAG GCG GGG CCT GCG GCC GGG CCC GGA GCT      102
Gly Tyr Leu Asp Ser Ala Gln Ala Gly Pro Ala Ala Gly Pro Gly Ala
        10              15                  20
```

```
CCG GGG ACC GCG GCG GGA CGC GCA CGG CGT TGC GCG CGC TTC CTG CGG      150
Pro Gly Thr Ala Ala Gly Arg Ala Arg Arg Cys Ala Arg Phe Leu Arg
 25                  30                  35                  40

CGC CAA GCG CTG GTG CTG CTC ACC GTG TCC GGG GTG CTG GCG GGC GCG      198
Arg Gln Ala Leu Val Leu Leu Thr Val Ser Gly Val Leu Ala Gly Ala
                 45                  50                  55

GGC CTG GGC GCG GCG TTG CGC GGG CTC AGC CTG AGC CGC ACG CAG GTC      246
Gly Leu Gly Ala Ala Leu Arg Gly Leu Ser Leu Ser Arg Thr Gln Val
             60                  65                  70

ACC TAC CTG GCC TTC CCC GGC GAG ATG CTG CTC CGC ATG CTG CGC ATG      294
Thr Tyr Leu Ala Phe Pro Gly Glu Met Leu Leu Arg Met Leu Arg Met
         75                  80                  85

ATC ATC CTG CCG CTG GTG GTC TGC AGC CTG GTG TCG GGC GCC GCC TCG      342
Ile Ile Leu Pro Leu Val Val Cys Ser Leu Val Ser Gly Ala Ala Ser
     90                  95                 100

CTC GAT GCC AGC TGC CTC GGG CGT CTG GGC GGC ATC CGT GTC GCC TAC      390
Leu Asp Ala Ser Cys Leu Gly Arg Leu Gly Gly Ile Arg Val Ala Tyr
105                 110                 115                 120

TTT GGC CTC ACC ACA CTG AGT GCC TCG GCG CTC GCC GTG GCC TTG GCG      438
Phe Gly Leu Thr Thr Leu Ser Ala Ser Ala Leu Ala Val Ala Leu Ala
                125                 130                 135

TTC ATC ATC AAG CCA GGA TCC GGT GCG CAG ACC CTT CAG TCC AGC GAC      486
Phe Ile Ile Lys Pro Gly Ser Gly Ala Gln Thr Leu Gln Ser Ser Asp
            140                 145                 150

CTG GGG CTG GAG GAC TCG GGG CCT CCT CCT GTC CCC AAA GAG ACG GTG      534
Leu Gly Leu Glu Asp Ser Gly Pro Pro Pro Val Pro Lys Glu Thr Val
        155                 160                 165

GAC TCT TTC CTC GAC CTG GCC AGA AAC CTG TTT CCC TCC AAT CTT GTG      582
Asp Ser Phe Leu Asp Leu Ala Arg Asn Leu Phe Pro Ser Asn Leu Val
    170                 175                 180

GTT GCA GCT TTC CGT ACG TAT GCA ACC GAT TAT AAA GTC GTG ACC CAG      630
Val Ala Ala Phe Arg Thr Tyr Ala Thr Asp Tyr Lys Val Val Thr Gln
185                 190                 195                 200

AAC AGC AGC TCT GGA AAT GTA ACC CAT GAA AAG ATC CCC ATA GGC ACT      678
Asn Ser Ser Ser Gly Asn Val Thr His Glu Lys Ile Pro Ile Gly Thr
                205                 210                 215

GAG ATA GAA GGG ATG AAC ATT TTA GGA TTG GTC CTG TTT GCT CTG GTG      726
Glu Ile Glu Gly Met Asn Ile Leu Gly Leu Val Leu Phe Ala Leu Val
            220                 225                 230

TTA GGA GTG GCC TTA AAG AAA CTA GGC TCC GAA GGA GAA GAC CTC ATC      774
Leu Gly Val Ala Leu Lys Lys Leu Gly Ser Glu Gly Glu Asp Leu Ile
        235                 240                 245

CGT TTC TTC AAT TCC CTC AAC GAG GCG ACG ATG GTG CTG GTG TCC TGG      822
Arg Phe Phe Asn Ser Leu Asn Glu Ala Thr Met Val Leu Val Ser Trp
    250                 255                 260

ATT ATG TGG TAC GTA CCT GTG GGC ATC ATG TTC CTT GTT GGA AGC AAG      870
Ile Met Trp Tyr Val Pro Val Gly Ile Met Phe Leu Val Gly Ser Lys
265                 270                 275                 280

ATC GTG GAA ATG AAA GAC ATC ATC GTG CTG GTG ACC AGC CTG GGG AAA      918
Ile Val Glu Met Lys Asp Ile Ile Val Leu Val Thr Ser Leu Gly Lys
                285                 290                 295

TAC ATC TTC GCA TCT ATA TTG GGC CAT GTT ATT CAT GGA GGA ATT GTT      966
Tyr Ile Phe Ala Ser Ile Leu Gly His Val Ile His Gly Gly Ile Val
            300                 305                 310

CTG CCA CTT ATT TAT TTT GTT TTC ACA CGA AAA AAC CCA TTC AGA TTC     1014
Leu Pro Leu Ile Tyr Phe Val Phe Thr Arg Lys Asn Pro Phe Arg Phe
        315                 320                 325

CTC CTG GGC CTC CTC GCC CCA TTT GCG ACA GCA TTT GCT ACC TGC TCC     1062
Leu Leu Gly Leu Leu Ala Pro Phe Ala Thr Ala Phe Ala Thr Cys Ser
    330                 335                 340
```

```
AGC TCA GCG ACC CTT CCC TCT ATG ATG AAG TGC ATT GAA GAG AAC AAT     1110
Ser Ser Ala Thr Leu Pro Ser Met Met Lys Cys Ile Glu Glu Asn Asn
345                 350                 355                 360

GGT GTG GAC AAG AGG ATC AGC AGG TTT ATT CTC CCC ATC GGG GCC ACC     1158
Gly Val Asp Lys Arg Ile Ser Arg Phe Ile Leu Pro Ile Gly Ala Thr
                365                 370                 375

GTG AAC ATG GAC GGA GCA GCC ATC TTC CAG TGT GTG GCC GCG GTG TTC     1206
Val Asn Met Asp Gly Ala Ala Ile Phe Gln Cys Val Ala Ala Val Phe
            380                 385                 390

ATT GCG CAA CTC AAC AAC ATA GAG CTC AAC GCA GGA CAG ATT TTC ACC     1254
Ile Ala Gln Leu Asn Asn Ile Glu Leu Asn Ala Gly Gln Ile Phe Thr
        395                 400                 405

ATT CTA GTG ACT GCC ACA GCG TCC AGT GTT GGA GCA GCA GGC GTG CCA     1302
Ile Leu Val Thr Ala Thr Ala Ser Ser Val Gly Ala Ala Gly Val Pro
    410                 415                 420

GCT GGA GGG GTC CTC ACC ATT GCC ATT ATC CTG GAG GCC ATT GGG CTG     1350
Ala Gly Gly Val Leu Thr Ile Ala Ile Ile Leu Glu Ala Ile Gly Leu
425                 430                 435                 440

CCT ACT CAT GAC CTG CCT CTG ATC CTG GCT GTG GAC TGG ATT GTG GAC     1398
Pro Thr His Asp Leu Pro Leu Ile Leu Ala Val Asp Trp Ile Val Asp
                445                 450                 455

CGG ACC ACC ACG GTG GTG AAT GTG GAG GGG GAT GCC CTG GGT GCA GGC     1446
Arg Thr Thr Thr Val Val Asn Val Glu Gly Asp Ala Leu Gly Ala Gly
                460                 465                 470

ATT CTC CAC CAC CTG AAT CAG AAG GCA ACA AAG AAA GGC GAG CAG GAA     1494
Ile Leu His His Leu Asn Gln Lys Ala Thr Lys Lys Gly Glu Gln Glu
            475                 480                 485

CTT GCT GAG GTG AAA GTG GAA GCC ATC CCC AAC TGC AAG TCT GAG GAG     1542
Leu Ala Glu Val Lys Val Glu Ala Ile Pro Asn Cys Lys Ser Glu Glu
        490                 495                 500

GAG ACA TCG CCC CTG GTG ACA CAC CAG AAC CCC GCT GGC CCC GTG GCC     1590
Glu Thr Ser Pro Leu Val Thr His Gln Asn Pro Ala Gly Pro Val Ala
505                 510                 515                 520

AGT GCC CCA GAA CTG GAA TCC AAG GAG TCG GTT CTG TGATGGGGCT          1636
Ser Ala Pro Glu Leu Glu Ser Lys Glu Ser Val Leu
                525                 530

GGGCTTTGGG CTTGCCTGCC AGCAGTGATG TCCCACCCTG TTCA                    1680

(2) INFORMATION FOR SEQ ID NO:3:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Lys Ser Asn Glu Thr Asn Gly Tyr Leu Asp Ser Ala Gln Ala
 1               5                  10                  15

Gly Pro Ala Ala Gly Pro Gly Ala Pro Gly Thr Ala Ala Gly Arg Ala
            20                  25                  30

Arg Arg Cys Ala Arg Phe Leu Arg Arg Gln Ala Leu Val Leu Leu Thr
        35                  40                  45

Val Ser Gly Val Leu Ala Gly Ala Gly Leu Gly Ala Ala Leu Arg Gly
    50                  55                  60

Leu Ser Leu Ser Arg Thr Gln Val Thr Tyr Leu Ala Phe Pro Gly Glu
65                  70                  75                  80

Met Leu Leu Arg Met Leu Arg Met Ile Ile Leu Pro Leu Val Val Cys
```

-continued

```
                    85                  90                  95
Ser Leu Val Ser Gly Ala Ala Ser Leu Asp Ala Ser Cys Leu Gly Arg
                100                 105                 110

Leu Gly Gly Ile Arg Val Ala Tyr Phe Gly Leu Thr Thr Leu Ser Ala
            115                 120                 125

Ser Ala Leu Ala Val Ala Leu Ala Phe Ile Ile Lys Pro Gly Ser Gly
        130                 135                 140

Ala Gln Thr Leu Gln Ser Ser Asp Leu Gly Leu Glu Asp Ser Gly Pro
145                 150                 155                 160

Pro Pro Val Pro Lys Glu Thr Val Asp Ser Phe Leu Asp Leu Ala Arg
                165                 170                 175

Asn Leu Phe Pro Ser Asn Leu Val Ala Ala Phe Arg Thr Tyr Ala
            180                 185                 190

Thr Asp Tyr Lys Val Val Thr Gln Asn Ser Ser Ser Gly Asn Val Thr
        195                 200                 205

His Glu Lys Ile Pro Ile Gly Thr Glu Ile Glu Gly Met Asn Ile Leu
    210                 215                 220

Gly Leu Val Leu Phe Ala Leu Val Leu Gly Val Ala Leu Lys Lys Leu
225                 230                 235                 240

Gly Ser Glu Gly Glu Asp Leu Ile Arg Phe Phe Asn Ser Leu Asn Glu
                245                 250                 255

Ala Thr Met Val Leu Val Ser Trp Ile Met Trp Tyr Val Pro Val Gly
            260                 265                 270

Ile Met Phe Leu Val Gly Ser Lys Ile Val Glu Met Lys Asp Ile Ile
        275                 280                 285

Val Leu Val Thr Ser Leu Gly Lys Tyr Ile Phe Ala Ser Ile Leu Gly
    290                 295                 300

His Val Ile His Gly Gly Ile Val Leu Pro Leu Ile Tyr Phe Val Phe
305                 310                 315                 320

Thr Arg Lys Asn Pro Phe Arg Phe Leu Leu Gly Leu Leu Ala Pro Phe
                325                 330                 335

Ala Thr Ala Phe Ala Thr Cys Ser Ser Ser Ala Thr Leu Pro Ser Met
            340                 345                 350

Met Lys Cys Ile Glu Glu Asn Asn Gly Val Asp Lys Arg Ile Ser Arg
        355                 360                 365

Phe Ile Leu Pro Ile Gly Ala Thr Val Asn Met Asp Gly Ala Ala Ile
    370                 375                 380

Phe Gln Cys Val Ala Ala Val Phe Ile Ala Gln Leu Asn Asn Ile Glu
385                 390                 395                 400

Leu Asn Ala Gly Gln Ile Phe Thr Ile Leu Val Thr Ala Thr Ala Ser
                405                 410                 415

Ser Val Gly Ala Ala Gly Val Pro Ala Gly Gly Val Leu Thr Ile Ala
            420                 425                 430

Ile Ile Leu Glu Ala Ile Gly Leu Pro Thr His Asp Leu Pro Leu Ile
        435                 440                 445

Leu Ala Val Asp Trp Ile Val Asp Arg Thr Thr Thr Val Val Asn Val
    450                 455                 460

Glu Gly Asp Ala Leu Gly Ala Gly Ile Leu His His Leu Asn Gln Lys
465                 470                 475                 480

Ala Thr Lys Lys Gly Glu Gln Glu Leu Ala Glu Val Lys Val Glu Ala
                485                 490                 495

Ile Pro Asn Cys Lys Ser Glu Glu Thr Ser Pro Leu Val Thr His
            500                 505                 510
```

```
Gln Asn Pro Ala Gly Pro Val Ala Ser Ala Pro Glu Leu Glu Ser Lys
        515                 520                 525

Glu Ser Val Leu
    530

(2) INFORMATION FOR SEQ ID NO:4:

(i) SEQUENCE CHARACTERISTICS:
        (A) LENGTH: 1680 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..30

(ix) FEATURE:
        (A) NAME/KEY: CDS
        (B) LOCATION: 31..1656

(ix) FEATURE:
        (A) NAME/KEY: 3'UTR
        (B) LOCATION: 1657..1680

(xi) SEQUENCE DESCRIPTION: SEQ ID NO:4:

AAAGAAGAGA CCCTCCTAGA AAAGTAAAAT ATG ACT AAA AGC AAT GGA GAA GAG       54
                                 Met Thr Lys Ser Asn Gly Glu Glu
                                   1               5

CCC AAG ATG GGG GGC AGG ATG GAG AGA TTC CAG CAG GGA GTC CGT AAA      102
Pro Lys Met Gly Gly Arg Met Glu Arg Phe Gln Gln Gly Val Arg Lys
     10              15                  20

CGC ACA CTT TTG GCC AAG AAG AAA GTG CAG AAC ATT ACA AAG GAG GTT      150
Arg Thr Leu Leu Ala Lys Lys Lys Val Gln Asn Ile Thr Lys Glu Val
 25              30                  35                      40

GTT AAA AGT TAC CTG TTT CGG AAT GCT TTT GTG CTG CTC ACA GTC ACC      198
Val Lys Ser Tyr Leu Phe Arg Asn Ala Phe Val Leu Leu Thr Val Thr
                 45                  50                  55

GCT GTC ATT GTG GGT ACA ATC CTT GGA TTT ACC CTC CGA CCA TAC AGA      246
Ala Val Ile Val Gly Thr Ile Leu Gly Phe Thr Leu Arg Pro Tyr Arg
             60                  65                  70

ATG AGC TAC CGG GAA GTC AAG TAC TTC TCC TTT CCT GGG GAA CTT CTG      294
Met Ser Tyr Arg Glu Val Lys Tyr Phe Ser Phe Pro Gly Glu Leu Leu
         75                  80                  85

ATG AGG ATG TTA CAG ATG CTG GTC TTA CCA CTT ATC ATC TCC AGT CTT      342
Met Arg Met Leu Gln Met Leu Val Leu Pro Leu Ile Ile Ser Ser Leu
     90                  95                 100

GTC ACA GGA ATG GCG GCG CTA GAT AGT AAG GCA TCA GGG AAG TGG GAA      390
Val Thr Gly Met Ala Ala Leu Asp Ser Lys Ala Ser Gly Lys Trp Glu
105             110                 115                 120

TGC GGA GCT GTA GTC TAT TAT ATG ACT ACC ACC ATC ATT GCT GTG GTG      438
Cys Gly Ala Val Val Tyr Tyr Met Thr Thr Thr Ile Ile Ala Val Val
                125                 130                 135

ATT GGC ATA ATC ATT GTC ATC ATC ATC CAT CCT GGG AAG GGC ACA AAG      486
Ile Gly Ile Ile Ile Val Ile Ile Ile His Pro Gly Lys Gly Thr Lys
            140                 145                 150

GAA AAC ATG CAC AGA GAA GGC AAA ATT GTA CGA GTG ACA GCT GCA GAT      534
Glu Asn Met His Arg Glu Gly Lys Ile Val Arg Val Thr Ala Ala Asp
        155                 160                 165

GCC TTC CTG GAC TTG ATC AGG AAC ATG TTA AAT CCA AAT CTG GTA GAA      582
Ala Phe Leu Asp Leu Ile Arg Asn Met Leu Asn Pro Asn Leu Val Glu
170                 175                 180
```

```
GCC TGC TTT AAA CAG TTT AAA ACC AAC TAT GAG AAG AGA AGC TTT AAA      630
Ala Cys Phe Lys Gln Phe Lys Thr Asn Tyr Glu Lys Arg Ser Phe Lys
185             190                 195                 200

GTG CCC ATC CAG GCC AAC GAA ACG CTT GTG GGT GCT GTG ATA AAC AAT      678
Val Pro Ile Gln Ala Asn Glu Thr Leu Val Gly Ala Val Ile Asn Asn
                205                 210                 215

GTG TCT GAG GCC ATG GAG ACT CTT ACC CGA ATC ACA GAG GAG CTG GTC      726
Val Ser Glu Ala Met Glu Thr Leu Thr Arg Ile Thr Glu Glu Leu Val
        220                 225                 230

CCA GTT CCA GGA TCT GTG AAT GGA GTC AAT GCC CTG GGT CTA GTT GTC      774
Pro Val Pro Gly Ser Val Asn Gly Val Asn Ala Leu Gly Leu Val Val
            235                 240                 245

TTC TCC ATG TGC TTC GGT TTT GTG ATT GGA AAC ATG AAG GAA CAG GGG      822
Phe Ser Met Cys Phe Gly Phe Val Ile Gly Asn Met Lys Glu Gln Gly
        250                 255                 260

CAG GCC CTG AGA GAG TTC TTT GAT TCT CTT AAC GAA GCC ATC ATG AGA      870
Gln Ala Leu Arg Glu Phe Phe Asp Ser Leu Asn Glu Ala Ile Met Arg
265             270                 275                 280

CTG GTA GCA GTA ATA ATG TGG TAT GCC CCC GTG GGT ATT CTC TTC CTG      918
Leu Val Ala Val Ile Met Trp Tyr Ala Pro Val Gly Ile Leu Phe Leu
                285                 290                 295

ATT GCT GGG AAG ATT GTG GAG ATG GAA GAC ATG GGT GTG ATT GGG GGG      966
Ile Ala Gly Lys Ile Val Glu Met Glu Asp Met Gly Val Ile Gly Gly
            300                 305                 310

CAG CTT GCC ATG TAC ACC GTG ACT GTC ATT GTT GGC TTA CTC ATT CAC     1014
Gln Leu Ala Met Tyr Thr Val Thr Val Ile Val Gly Leu Leu Ile His
        315                 320                 325

GCA GTC ATC GTC TTG CCA CTC CTC TAC TTC TTG GTA ACA CGG AAA AAC     1062
Ala Val Ile Val Leu Pro Leu Leu Tyr Phe Leu Val Thr Arg Lys Asn
330             335                 340

CCT TGG GTT TTT ATT GGA GGG TTG CTG CAA GCA CTC ATC ACC GCT CTG     1110
Pro Trp Val Phe Ile Gly Gly Leu Leu Gln Ala Leu Ile Thr Ala Leu
345             350                 355                 360

GGG ACC TCT TCA AGT TCT GCC ACC CTA CCC ATC ACC TTC AAG TGC CTG     1158
Gly Thr Ser Ser Ser Ser Ala Thr Leu Pro Ile Thr Phe Lys Cys Leu
            365                 370                 375

GAA GAG AAC AAT GGC GTG GAC AAG CGC GTC ACC AGA TTC GTG CTC CCC     1206
Glu Glu Asn Asn Gly Val Asp Lys Arg Val Thr Arg Phe Val Leu Pro
                380                 385                 390

GTA GGA GCC ACC ATT AAC ATG GAT GGG ACT GCC CTC TAT GAG GCT TTG     1254
Val Gly Ala Thr Ile Asn Met Asp Gly Thr Ala Leu Tyr Glu Ala Leu
            395                 400                 405

GCT GCC ATT TTC ATT GCT CAA GTT AAC AAC TTT GAA CTG AAC TTC GGA     1302
Ala Ala Ile Phe Ile Ala Gln Val Asn Asn Phe Glu Leu Asn Phe Gly
410             415                 420

CAA ATT ATT ACA ATC AGC ATC ACA GCC ACA GCT GCC AGT ATT GGG GCA     1350
Gln Ile Ile Thr Ile Ser Ile Thr Ala Thr Ala Ala Ser Ile Gly Ala
425             430                 435                 440

GCT GGA ATT CCT CAG GCG GGC CTG GTC ACT ATG GTC ATT GTG CTG ACA     1398
Ala Gly Ile Pro Gln Ala Gly Leu Val Thr Met Val Ile Val Leu Thr
                445                 450                 455

TCT GTC GGC CTG CCC ACT GAC GAC ATC ACG CTC ATC ATC GCG GTG GAC     1446
Ser Val Gly Leu Pro Thr Asp Asp Ile Thr Leu Ile Ile Ala Val Asp
            460                 465                 470

TGG TTC TTG GAT CGC CTC CGG ACC ACC ACC AAC GTA CTG GGA GAC TCC     1494
Trp Phe Leu Asp Arg Leu Arg Thr Thr Thr Asn Val Leu Gly Asp Ser
        475                 480                 485

CTG GGA GCT GGG ATT GTG GAG CAC TTG TCA CGA CAT GAA CTG AAG AAC     1542
Leu Gly Ala Gly Ile Val Glu His Leu Ser Arg His Glu Leu Lys Asn
```

```
                490                 495                 500
AGA GAT GTT GAA ATG GGT AAC TCA GTG ATT GAA GAG AAT GAA ATG AAG        1590
Arg Asp Val Glu Met Gly Asn Ser Val Ile Glu Glu Asn Glu Met Lys
505                 510                 515                 520

AAA CCA TAT CAA CTG ATT GCA CAG GAC AAT GAA ACT GAG AAA CCC ATC        1638
Lys Pro Tyr Gln Leu Ile Ala Gln Asp Asn Glu Thr Glu Lys Pro Ile
            525                 530                 535

GAC AGT GAA ACC AAG ATG TAGACTAACA TAAAGAAACA CTTT                     1680
Asp Ser Glu Thr Lys Met
            540

(2) INFORMATION FOR SEQ ID NO:5:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:5:

Met Thr Lys Ser Asn Gly Glu Glu Pro Lys Met Gly Gly Arg Met Glu
1               5                   10                  15

Arg Phe Gln Gln Gly Val Arg Lys Arg Thr Leu Leu Ala Lys Lys Lys
                20                  25                  30

Val Gln Asn Ile Thr Lys Glu Val Lys Ser Tyr Leu Phe Arg Asn
            35                  40                  45

Ala Phe Val Leu Leu Thr Val Thr Ala Val Ile Val Gly Thr Ile Leu
        50                  55                  60

Gly Phe Thr Leu Arg Pro Tyr Arg Met Ser Tyr Arg Glu Val Lys Tyr
65                  70                  75                  80

Phe Ser Phe Pro Gly Glu Leu Leu Met Arg Met Leu Gln Met Leu Val
                85                  90                  95

Leu Pro Leu Ile Ile Ser Ser Leu Val Thr Gly Met Ala Ala Leu Asp
            100                 105                 110

Ser Lys Ala Ser Gly Lys Trp Glu Cys Gly Ala Val Val Tyr Tyr Met
        115                 120                 125

Thr Thr Thr Ile Ile Ala Val Val Ile Gly Ile Ile Val Ile Ile
130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
                165                 170                 175

Met Leu Asn Pro Asn Leu Val Glu Ala Cys Phe Lys Gln Phe Lys Thr
            180                 185                 190

Asn Tyr Glu Lys Arg Ser Phe Lys Val Pro Ile Gln Ala Asn Glu Thr
        195                 200                 205

Leu Val Gly Ala Val Ile Asn Asn Val Ser Glu Ala Met Glu Thr Leu
    210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
            260                 265                 270

Ser Leu Asn Glu Ala Ile Met Arg Leu Val Ala Val Ile Met Trp Tyr
        275                 280                 285
```

```
Ala Pro Val Gly Ile Leu Phe Leu Ile Ala Gly Lys Ile Val Glu Met
    290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
            340                 345                 350

Leu Gln Ala Leu Ile Thr Ala Leu Gly Thr Ser Ser Ser Ala Thr
        355                 360                 365

Leu Pro Ile Thr Phe Lys Cys Leu Glu Glu Asn Asn Gly Val Asp Lys
    370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Glu Leu Asn Phe Gly Gln Ile Ile Thr Ile Ser Ile Thr
            420                 425                 430

Ala Thr Ala Ala Ser Ile Gly Ala Ala Gly Ile Pro Gln Ala Gly Leu
        435                 440                 445

Val Thr Met Val Ile Val Leu Thr Ser Val Gly Leu Pro Thr Asp Asp
    450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
        515                 520                 525

Asp Asn Glu Thr Glu Lys Pro Ile Asp Ser Glu Thr Lys Met
    530                 535                 540

(2) INFORMATION FOR SEQ ID NO:6:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..33

(ix) FEATURE:
        (A) NAME/KEY: CDS
        (B) LOCATION: 34..1755

(ix) FEATURE:
        (A) NAME/KEY: 3'UTR
        (B) LOCATION: 1756..1800

(xi) SEQUENCE DESCRIPTION: SEQ ID NO:6:

GATAGTGCTG AAGAGGAGGG GCGTTCCCAG ACC ATG GCA TCT ACG GAA GGT GCC      54
                                    Met Ala Ser Thr Glu Gly Ala
                                      1               5

AAC AAT ATG CCC AAG CAG GTG GAA GTG CGA ATG CCA GAC AGT CAT CTT     102
```

```
                                                                           -continued Asn Asn Met Pro Lys Gln Val Glu Val Arg Met Pro Asp Ser His Leu
         10                  15                  20

GGC TCA GAG GAA CCC AAG CAC CGG CAC CTG GGC CTG CGC CTG TGT GAC            150
Gly Ser Glu Glu Pro Lys His Arg His Leu Gly Leu Arg Leu Cys Asp
     25                  30                  35

AAG CTG GGG AAG AAT CTG CTG CTC ACC CTG ACG GTG TTT GGT GTC ATC            198
Lys Leu Gly Lys Asn Leu Leu Leu Thr Leu Thr Val Phe Gly Val Ile
 40                  45                  50                  55

CTG GGA GCA GTG TGT GGA GGG CTT CTT CGC TTG GCA TCT CCC ATC CAC            246
Leu Gly Ala Val Cys Gly Gly Leu Leu Arg Leu Ala Ser Pro Ile His
             60                  65                  70

CCT GAT GTG GTT ATG TTA ATA GCC TTC CCA GGG GAT ATA CTC ATG AGG            294
Pro Asp Val Val Met Leu Ile Ala Phe Pro Gly Asp Ile Leu Met Arg
             75                  80                  85

ATG CTA AAA ATG CTC ATT CTG GGT CTA ATC ATC TCC AGC TTA ATC ACA            342
Met Leu Lys Met Leu Ile Leu Gly Leu Ile Ile Ser Ser Leu Ile Thr
         90                  95                 100

GGG TTG TCA GGC CTG GAT GCT AAG GCT AGT GGC CGC TTG GGC ACG AGA            390
Gly Leu Ser Gly Leu Asp Ala Lys Ala Ser Gly Arg Leu Gly Thr Arg
    105                 110                 115

GCC ATG GTG TAT TAC ATG TCC ACG ACC ATC ATT GCT GCA GTA CTG GGG            438
Ala Met Val Tyr Tyr Met Ser Thr Thr Ile Ile Ala Ala Val Leu Gly
120                 125                 130                 135

GTC ATT CTG GTC TTG GCT ATC CAT CCA GGC AAT CCC AAG CTC AAG AAG            486
Val Ile Leu Val Leu Ala Ile His Pro Gly Asn Pro Lys Leu Lys Lys
                140                 145                 150

CAG CTG GGG CCT GGG AAG AAG AAT GAT GAA GTG TCC AGC CTG GAT GCC            534
Gln Leu Gly Pro Gly Lys Lys Asn Asp Glu Val Ser Ser Leu Asp Ala
            155                 160                 165

TTC CTG GAC CTT ATT CGA AAT CTC TTC CCT GAA AAC CTT GTC CAA GCC            582
Phe Leu Asp Leu Ile Arg Asn Leu Phe Pro Glu Asn Leu Val Gln Ala
        170                 175                 180

TGC TTT CAA CAG ATT CAA ACA GTG ACG AAG AAA GTC CTG GTT GCA CCA            630
Cys Phe Gln Gln Ile Gln Thr Val Thr Lys Lys Val Leu Val Ala Pro
    185                 190                 195

CCG CCA GAC GAG GAG GCC AAC GCA ACC AGC GCT GAA GTC TCT CTG TTG            678
Pro Pro Asp Glu Glu Ala Asn Ala Thr Ser Ala Glu Val Ser Leu Leu
200                 205                 210                 215

AAC GAG ACT GTG ACT GAG GTG CCG GAG GAG ACT AAG ATG GTT ATC AAG            726
Asn Glu Thr Val Thr Glu Val Pro Glu Glu Thr Lys Met Val Ile Lys
                220                 225                 230

AAG GGC CTG GAG TTC AAG GAT GGG ATG AAC GTC TTA GGT CTG ATA GGG            774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC            822
Phe Phe Ile Ala Phe Gly Ile Ala Met Gly Lys Met Gly Asp Gln Ala
        250                 255                 260

AAG CTG ATG GTG GAT TTC TTC AAC ATT TTG AAT GAG ATT GTA ATG AAG            870
Lys Leu Met Val Asp Phe Phe Asn Ile Leu Asn Glu Ile Val Met Lys
    265                 270                 275

TTA GTG ATC ATG ATC ATG TGG TAC TCT CCC CTG GGT ATC GCC TGC CTG            918
Leu Val Ile Met Ile Met Trp Tyr Ser Pro Leu Gly Ile Ala Cys Leu
280                 285                 290                 295

ATC TGT GGA AAG ATC ATT GCA ATC AAG GAC TTA GAA GTG GTT GCT AGG            966
Ile Cys Gly Lys Ile Ile Ala Ile Lys Asp Leu Glu Val Val Ala Arg
                300                 305                 310

CAA CTG GGG ATG TAC ATG GTA ACA GTG ATC ATA GGC CTC ATC ATC CAC           1014
Gln Leu Gly Met Tyr Met Val Thr Val Ile Ile Gly Leu Ile Ile His
            315                 320                 325
```

```
GGG GGC ATC TTT CTC CCC TTG ATT TAC TTT GTA GTG ACC AGG AAA AAC    1062
Gly Gly Ile Phe Leu Pro Leu Ile Tyr Phe Val Val Thr Arg Lys Asn
        330                 335                 340

CCC TTC TCC CTT TTT GCT GGC ATT TTC CAA GCT TGG ATC ACT GCC CTG    1110
Pro Phe Ser Leu Phe Ala Gly Ile Phe Gln Ala Trp Ile Thr Ala Leu
    345                 350                 355

GGC ACC GCT TCC AGT GCT GGA ACT TTG CCT GTC ACC TTT CGT TGC CTG    1158
Gly Thr Ala Ser Ser Ala Gly Thr Leu Pro Val Thr Phe Arg Cys Leu
360                 365                 370                 375

GAA GAA AAT CTG GGG ATT GAT AAG CGT GTG ACT AGA TTC GTC CTT CCT    1206
Glu Glu Asn Leu Gly Ile Asp Lys Arg Val Thr Arg Phe Val Leu Pro
                380                 385                 390

GTT GGA GCA ACC ATT AAC ATG GAT GGT ACA GCC CTT TAT GAA GCG GTG    1254
Val Gly Ala Thr Ile Asn Met Asp Gly Thr Ala Leu Tyr Glu Ala Val
            395                 400                 405

GCC GCC ATC TTT ATA GCC CAA ATG AAT GGT GTT GTC CTG GAT GGA GGA    1302
Ala Ala Ile Phe Ile Ala Gln Met Asn Gly Val Val Leu Asp Gly Gly
        410                 415                 420

CAG ATT GTG ACT GTA AGC CTC ACA GCC ACC CTG GCA AGC GTC GGC GCG    1350
Gln Ile Val Thr Val Ser Leu Thr Ala Thr Leu Ala Ser Val Gly Ala
    425                 430                 435

GCC AGT ATC CCC AGT GCC GGG CTG GTC ACC ATG CTC CTC ATT CTG ACA    1398
Ala Ser Ile Pro Ser Ala Gly Leu Val Thr Met Leu Leu Ile Leu Thr
440                 445                 450                 455

GCC GTG GGC CTG CCA ACA GAG GAC ATC AGC TTG CTG GTG GCT GTG GAC    1446
Ala Val Gly Leu Pro Thr Glu Asp Ile Ser Leu Leu Val Ala Val Asp
                460                 465                 470

TGG CTG CTG GAC AGG ATG AGA ACT TCA GTC AAT GTT GTG GGT GAC TCT    1494
Trp Leu Leu Asp Arg Met Arg Thr Ser Val Asn Val Val Gly Asp Ser
            475                 480                 485

TTT GGG GCT GGG ATA GTC TAT CAC CTC TCC AAG TCT GAG CTG GAT ACC    1542
Phe Gly Ala Gly Ile Val Tyr His Leu Ser Lys Ser Glu Leu Asp Thr
        490                 495                 500

ATT GAC TCC CAG CAT CGA GTG CAT GAA GAT ATT GAA ATG ACC AAG ACT    1590
Ile Asp Ser Gln His Arg Val His Glu Asp Ile Glu Met Thr Lys Thr
    505                 510                 515

CAA TCC ATT TAT GAT GAC ATG AAG AAC CAC AGG GAA AGC AAC TCT AAT    1638
Gln Ser Ile Tyr Asp Asp Met Lys Asn His Arg Glu Ser Asn Ser Asn
520                 525                 530                 535

CAA TGT GTC TAT GCT GCA CAC AAC TCT GTC ATA GTA GAT GAA TGC AAG    1686
Gln Cys Val Tyr Ala Ala His Asn Ser Val Ile Val Asp Glu Cys Lys
                540                 545                 550

GTA ACT CTG GCA GCC AAT GGA AAG TCA GCC GAC TGC AGT GTT GAG GAA    1734
Val Thr Leu Ala Ala Asn Gly Lys Ser Ala Asp Cys Ser Val Glu Glu
            555                 560                 565

GAA CCT TGG AAA CGT GAG AAA TAAGGATATG AGTCTCAGCA AATTCTTGAA       1785
Glu Pro Trp Lys Arg Glu Lys
        570

TAAACTCCCC AGCGT                                                   1800

(2) INFORMATION FOR SEQ ID NO:7:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:7:

Met Ala Ser Thr Glu Gly Ala Asn Asn Met Pro Lys Gln Val Glu Val
```

-continued

```
  1                   5                       10                      15

Arg Met Pro Asp Ser His Leu Gly Ser Glu Pro Lys His Arg His
             20                      25                      30

Leu Gly Leu Arg Leu Cys Asp Lys Leu Gly Lys Asn Leu Leu Thr
             35                      40                      45

Leu Thr Val Phe Gly Val Ile Leu Gly Ala Val Cys Gly Leu Leu
 50                      55                      60

Arg Leu Ala Ser Pro Ile His Pro Asp Val Val Met Leu Ile Ala Phe
 65                      70                      75                      80

Pro Gly Asp Ile Leu Met Arg Met Leu Lys Met Leu Ile Leu Gly Leu
                         85                      90                      95

Ile Ile Ser Ser Leu Ile Thr Gly Leu Ser Gly Leu Asp Ala Lys Ala
                        100                     105                     110

Ser Gly Arg Leu Gly Thr Arg Ala Met Val Tyr Tyr Met Ser Thr Thr
                        115                     120                     125

Ile Ile Ala Ala Val Leu Gly Val Ile Leu Val Leu Ala Ile His Pro
                        130                     135                     140

Gly Asn Pro Lys Leu Lys Lys Gln Leu Gly Pro Gly Lys Lys Asn Asp
145                     150                     155                     160

Glu Val Ser Ser Leu Asp Ala Phe Leu Asp Leu Ile Arg Asn Leu Phe
                        165                     170                     175

Pro Glu Asn Leu Val Gln Ala Cys Phe Gln Gln Ile Gln Thr Val Thr
                        180                     185                     190

Lys Lys Val Leu Val Ala Pro Pro Asp Glu Glu Ala Asn Ala Thr
                195                     200                     205

Ser Ala Glu Val Ser Leu Leu Asn Glu Thr Val Thr Glu Val Pro Glu
    210                     215                     220

Glu Thr Lys Met Val Ile Lys Lys Gly Leu Glu Phe Lys Asp Gly Met
225                     230                     235                     240

Asn Val Leu Gly Leu Ile Gly Phe Phe Ile Ala Phe Gly Ile Ala Met
                        245                     250                     255

Gly Lys Met Gly Asp Gln Ala Lys Leu Met Val Asp Phe Phe Asn Ile
                260                     265                     270

Leu Asn Glu Ile Val Met Lys Leu Val Ile Met Ile Met Trp Tyr Ser
                275                     280                     285

Pro Leu Gly Ile Ala Cys Leu Ile Cys Gly Lys Ile Ile Ala Ile Lys
    290                     295                     300

Asp Leu Glu Val Val Ala Arg Gln Leu Gly Met Tyr Met Val Thr Val
305                     310                     315                     320

Ile Ile Gly Leu Ile Ile His Gly Gly Ile Phe Leu Pro Leu Ile Tyr
                        325                     330                     335

Phe Val Val Thr Arg Lys Asn Pro Phe Ser Leu Phe Ala Gly Ile Phe
                340                     345                     350

Gln Ala Trp Ile Thr Ala Leu Gly Thr Ala Ser Ser Ala Gly Thr Leu
                355                     360                     365

Pro Val Thr Phe Arg Cys Leu Glu Glu Asn Leu Gly Ile Asp Lys Arg
    370                     375                     380

Val Thr Arg Phe Val Leu Pro Val Gly Ala Thr Ile Asn Met Asp Gly
385                     390                     395                     400

Thr Ala Leu Tyr Glu Ala Val Ala Ala Ile Phe Ile Ala Gln Met Asn
                405                     410                     415

Gly Val Val Leu Asp Gly Gly Gln Ile Val Thr Val Ser Leu Thr Ala
                420                     425                     430
```

-continued

```
Thr Leu Ala Ser Val Gly Ala Ala Ser Ile Pro Ser Ala Gly Leu Val
            435                 440                 445
Thr Met Leu Leu Ile Leu Thr Ala Val Gly Leu Pro Thr Glu Asp Ile
    450                 455                 460
Ser Leu Val Ala Val Asp Trp Leu Leu Asp Arg Met Arg Thr Ser
465                 470                 475                 480
Val Asn Val Val Gly Asp Ser Phe Gly Ala Gly Ile Val Tyr His Leu
                485                 490                 495
Ser Lys Ser Glu Leu Asp Thr Ile Asp Ser Gln His Arg Val His Glu
                500                 505                 510
Asp Ile Glu Met Thr Lys Thr Gln Ser Ile Tyr Asp Asp Met Lys Asn
            515                 520                 525
His Arg Glu Ser Asn Ser Asn Gln Cys Val Tyr Ala Ala His Asn Ser
        530                 535                 540
Val Ile Val Asp Glu Cys Lys Val Thr Leu Ala Ala Asn Gly Lys Ser
545                 550                 555                 560
Ala Asp Cys Ser Val Glu Glu Glu Pro Trp Lys Arg Glu Lys
                565                 570
```

(2) INFORMATION FOR SEQ ID NO:8:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..15

(ix) FEATURE:
        (A) NAME/KEY: CDS
        (B) LOCATION: 16..1590

(ix) FEATURE:
        (A) NAME/KEY: 3'UTR
        (B) LOCATION: 1591..1674

(xi) SEQUENCE DESCRIPTION: SEQ ID NO:8:

```
ATAGCGGCGA CAGCC ATG GGG AAA CCG GCG AGG AAA GGA TGC CCG AGT TGG         51
              Met Gly Lys Pro Ala Arg Lys Gly Cys Pro Ser Trp
                1               5                  10

AAG CGC TTC CTG AAG AAT AAC TGG GTG TTG CTG TCC ACC GTG GCC GCG          99
Lys Arg Phe Leu Lys Asn Asn Trp Val Leu Leu Ser Thr Val Ala Ala
         15                  20                  25

GTG GTG CTA GGC ATT ACC ACA GGA GTC TTG GTT CGA GAA CAC AGC AAC         147
Val Val Leu Gly Ile Thr Thr Gly Val Leu Val Arg Glu His Ser Asn
 30                  35                  40

CTC TCA ACT CTA GAG AAA TTC TAC TTT GCT TTT CCT GGA GAA ATT CTA         195
Leu Ser Thr Leu Glu Lys Phe Tyr Phe Ala Phe Pro Gly Glu Ile Leu
 45                  50                  55                  60

ATG CGG ATG CTG AAA CTC ATC ATT TTG CCA TTA ATA TCC AGC ATG             243
Met Arg Met Leu Lys Leu Ile Ile Leu Pro Leu Ile Ile Ser Ser Met
             65                  70                  75

ATT ACA GGT GTT GCT GCA CTG GAT TCC AAC GTA TCC GGA AAA ATT GGT         291
Ile Thr Gly Val Ala Ala Leu Asp Ser Asn Val Ser Gly Lys Ile Gly
                 80                  85                  90

CTG CGC GCT GTC GTG TAT TAT TTC TGT ACC ACT CTC ATT GCT GTT ATT         339
Leu Arg Ala Val Val Tyr Tyr Phe Cys Thr Thr Leu Ile Ala Val Ile
```

-continued

| | | | | | | | | | | | | | | | |
|---|---|---|---|---|---|---|---|---|---|---|---|---|---|---|---|
| | | | 95 | | | | | 100 | | | | | 105 | | |
| CTA | GGT | ATT | GTG | CTG | GTG | GTG | AGC | ATC | AAG | CCT | GGT | GTC | ACC | CAG | AAA | 387 |
| Leu | Gly | Ile | Val | Leu | Val | Val | Ser | Ile | Lys | Pro | Gly | Val | Thr | Gln | Lys | |
| | 110 | | | | 115 | | | | | 120 | | | | | | |
| GTG | GGT | GAA | ATT | GCG | AGG | ACA | GGC | AGC | ACC | CCT | GAA | GTC | AGT | ACG | GTG | 435 |
| Val | Gly | Glu | Ile | Ala | Arg | Thr | Gly | Ser | Thr | Pro | Glu | Val | Ser | Thr | Val | |
| 125 | | | | | 130 | | | | | 135 | | | | | 140 | |
| GAT | GCC | ATG | TTA | GAT | CTC | ATC | AGG | AAT | ATG | TTC | CCT | GAG | AAT | CTT | GTC | 483 |
| Asp | Ala | Met | Leu | Asp | Leu | Ile | Arg | Asn | Met | Phe | Pro | Glu | Asn | Leu | Val | |
| | | | | 145 | | | | | 150 | | | | | 155 | | |
| CAG | GCC | TGT | TTT | CAG | CAG | TAC | AAA | ACT | AAG | CGT | GAA | GAA | GTG | AAG | CCT | 531 |
| Gln | Ala | Cys | Phe | Gln | Gln | Tyr | Lys | Thr | Lys | Arg | Glu | Glu | Val | Lys | Pro | |
| | | | 160 | | | | | 165 | | | | | 170 | | | |
| CCC | AGC | GAT | CCA | GAG | ATG | AAC | ATG | ACA | GAA | GAG | TCC | TTC | ACA | GCT | GTC | 579 |
| Pro | Ser | Asp | Pro | Glu | Met | Asn | Met | Thr | Glu | Glu | Ser | Phe | Thr | Ala | Val | |
| | | | 175 | | | | | 180 | | | | | 185 | | | |
| ATG | ACA | ACT | GCA | ATT | TCC | AAG | AAC | AAA | ACA | AAG | GAA | TAC | AAA | ATT | GTT | 627 |
| Met | Thr | Thr | Ala | Ile | Ser | Lys | Asn | Lys | Thr | Lys | Glu | Tyr | Lys | Ile | Val | |
| | 190 | | | | 195 | | | | | 200 | | | | | | |
| GGC | ATG | TAT | TCA | GAT | GGC | ATA | AAC | GTC | CTG | GGC | TTG | ATT | GTC | TTT | TGC | 675 |
| Gly | Met | Tyr | Ser | Asp | Gly | Ile | Asn | Val | Leu | Gly | Leu | Ile | Val | Phe | Cys | |
| 205 | | | | | 210 | | | | | 215 | | | | | 220 | |
| CTT | GTC | TTT | GGA | CTT | GTC | ATT | GGA | AAA | ATG | GGA | GAA | AAG | GGA | CAA | ATT | 723 |
| Leu | Val | Phe | Gly | Leu | Val | Ile | Gly | Lys | Met | Gly | Glu | Lys | Gly | Gln | Ile | |
| | | | | 225 | | | | | 230 | | | | | 235 | | |
| CTG | GTG | GAT | TTC | TTC | AAT | GCT | TTG | AGT | GAT | GCA | ACC | ATG | AAA | ATC | GTT | 771 |
| Leu | Val | Asp | Phe | Phe | Asn | Ala | Leu | Ser | Asp | Ala | Thr | Met | Lys | Ile | Val | |
| | | | 240 | | | | | 245 | | | | | 250 | | | |
| CAG | ATC | ATC | ATG | TGT | TAT | ATG | CCA | CTA | GGT | ATT | TTG | TTC | CTG | ATT | GCT | 819 |
| Gln | Ile | Ile | Met | Cys | Tyr | Met | Pro | Leu | Gly | Ile | Leu | Phe | Leu | Ile | Ala | |
| | | 255 | | | | | 260 | | | | | 265 | | | | |
| GGG | AAG | ATC | ATA | GAA | GTT | GAA | GAC | TGG | GAA | ATA | TTC | CGC | AAG | CTG | GGC | 867 |
| Gly | Lys | Ile | Ile | Glu | Val | Glu | Asp | Trp | Glu | Ile | Phe | Arg | Lys | Leu | Gly | |
| | 270 | | | | 275 | | | | | 280 | | | | | | |
| CTT | TAC | ATG | GCC | ACA | GTC | CTG | ACT | GGG | CTT | GCA | ATC | CAC | TCC | ATT | GTA | 915 |
| Leu | Tyr | Met | Ala | Thr | Val | Leu | Thr | Gly | Leu | Ala | Ile | His | Ser | Ile | Val | |
| 285 | | | | | 290 | | | | | 295 | | | | | 300 | |
| ATT | CTC | CCG | CTG | ATA | TAT | TTC | ATA | GTC | GTA | CGA | AAG | AAC | CCT | TTC | CGA | 963 |
| Ile | Leu | Pro | Leu | Ile | Tyr | Phe | Ile | Val | Val | Arg | Lys | Asn | Pro | Phe | Arg | |
| | | | | 305 | | | | | 310 | | | | | 315 | | |
| TTT | GCC | ATG | GGA | ATG | GCC | CAG | GCT | CTC | CTG | ACA | GCT | CTC | ATG | ATC | TCT | 1011 |
| Phe | Ala | Met | Gly | Met | Ala | Gln | Ala | Leu | Leu | Thr | Ala | Leu | Met | Ile | Ser | |
| | | | 320 | | | | | 325 | | | | | 330 | | | |
| TCC | AGT | TCA | GCA | ACA | CTG | CCT | GTC | ACC | TTC | CGC | TGT | GCT | GAA | GAA | AAT | 1059 |
| Ser | Ser | Ser | Ala | Thr | Leu | Pro | Val | Thr | Phe | Arg | Cys | Ala | Glu | Glu | Asn | |
| | | 335 | | | | | 340 | | | | | 345 | | | | |
| AAC | CAG | GTG | GAC | AAG | AGG | ATC | ACT | CGA | TTC | GTG | TTA | CCC | GTT | GGT | GCA | 1107 |
| Asn | Gln | Val | Asp | Lys | Arg | Ile | Thr | Arg | Phe | Val | Leu | Pro | Val | Gly | Ala | |
| | 350 | | | | 355 | | | | | 360 | | | | | | |
| ACA | ATC | AAC | ATG | GAT | GGG | ACC | GCG | CTC | TAT | GAA | GCA | GTG | GCA | GCG | GTG | 1155 |
| Thr | Ile | Asn | Met | Asp | Gly | Thr | Ala | Leu | Tyr | Glu | Ala | Val | Ala | Ala | Val | |
| 365 | | | | | 370 | | | | | 375 | | | | | 380 | |
| TTT | ATT | GCA | CAG | TTG | AAT | GAC | CTG | GAC | TTG | GGC | ATT | GGG | CAG | ATC | ATC | 1203 |
| Phe | Ile | Ala | Gln | Leu | Asn | Asp | Leu | Asp | Leu | Gly | Ile | Gly | Gln | Ile | Ile | |
| | | | | 385 | | | | | 390 | | | | | 395 | | |
| ACC | ATC | AGT | ATC | ACG | GCC | ACA | TCT | GCC | AGC | ATC | GGA | GCT | GCT | GGC | GTG | 1251 |
| Thr | Ile | Ser | Ile | Thr | Ala | Thr | Ser | Ala | Ser | Ile | Gly | Ala | Ala | Gly | Val | |
| | | | 400 | | | | | 405 | | | | | 410 | | | |
| CCC | CAG | GCT | GGC | CTG | GTG | ACC | ATG | GTG | ATT | GTG | CTG | AGT | GCC | GTG | GGC | 1299 |

```
Pro Gln Ala Gly Leu Val Thr Met Val Ile Val Leu Ser Ala Val Gly
        415                 420                 425

CTG CCC GCC GAG GAT GTC ACC CTG ATC ATT GCT GTC GAC TGG CTC CTG    1347
Leu Pro Ala Glu Asp Val Thr Leu Ile Ile Ala Val Asp Trp Leu Leu
    430                 435                 440

GAC CGG TTC AGG ACC ATG GTC AAC GTC CTT GGT GAT GCT TTT GGG ACG    1395
Asp Arg Phe Arg Thr Met Val Asn Val Leu Gly Asp Ala Phe Gly Thr
445                 450                 455                 460

GGC ATT GTG GAA AAG CTC TCC AAG AAG GAG CTG GAG CAG ATG GAT GTT    1443
Gly Ile Val Glu Lys Leu Ser Lys Lys Glu Leu Glu Gln Met Asp Val
                465                 470                 475

TCA TCT GAA GTC AAC ATT GTG AAT CCC TTT GCC TTG GAA TCC ACA ATC    1491
Ser Ser Glu Val Asn Ile Val Asn Pro Phe Ala Leu Glu Ser Thr Ile
            480                 485                 490

CTT GAC AAC GAA GAC TCA GAC ACC AAG AAG TCT TAT GTC AAT GGA GGC    1539
Leu Asp Asn Glu Asp Ser Asp Thr Lys Lys Ser Tyr Val Asn Gly Gly
        495                 500                 505

TTT GCA GTA GAC AAG TCT GAC ACC ATC TCA TTC ACC CAG ACC TCA CAG    1587
Phe Ala Val Asp Lys Ser Asp Thr Ile Ser Phe Thr Gln Thr Ser Gln
510                 515                 520

TTC TAGGGCCCCT GGCTGCAGAT GACTGGAAAC AAGGAAGGAC ATTTCGTGAG         1640
Phe
525

AGTCATCTCA AACACGGCTT AAGGAAAAGA GAAA                              1674

(2) INFORMATION FOR SEQ ID NO:9:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:9:

Met Gly Lys Pro Ala Arg Lys Gly Cys Pro Ser Trp Lys Arg Phe Leu
1               5                   10                  15

Lys Asn Asn Trp Val Leu Leu Ser Thr Val Ala Ala Val Val Leu Gly
            20                  25                  30

Ile Thr Thr Gly Val Leu Val Arg Glu His Ser Asn Leu Ser Thr Leu
        35                  40                  45

Glu Lys Phe Tyr Phe Ala Phe Pro Gly Glu Ile Leu Met Arg Met Leu
    50                  55                  60

Lys Leu Ile Ile Leu Pro Leu Ile Ile Ser Ser Met Ile Thr Gly Val
65                  70                  75                  80

Ala Ala Leu Asp Ser Asn Val Ser Gly Lys Ile Gly Leu Arg Ala Val
                85                  90                  95

Val Tyr Tyr Phe Cys Thr Thr Leu Ile Ala Val Ile Leu Gly Ile Val
            100                 105                 110

Leu Val Val Ser Ile Lys Pro Gly Val Thr Gln Lys Val Gly Glu Ile
        115                 120                 125

Ala Arg Thr Gly Ser Thr Pro Glu Val Ser Thr Val Asp Ala Met Leu
    130                 135                 140

Asp Leu Ile Arg Asn Met Phe Pro Glu Asn Leu Val Gln Ala Cys Phe
145                 150                 155                 160

Gln Gln Tyr Lys Thr Lys Arg Glu Glu Val Lys Pro Pro Ser Asp Pro
                165                 170                 175

Glu Met Asn Met Thr Glu Glu Ser Phe Thr Ala Val Met Thr Thr Ala
```

-continued

```
               180                 185                 190
Ile Ser Lys Asn Lys Thr Lys Glu Tyr Lys Ile Val Gly Met Tyr Ser
        195                 200                 205
Asp Gly Ile Asn Val Leu Gly Leu Ile Val Phe Cys Leu Val Phe Gly
210                 215                 220
Leu Val Ile Gly Lys Met Gly Glu Lys Gly Gln Ile Leu Val Asp Phe
225                 230                 235                 240
Phe Asn Ala Leu Ser Asp Ala Thr Met Lys Ile Val Gln Ile Ile Met
                245                 250                 255
Cys Tyr Met Pro Leu Gly Ile Leu Phe Leu Ile Ala Gly Lys Ile Ile
                260                 265                 270
Glu Val Glu Asp Trp Glu Ile Phe Arg Lys Leu Gly Leu Tyr Met Ala
                275                 280                 285
Thr Val Leu Thr Gly Leu Ala Ile His Ser Ile Val Ile Leu Pro Leu
                290                 295                 300
Ile Tyr Phe Ile Val Val Arg Lys Asn Pro Phe Arg Phe Ala Met Gly
305                 310                 315                 320
Met Ala Gln Ala Leu Leu Thr Ala Leu Met Ile Ser Ser Ser Ser Ala
                325                 330                 335
Thr Leu Pro Val Thr Phe Arg Cys Ala Glu Glu Asn Asn Gln Val Asp
                340                 345                 350
Lys Arg Ile Thr Arg Phe Val Leu Pro Val Gly Ala Thr Ile Asn Met
                355                 360                 365
Asp Gly Thr Ala Leu Tyr Glu Ala Val Ala Ala Val Phe Ile Ala Gln
                370                 375                 380
Leu Asn Asp Leu Asp Leu Gly Ile Gly Gln Ile Ile Thr Ile Ser Ile
385                 390                 395                 400
Thr Ala Thr Ser Ala Ser Ile Gly Ala Ala Gly Val Pro Gln Ala Gly
                405                 410                 415
Leu Val Thr Met Val Ile Val Leu Ser Ala Val Gly Leu Pro Ala Glu
                420                 425                 430
Asp Val Thr Leu Ile Ile Ala Val Asp Trp Leu Leu Asp Arg Phe Arg
                435                 440                 445
Thr Met Val Asn Val Leu Gly Asp Ala Phe Gly Thr Gly Ile Val Glu
                450                 455                 460
Lys Leu Ser Lys Lys Glu Leu Glu Gln Met Asp Val Ser Ser Glu Val
465                 470                 475                 480
Asn Ile Val Asn Pro Phe Ala Leu Glu Ser Thr Ile Leu Asp Asn Glu
                485                 490                 495
Asp Ser Asp Thr Lys Lys Ser Tyr Val Asn Gly Gly Phe Ala Val Asp
                500                 505                 510
Lys Ser Asp Thr Ile Ser Phe Thr Gln Thr Ser Gln Phe
                515                 520                 525
```

(2) INFORMATION FOR SEQ ID NO:10:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:10:

CGCGGGTACC GCCATGGAGA AGAGCAAC                                               28

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCGTCTAGA TCACAGAACC GACTCCTTG                            29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCGGGTACC AATATGACTA AAAGCAATG                            29

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGTCTAGA CTACATCTTG GTTTCACTG                            29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGGTACC ACCATGGCAT CTACGGAAG                            29

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGCGTCTAGA TTATTTCTCA CGTTTCCAAG                            30

(2) INFORMATION FOR SEQ ID NO:16:

-continued

```
    (i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:16:

CGCGGGTACC GCCATGGGGA AACCGGCG                                              28

(2) INFORMATION FOR SEQ ID NO:17:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:17:

CGCGGGATCC CTAGAACTGT GAGGTCTG                                              28
```

AMINO ACID TRANSPORTERS AND USES

This application is a divisional of U.S. Ser. No. 09/042,929, filed Mar. 17, 1998, which is a divisional of U.S. Ser. No. 08/546,666, filed Oct. 23, 1995, now U.S. Pat. No. 5,776,774, which is a divisional of U.S. Ser. No. 08/140,729, filed Oct. 20, 1993, now U.S. Pat. No. 5,658,782, issued Aug. 19, 1997. The disclosures of each of these prior applications are considered as being part of the disclosure of the application and are explicitly incorporated by reference herein.

This invention was made with government support under National Institute of Health grants DA07595 and DA03160. The government has certain rights to this invention.

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding each of four novel human amino acid transporter genes. The invention also relates to the construction of recombinant expression constructs comprising such cDNAs from each of the four novel himan amino acid transporter genes of the invention, said recombinant expression constructs being capable of expressing amino acid transporter proteins in cultures of transformed prokaryotic and eukaryotic cells. Production of the transporter proteins in such cultures is also provided. The invention relates to the use of such cultures of such transformed cells to produce homogeneous compositions of each transporter protein. The invention also provides cultures of such cells producing transporter proteins for the characterization of novel and useful drugs. Antibodies against and epitopes of these transporter proteins are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain (see Nicholls & Attwell, 1990, TiPS 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, Nature 360: 464467).

Glutamate is one example of such an amino acid. Glutamate is an excitatory neurotransmitter (i.e., excitatory neurons use glutamate as a neurotransmitter). When present in excess (>about 300 $\mu$M; Bouvier et al., 1992, Nature 360: 471–474; Nicholls & Attwell, ibid.; >5 $\mu$M for 5 min.; Choi et al., 1987, J. Neurosci. 7: 357–358), extracellular glutamate causes neuronal cell death. Glutamate transporters play a pivotal role in maintaining non-toxin extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke, anoxia and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptimal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen el al., 1967, J. Biol. Chem. 242: 5237–5246 report the discovery of a neutral amino acid transporter (termed the ACS transporter) in Erlich ascites tumor cells.

Makowske & Christensen, 1982, J. Biol. Chem. 257: 14635–14638 provide a biochemical characterization of hepatic amino acid transport.

Kanner & Schuldiner, 1987, CRC Crit. Rev. Biochem. 22: 1–38 provide a review of the biochemistry of neurotransmitters.

Olney et al., 1990, Science 248: 596–599 disclose that the amino acid cysteine is a neurotoxin when present in excess extracellularly.

Wallace et al., 1990, J. Bacteriol. 172: 3214–3220 report the cloning and sequencing of a glutamate/aspartate transporter gene termed gltP from *Escherichia coli* strain K12.

Kim et al., 1991, Nature 352: 725–728 report the discovery that a cationic amino acid transporter is the cell surface target for infection by ecotropic retroviruses in mice.

Wang et al., 1991, Nature 352: 729–731 report the discovery that a cationic amino acid transporter is the cell surface target for infection by ecotropic retroviruses in mice.

Maenz et al., 1992, J. Biol. Chem. 267: 1510–1516 provide a biochemical characterization of amino acid transport in rabbit jejunal brush border membranes.

Bussolati et al., 1992, J. Biol. Chem. 267: 8330–8335 report that the ASC transporter acts in an electrochemically neutral manner so that sodium ion co-transport occurs without disrupting the normal membrane potential of the cells expressing the transporter.

Engelke et al., 1992, J. Bacteriol. 171: 5551–5560 report the cloning of a dicarboxylate carrier from *Rhiwzobium meliloti*.

Guastella et al., 1992, Proc. Nati. Acad. Sci. USA 89: 7189–7193 disclose the cloning of a sodium ion and chloride ion-dependent glycine transporter from a glioma cell line that is expressed in the rat forebrain and cerebellum.

Kavanaugh et al., 1992, J. Biol. Chem. 267: 22007–22009 report that biochemical characterization of a rat brain GABA transporter expressed in vitro in *Xenopus laevis* oocytes.

Storck et al., 1992, Proc. Nad. Acad. Sci. USA 89: 10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, Nature 360: 467–471 disclose the cloning and sequencing of a sodium ion-dependent, high affinity glutamate transporter from rabbit small intestine termed EAAC1.

Kong et al., 1993, J. Biol. Chem. 268: 1509–1512 report the cloning and sequencing of a sodium-ion dependent neutral amino acid transporter of the A type that is homologous to a sodium-ion dependent glucose transporter.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids, each nucleic acid having a nucleotide sequence of a novel amino acid transporter gene. The nucleic acids provided by the invention each comprise a complementary DNA (cDNA) copy of the corresponding mRNA transcribed in vivo from each of the amino acid transporter genes of the invention. Also provided are the deduced amino acid sequences of each the cognate proteins of the cDNAs provided by the invention.

This invention provides nucleic acids, nucleic acid hybridization probes, recombinant eukaryotic expression constructs capable of expressing the amino acid transporters of the invention in cultures of transformed cells, such cultures of transformed eukaryotic cells that synthesize the amino acid transporters of the invention, homogeneous compositions of each of the amino acid transporter proteins, and antibodies against and epitopes of each of the amino acid transporter proteins of the invention. Methods for characterizing these transporter proteins and methods for using these proteins in the development of agents having pharmacological uses related to these transporter proteins are also provided by the invention.

In a first aspect, the invention provides a nucleic acid having a nucleotide sequence encoding a human neutral amino acid transporter that is the ASCT1 transporter (SEQ ID No:2). In this embodiment of the invention, the nucleotide sequence includes 1680 nucleotides of the human ASCT1 cDNA comprising 1596 nucleotides of coding sequence, 30 nucleotides of 5' untranslated sequence and 54 nucleotides of 3' untranslated sequence. In this embodiment of the invention, the nucleotide sequence of the ASCT1 transporter consists essentially of the nucleotide sequence depicted in FIG. 1 (SEQ ID No:2). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding ASCT1 disclosed herein.

The corresponding ASCT1 protein molecule, having the deduced amino acid sequence consisting essentially of the sequence shown in FIG. 1 (SEQ ID No.:3), is also claimed as an aspect of the invention. The use of the term "consisting essentially of" herein is as described above. Similarly, the corresponding ASCT1 protein molecule, having the deduced amino acid sequence consisting essentially of the sequence shown in FIG. 1 (SEQ ID No.:3), is also claimed as an aspect of the invention. ASCT1 protein molecules provided by the invention are understood to have substantially the same biological properties as the ASCT1 protein molecule encoded by the nucleotide sequence described herein.

In another aspect, the invention comprises a homogeneous composition of the 55.9 kD mammalian ASCT1 transporter or derivative thereof, said size being understood to be the size of the protein before any post-translational modifications thereof. The amino acid sequence of the ASCT1 transporter or derivative thereof preferably consists essentially of the amino acid sequence of the human ASCT1 transporter protein shown in FIG. 1 (SEQ ID No:3).

In a second aspect, the invention provides a nucleic acid having a nucleotide sequence encoding a human excitatory amino acid transporter that is the EAAT1 transporter (SEQ ID No:4). In this embodiment of the invention, the nucleotide sequence includes 1680 nucleotides of the human EAAT1 cDNA comprising 1626 nucleotides of coding sequence, 30 nucleotides of 5' untranslated sequence and 24 nucleotides of 3' untranslated sequence. In this embodiment of the invention, the nucleotide sequence of the EAAT1 transporter consists essentially of the nucleotide sequence depicted in FIG. 2 (SEQ ID No:4). The use of the term "consisting essentially of" herein is as described above.

In another aspect, the invention comprises a homogeneous composition of the 59.5 kilodalton (kD) mammalian EAAT1 transporter or derivative thereof, said size being understood to be the size of the protein before any post-translational modifications thereof. The amino acid sequence of the EAAT1 transporter or derivative thereof preferably consists essentially of the amino acid sequence of the human EAAT1 transporter protein shown in FIG. 2 (SEQ ID No:5). EAAT1 protein molecules provided by the invention are understood to have substantially the same biological properties as the EAAT1 protein molecule encoded by the nucleotide sequence described herein.

In a third aspect, the invention provides a nucleic acid having a nucleotide sequence encoding a human excitatory amino acid transporter that is the EAAT2 transporter (SEQ ID No:6). In this embodiment of the invention, the nucleotide sequence includes 1800 nucleotides of the human EAAT2 cDNA comprising 1722 nucleotides of coding sequence, 33 nucleotides of 5' untranslated sequence and 45 nucleotides of 3' untranslated sequence. In this embodiment of the invention, the nucleotide sequence of the EAAT2 transporter consists essentially of the nucleotide sequence depicted in FIG. 3 (SEQ ID No:6). The use of the term "consisting essentially of" herein is as described above.

The corresponding EAAT2 protein molecule, having the deduced amino acid sequence consisting essentially of the sequence shown in FIG. 3 (SEQ ID No.:7), is also claimed as an aspect of the invention. EAAT2 protein molecules provided by the invention are understood to have substantially the same biological properties as the EAAT2 protein molecule encoded by the nucleotide sequence described herein.

In another aspect, the invention comprises a homogeneous composition of the 62.1 kD mammalian EAAT2 transporter or derivative thereof, said size being understood to be the size of the protein before any post-translational modifications thereof. The amino acid sequence of the EAAT2 transporter or derivative thereof preferably consists essentially of the amino acid sequence of the human EAAT2 transporter protein shown in FIG. 3 (SEQ ID No:7).

In yet another aspect, the invention provides a nucleic acid having a nucleotide sequence encoding a human excitatory amino acid transporter that is the EAAT3 transporter (SEQ ID No:8). In this embodiment of the invention, the nucleotide sequence includes 1674 nucleotides of the human EAAT3 cDNA comprising 1575 nucleotides of coding sequence, 15 nucleotides of 5' untranslated sequence and 84 nucleotides of 3' untranslated sequence. In this embodiment of the invention, the nucleotide sequence of the EAAT3 transporter consists essentially of the nucleotide sequence depicted in FIG. 4 (SEQ ID No:8). The use of the term "consisting essentially of" herein is as described above.

The corresponding EAAT3 protein molecule, having the deduced amino acid sequence consisting essentially of the sequence shown in FIG. 4 (SEQ ID No.:9), is also claimed as an aspect of the invention. EAAT3 protein molecules provided by the invention are understood to have substantially the same biological properties as the EAAT3 protein molecule encoded by the nucleotide sequence described herein.

In another aspect, the invention comprises a homogeneous composition of the 57.2 kD mammalian EAAT3 transporter or derivative thereof, said size being understood to be the size of the protein before any post-translational modifications thereof. The amino acid sequence of the EAAT3 transporter or derivative thereof preferably consists essentially of the amino acid sequence of the human EAAT3 transporter protein shown in FIG. 4 (SEQ ID No:9).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of these transporter genes in various tissues of mammals, including humans. It is also an object of the present invention to provide nucleic acid hybridization probes derived from the sequences of the amino acid transporter genes of the invention to be used for the detection and diagnosis of genetic diseases. It is an object of this invention to provide nucleic acid hybridization probes derived from the DNA sequences of the amino acid transporter genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporters of the invention. It is a particular object to provide monoclonal antibodies against these amino acid transporters, must preferably the human excitatory and neutral amino acid transporters as herein disclosed. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of an amino acid transporter of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the amino acid transporters of the invention. Chimeric antibodies immunologically reactive against the amino acid transporter proteins of the invention are also within the scope of this invention.

The present invention provides recombinant expression constructs comprising a nucleic acid encoding an amino acid transporter of the invention wherein the construct is capable of expressing the encoded amino acid transporter in cultures of cells transformed with the construct. Preferred embodiments of such constructs comprise the human EAAT1 cDNA (SEQ ID No.:4), the human EAAT2 cDNA (SEQ ID No.:6), the human EAAT3 cDNA (SEQ ID No.:8), and human ASCT1 cDNA (SEQ ID No.:2), each construct being capable of expressing the amino acid transporter encoded therein in cells transformed with the construct.

The invention also provides cultures cells transformed with the recombinant expression constructs of the invention, each such cultures being capable of and in fact expressing the amino acid transporter encoded in the transforming construct.

The present invention also includes within its scope protein preparations of prokaryotic and eukaryotic cell membranes containing at least one of the amino acid transporter proteins of the invention, derived from cultures of prokaryotic or eukaryotic cells, respectively, transformed with the recombinant expression constructs of the invention. In a preferred embodiment, each preparation of such cell membranes comprises one species of the amino acid transporter proteins of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells transformed with a recombinant expression construct of the invention are contacted with such a compound, and the effect of the compound on the transport of the appropriate amino acid is assayed. Additional preferred embodiments comprise quantitative analyses of such effects.

The present invention is also useful for the detection of analogues, agonists or antagonists, known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A–1E illustrates the nucleotide (SEQ ID No.:2) and amino acid (SEQ ID No.:3) sequences of the human ASCT1 neutral amino acid transporter.

FIGS. 2A–2E illustrates the nucicotide (SEQ ID No.:4) and amino acid (SEQ ID No.:5) sequences of the human EAAT1 excitatory amino acid transporter.

FIGS. 3A–3F illustrates the nucleotide (SEQ ID No.:6) and amino acid (SEQ ID No.:7) sequences of the human EAAT2 excitatory amino acid transporter.

FIGS. 4A–4E illustrates the nucleotide (SEQ ID No.:8) and amino acid (SEQ ID No.:9) sequences of the human EAAT3 excitatory amino acid transporter.

FIGS. 5A & 5B presents an amino acid sequence comparison between human ASCT1, GLAST 1, GLT1 and EAAC1.

FIGS. 8A–8C represents the pharmacological responsiveness of glutamate transport by the human excitatory amino acid transporters EAAT1, EAAT2 and EAAT3 when contacted with the indicated competitors/inhibitors 1 $\mu$L-glutamate and inhibitor/competitor concentrations of 3 $\mu$M, 100 $\mu$M or 3 mM at the indicated concentrations.

FIGS. 11A and 11B illustrates the degree of predicted amino acid sequence homology between the novel human glutamate transporters EAAT1, EAAT2 and EAAT3; overbars indicate nine regions of hydrophobicity determined using the algorithm of Eisenberg et al., and potential sites of N-linked glycosylation are shown by the circled asparagine (N) residues.

FIGS. 12A through 12C illustrate electrogenic uptake of various amino acids (FIG. 12A) and the concentration dependence of such uptake of L-glutamate (FIGS. 12B and 12C) in *Xenopus laevis* oocytes expressing the EAAT1 amino acid transporter.

DETAILED DESCRIPTION OF THE PREFERRED EMBODIMENTS

Figure 6A:
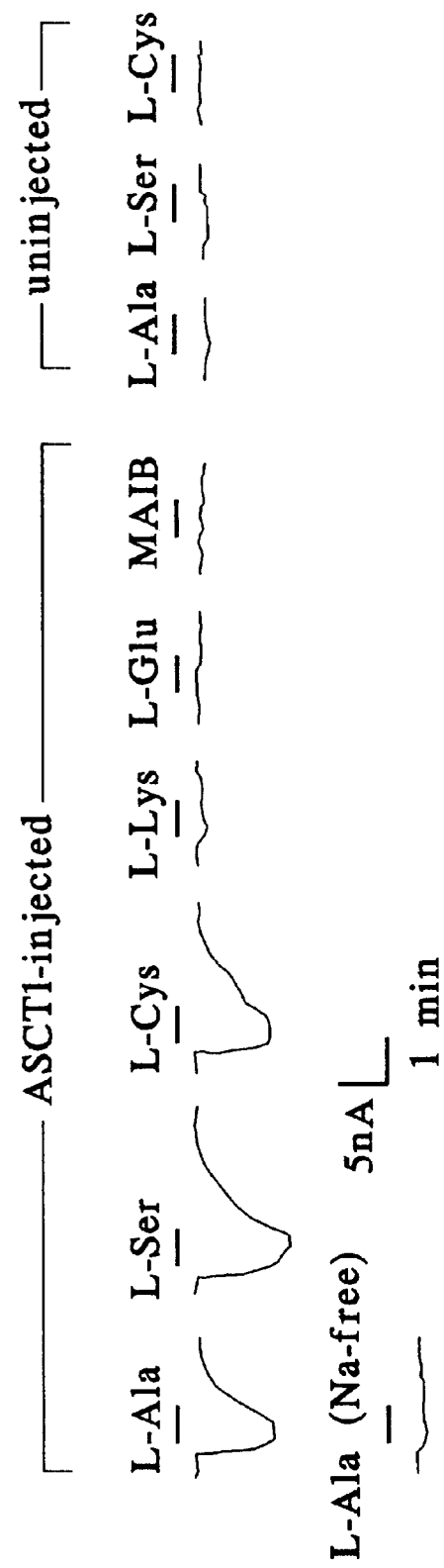
FIGS. 6A–6C illustrates transmembrane electrochemical currents in *Xenopus laevis* oocytes microinjected with RNA encoding ASCT1 and contacted with the indicated amino acids (FIG. 6A); the amino acid concentration dependence of such electrochemical currents (FIG. 6B); and a plot of normalized current vs. amino acid concentration illustrating the kinetic parameters of amino acid transport (FIG. 6C).

The term "human amino acid transporter EAAT1" as used herein refers to proteins consisting essentially of, and having substantially the same biological activity as, the protein encoded by the nucleic acid depicted in FIGS. 2A–2E (SEQ ID No.:4). This definition is intended to encompass natural allelic variations in the EAAT1 sequence. Cloned nucleic acid provided by the present invention may encode EAAT1 protein of any species of origin, including, for example, mouse, rat, rabbit, cat, and human, but preferably the nucleic acid provided by the invention encodes EAAT1 receptors of mammalian, most preferably human, origin.

The term "human amino acid transporter EAAT2" as used herein refers to proteins consisting essentially of, and having substantially the same biological activity as, the protein encoded by the nucleic acid depicted in FIGS. 3A–3F (SEQ ID No.:6). This definition is intended to encompass natural allelic variations in the EAAT2 sequence. Cloned nucleic acid provided by the present invention may encode EAAT2 protein of any species of origin, including, for example, mouse, rat, rabbit, cat, and human, but preferably the nucleic acid provided by the invention encodes EAAT2 receptors of mammalian, most preferably human, origin.

The term "human amino acid transporter EAAT3" as used herein refers to proteins consisting essentially of, and having substantially the same biological activity as, the protein encoded by the nucleic acid depicted in FIGS. 4A–4E (SEQ ID No.:8). This definition is intended to encompass natural allelic variations in the EAAT3 sequence. Cloned nucleic acid provided by the present invention may encode EAAT3 protein of any species of origin, including, for example, mouse, rat, rabbit, cat, and human, but preferably the nucleic acid provided by the invention encodes EAAT3 receptors of mammalian, most preferably human, origin.

The term "human amino acid transporter ASCT1" as used herein refers to proteins consisting essentially of, and having substantially the same biological activity as, the protein encoded by the nucleic acid depicted in FIGS. 1A–1E (SEQ ID No.:2). This definition is intended to encompass natural allelic variations in the ASCT1 sequence. Cloned nucleic acid provided by the present invention may encode ASCT1 protein of any species of origin, including, for example, mouse, rat, rabbit, cat, and human, but preferably the nucleic acid provided by the invention encodes ASCT1 receptors of mammalian, most preferably human, origin.

Each of the nucleic acid hybridization probes provided by the invention comprise DNA or RNA consisting essentially of the nucleotide sequence of one of the amino acid transporters, depicted in FIGS. 1A through 1E, FIGS. 2A through 2E, FIGS. 3A through 3F and FIGS. 4A through 4E (SEQ ID Nos.:2,4,6,8), or any portion thereof effective in nucleic acid hybridization. Mixtures of such nucleic acid hybridization probes are also within the scope of this embodiment of the invention. Nucleic acid probes as provided herein are useful for detecting amino acid transporter gene expression in cells and tissues using techniques well-known in the art, including but not limited to Northern blot hybridization, in situ hybridization and Southern hybridization to reverse transcriptase—polymerase chain reaction product DNAs. The A probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and 4,683,202 to Mullis.

Each of the amino acid transporter proteins may be synthesized in host cells transformed with a recombinant expression construct comprising a nucleic acid encoding the particular amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, J. Biol. Chem. 264: 8222–8229). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182). Transformed host cells may express the amino acid transporter protein, but host cells transformed for purposes of cloning or amplifying nucleic acid hybridization probe DNA need not express the transporter. When expressed, each of the amino acid transporters of the invention will typically be located in the host cell membrane. See, Sambrook et al., ibid.

Cultures of cells derived from multicellular organisms are a desirable host for recombinant amino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. COS-7 cells are preferred.

The invention provides homogeneous compositions of each of the human EAAT1, EAAT2, EAAT3 and ASCT1 amino acid transporter proteins produced by transformed eukaryotic cells as provided herein. Each such homogeneous composition is intended to be comprised of the corresponding amino acid transporter protein that comprises at least 90% of the protein in such a homogenous composition. The invention also provides membrane preparation from cells expressing each of the amino acid transporter proteins as the result of transformation with a recombinant expression construct, as described herein.

Amino acid transporter proteins made from cloned genes in accordance with the present invention may be used for screening amino acid analogues, or agonist or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a particular amino acid transporter, pure preparations of membranes containing the transporter can be obtained.

The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter proteins or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter proteins of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses one of the amino acid transporters provided by the invention, or any cell or cell line that expresses one of the amino acid transporters of the invention, or any epitope thereof, as a result of molecular or genetic engineering, or that has been treated to increase the expression of an endogenous or heterologous amino acid transporter protein by physical, biochemical or genetic means. Preferred cells are *E. coli* and insect SF9 cells, most preferably *E. coli* cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balbic mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Human Neutral Amino Acid Transporter cDNA

In order to clone a novel human neutral amino acid transporter, a cDNA library was prepared from human motor cortex mRNA using standard techniques [see Sambrook et al., 1990, *Molecular Cloning: A Laboratory Manual* (Cold Spring Harbor Press: New York)]. Briefly, total RNA was isolated using the method of Chomczynski & Sacchi (1987, Anal. Biochem. 162: 156–159), wherein the tissue is disrupted and solubilized in a solution containing guanidinium isothiocyanate and the RNA purified by phenol/chloroform extractions. Total cellular RNA thus isolated was then enriched for poly ($A^+$) mRNA by oligo (dT) chromatography. A mixture of oligo (dT)-primed and random-primed mRNA was converted to cDNA using the Superscript Choice System (Bethesda Research Labs, Gaithersburg, Md.). cDNA was ligated into the cloning vector λZAPII (Strategene, La Jolla, Calif.), packaged into phage heads using commercially-available packaging extracts (Strategene) and used to infect *E. coli*. Lawns of infected bacterial cells were used to make plaque lifts for hybridization using standard conditions (see Sambrook, et al., ibid.).

This cDNA library was hybridized with a $^{32}$P-labeled oligonucleotide having the following sequence:

5'-CTG(A/G)GC(A/G)ATGAA(A/G)ATGGCA    (SEQ ID NO:1).

GCCAGGGC(C/T)TCATACAGGGCTGTGCC(A/G)

TCCATGTT(A/G)ATGGT(A/G)GC-3'

(This oligonucleotide was obtained commercially from Oligos, Etc., Wilsonville, Oreg.). This oligonucleotide was chosen on the basis of shared homology between a cloned rat glutamate transporter gene (GLAST1) and the bacterial glutamate transporter gene gltP (see Storck et al, ibid. and Wallace et al., ibid.), which suggested an important and conserved structural motif. Hybridization was performed at 50° C. in a solution containing 0.5M Na$_2$HPO$_4$ (pH 7.15)/ 7% sodium dodecyl sulfate (SDS) and the filters were washed at 60° C. in 2× SSPE [0.36M NaCl/20 mM sodium phosphate (pH 7.7)/2 mM ethylenediamine tetraacetic acid (EDTA)] and 1% SDS. Hybridizing clones were identified by autoradiography at −70° C. using tungsten-containing intensifying screens (DuPont-NEN, Wilmington, Del.).

More than 20 positively-hybridizing clones were detected in screening experiments using the above-described primer. One of these clones was excised from the cloning vector in vivo by superinfection with a defective filamentous phage that recognizes and excises cloned insert sequences along with adjacent modified phage replication-form sequences (termed pBluescript SK and available from Strategene). This clone contained a 2.7 kilobase (kb) insert, which was sequenced using the dideoxy-chain termination method of Sanger et al. (1977, Proc. Natl. Acad. Sci. USA 74: 5463), using Sequenase 2.0, a modified form of bacteriophage T7 DNA polymerase (U.S. Biochemical Corp., Cleveland, Ohio). The nucleotide sequence of the portion of this clone containing an open reading frame (encoding the ASCT1 gene) is shown in FIGS. 1A–1E.

This ASCT1 clone (SEQ ID No.:2) was found to be comprised of about 180 bp of 5' untranslated region, about 900 bp of 3' untranslated region and an open reading frame of 1596 bp encoding the ASCT1 transporter protein (comprising 532 amino acids). The initiator methionine codon was found to be the first methionine codon 3' to an in-frame stop codon and embedded within the consensus sequence for eukaryotic translation initiation (see Kozak, 1987, Nucleic Acids Res 15: 8125–8132). The ASCT1 amino acid sequence (SEQ ID No.:3; also shown in FIGS. 1A–1E) was found to exhibit similarity to other known glutamate transporter subtypes (an amino acid sequence comparison is shown in FIGS. 5A & 5B). An amino acid comparison between glutamate transporters from rat (GLAST1 and GLT-1) and rabbit (EAAC1) showed 39%, 34% and 39% sequence identity (respectively) between these amino acid transporter proteins (shown in FIGS. 5A & 5B by shaded boxes). This degree of sequence identity is comparable to the sequence identity between these glutamate subtypes themselves. Both the amino and carboxyl termini were found to be divergent between these transporter proteins, and diversity was also found in the extracellular domains of these putative protein sequences, which contain conserved potential N-glycosylation sites (shown in FIGS. 5A & 5B by open boxes). It was noted that a highly conserved sequence (comprising the amino acids —LYEA—) in the glutamate transporters was replaced by the unrelated amino acid sequence —IFQC— in the ASCT1 sequence (at positions 385–387 of the ASCT1 amino acid sequence shown in FIGS. 5A & 5B). 6–10 putative transmembrane domains were found using the algorithm of Eisenberg et al. (1984, J. Molec. Biol. 179: 125–142). On the basis of these data ASCT1 was determined to encode a related but distinct and novel member of the amino acid transporter family.

EXAMPLE 2

Isolation of Human Excitatory Amino Acid Transporter cDNA

The remaining (>20) positively-hybridizing clones from the human motor cortex cDNA library detected by hybridization with the primer described in Example 1 (SEQ ID No.:1) were isolated and the corresponding plamids obtained by in vivo excision after superinfection with defective phage as described in Example 1 above. These resulting plasmids were isolated and purified using conventional techniques (see Sambrook et al., ibid.). Four classes of clones were distinguished based on differential hybridization experiments using each clone as a hybridization probe against a panel of the remaining clones one after another, where conditions of hybridization stringency were varied to distinguish between each of the classes.

Representative clones from each class were sequenced as described in Example 1. One class of clones represented the ASCT1 cDNA sequences described in Example 1. The other three classes were found to encode novel proteins having amino acid sequences homologous to but distinct from the human ASCT1 sequence. Clone GT5 was determined to contain a 4.0 kb insert encoding a protein having a predicted amino acid sequence (termed EAAT1; SEQ ID No.:4) homologous to but distinct from the rat GLAST1 cDNA clone of Storck et al. (ibid.). Clone GT13 was determined to contain a 2.5 kb insert comprising an open reading frame corresponding to a full-length coding sequence for a novel human transporter gene termed EAAT2 (SEQ ID No.:6). Clone GT11 was found to contain a partial sequence of another novel human transporter termed EAAT3. The EAAT3 clone was used to re-screen the cDNA library described in Example 1. The result of these re-screening experiments was the isolation of Clone GT11B containing a full-length open reading frame encoding EAAT3 (SEQ ID No.:8).

FIGS. 11A & 11B shows the results of alignment of the predicted amino acid sequences of the three novel glutamate transporters of the invention. Nine regions of Eisenberg algorithm predicted hydrophobicity are denoted by overlining, and potential sites of N-linked glycosylation (consensus sequence N-X-S/T, where X is any amino acid) are indicated by the circles asparagine (N) residues. EAAT1 shares 47% (253/542) amino acid sequence identity with EAAT2 and 46% (262/574) sequence identity with EAAT3, whereas the EAAT2 sequence is 45% (259/574) identical to the predicted EAAT3 sequence. Cross-species comparisons of the predicted amino acid sequences of these novel human glutamate transporters revealed the following relationships: EAAT1 was found to be 96% homologous with the rat GLAST1 sequence (Storck et al., ibid.); EAAT2 was found to be 90% homologous with the rat GLT1 sequence (Pines et al., 1992, ibid.); and EAAT3 was found to be 93% homologous with the rabbit EAAC1 sequence (Kanai & Hediger, 1992, ibid.). These results indicate that EAAT1, EAAT2 and EAAT3 are related but distinct members of the glutamate transporter family of amino acid transporters.

EXAMPLE 3

Functional Expression of the ASCT1 Amino Acid Transporter Gene in Xenogus Oocytes The sequence similarity between ASCT1 and the glutamate transporters GLAST1, EAAC1 and GLT-1 suggested that the protein encoded by ASCT1 was an amino acid transporter. The ability of the ASCT1 gene product to transport amino acids, and the identity of which amino acids might be transported by this gene product, was assayed in *Xenopus laevis* oocytes following microinjection of in vitro synthesized ASCT1 RNA.

Briefly, the coding sequence of the ASCT1 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For ASCT1, the sense primer contained a KpnI recognition sequence (GGTAC↓C), and the antisense primer contained an XbaI recognition sequence (T↓CTAGA) at their respective 5' termini. Each of the PCR primers used for amplifying ASCT1 sequences had the following sequence:

```
ASCT1 sense primer:
5'-CGCGGGTACCGCCATGGAGAAGAGCAAC-3'    (SEQ ID NO:10);

ASCT1 antisense primer:
5'-CGCGTCTAGATCACAGAACCGACTCCTTG-3'   (SEQ ID NO:11).
```

PCR amplification was performed for 30 cycles, each cycle comprising 1 minute at 94° C., 30 seconds at 55° C. and 2 minutes at 72° C. Following the PCR, the product of the amplification reaction was purified using standard techniques (Saiki et al., 1988, Science 239: 487–491). The DNA then digested with the restriction enzymes KpnI and XbaI and then cloned into the polylinker of an oocyte transcription vector (POTV; see Wang el al., 1991, Nature 352: 729–731) that had been digested with KpnI and XbaI. Synthetic RNA was then transcribed in vitro from this clone using the method of Kavanaugh et al. (1992, J. Biol. Chem. 267: 22007–22009) employing bacteriophage T7 RNA polymerase (New England Biolabs, Beverly, Mass.). 20–50 nL of ASCT1 RNA (at a concentration of about 400 $\mu$g/mL) was injected into defolliculated stage V–VI Xenopus oocytes excised from female *Xenopus laevis* anesthetized by immersion in 3-aminobenzoic acid for 60 min. Excised oocytes were treated with collagenase II (Sigma Chemical Co., St. Louis, Mo.) in calcium-free Barth's saline solution [comprising 88 mM NaCl, 1 mM KCl, 2.4 mM NaHCO$_3$, 0.82 mM MgSO$_4$, 7.5 mM Tris-HCl (pH 7.6), 50 U/mL Nystatin (Sigma) and 0.1 mg/mL gentamycin (Sigma)] for 60 min., and then incubated overnight at 15° C. in 50% Leibowitz's L-15 media (Grand Island Biological Co. (GIBCO), Long Island, N.Y.). After overnight incubation the oocytes were mechanically defolliculated and then were injected with ASCT-1 RNA and incubated at 19° C. for 48 h (see Kim el al., 1991, Nature 352: 725–728 for further details of Xenopus oocyte preparation and microinjection).

Amino acid transport in such oocytes was assayed using [$^3$H] alanine, [$^3$H] serine or [$^{35}$S] cysteine (obtained from New England Nuclear, Boston, Mass.). Briefly, microinjected oocytes were patch-lamped at −60 mV using a Dagan TEV-200 clamp amplifier with an Axon Instruments (Foster City, Calif.) TL-1 A/D interface controlled by pCLAMP software (Axon Instruments) (see Kavanaugh et al., 1992, J. Biol. Chem. 267: 22007–22009 for a detailed review of this methodology) and continuously superfused with ND-96 buffer (consisting of 96 mM NaCl/2 mM KCl/1.8 mM CaCl$_2$/1 mM MgCl$_2$/5 mM HEPES, pH 7.5). For transport measurements, this solution was changed to a solution containing varying concentrations of the radiolabeled amino acids in ND-96 buffer.

Figure 6B:
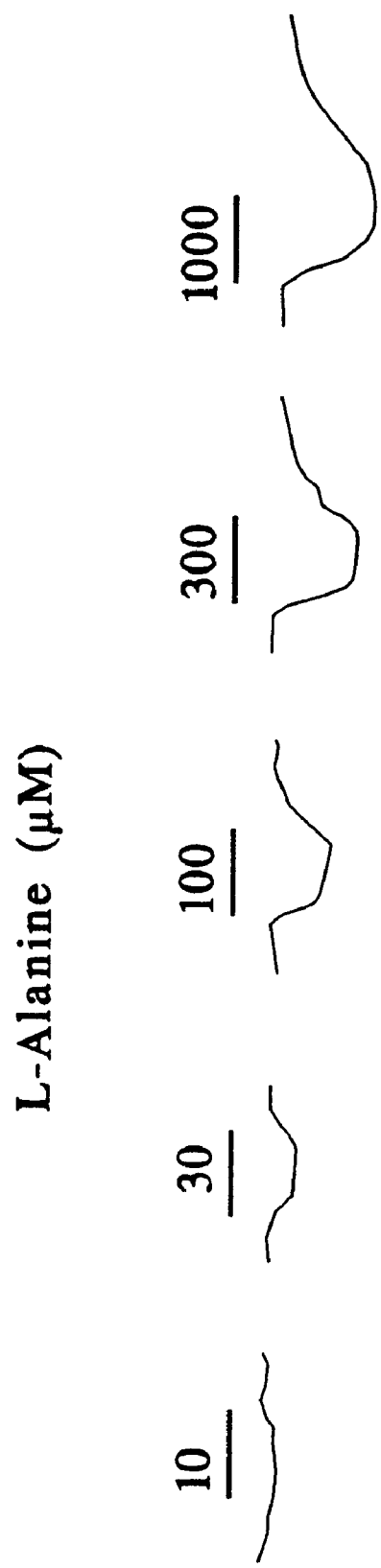
Figure 6C:
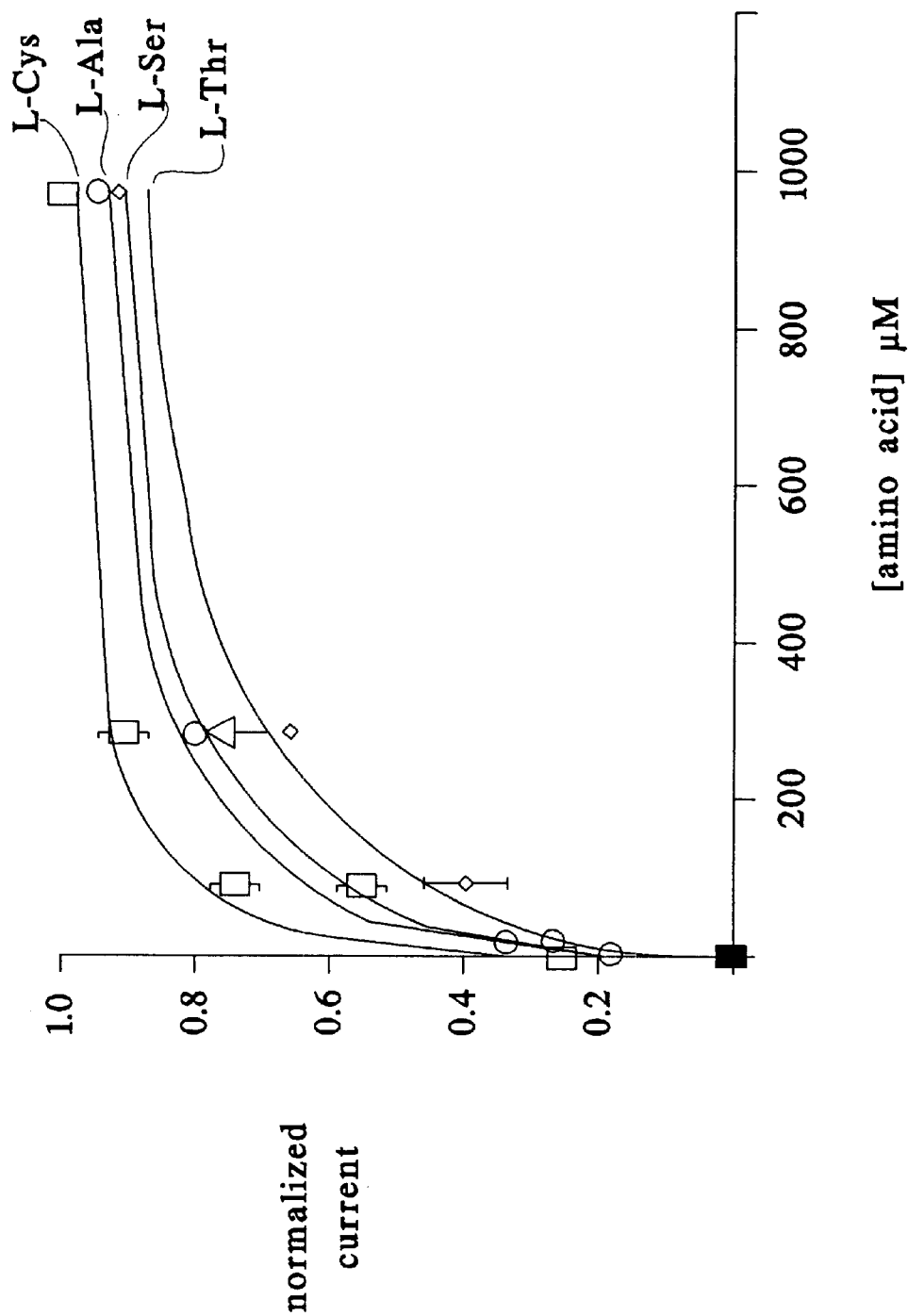

Three types of experiments were performed, the results of each being shown in FIGS. 6A–6C. As shown in FIG. 6A, when such oocytes were contacted with ND-96 buffer containing L-alanine, L-serine or L-cysteine, a hyperpolarization of the cell plasma membrane was produced as the result of inward currents of Na$^+$ ion, as has been associated with other known amino acid transporters (see Nicholls, ibid.). In contrast, the amino acids L-lysine, L-glutamine, proline, glycine, methionine, arginine, glutamate, asparagine, and leucine, and the amino acid analogues N-methylalanine, had no effect at much higher concentrations (i.e., about 1 mM). Another amino acid analogue, 2-methylaminoisobutyric acid (MAIB), which is known to be specific for the amino acid transporter type A (Christensen et al., 1967, J. Biol. Chem. 242: 5237–5246), also had no effect at concentrations of 1 mM. Further, in competition experiments, contacting such oocytes with a solution containing MAIB at a concentration of 10 mM had no effect on the rate of uptake of [$^3$H] alanine present at 100 $\mu$M. The response of the oocytes was also stereospecific (D-alanine was found to produce only 12±3% of the response produced by treatment of these oocytes with L-alanine) and Na$^+$ ion-specific (no response was detected when Na$^+$ ions were replaced by tris-hydroxyethylaminomethane buffer, shown in FIG. 6A). The rate of radiolabeled amino acid uptake (in pmol/min per oocyte, determined at an amino acid concentration of 100 $\mu$M) for the amino acids alanine, cysteine and serine are shown in Table I.

The uptake currents measured in ASCT1-injected oocytes were found to be both dose-dependent and saturable. FIG. 6B illustrates the dose-dependency of the electrochemical response of ASCT1-injected oocytes to L-alanine. The intensity of the response (equivalent to the amount of current flow into the cell) increased with the concentration of L-alanine from 10 $\mu$M to 1 mM. The saturability of this response is shown in FIG. 6C. In this Figure, the current, normalized to the maximum response obtained with L-alanine, is shown plotted against the extracellular amino acid concentration of each amino acid tested. For the L-stereoisomers of alanine, serine, cysteine and threonine, the inward current flux was found to saturate and reach a plateau at concentrations from 400–1000 $\mu$M. More detailed analyses of ithe kinetics of amino acid influx were performed by least squares linear regression analysis of induced inward current ([I]) plotted as a function of substrate amino acid concentration ([S]), using the equation shown in the legend of Table II. Data were averaged from all oocytes tested, and the results expressed as the mean±standard error are shown in Table 11.

These results indicated that the cloned ASCT1 cDNA derived from human motor cortex mRNA encoded an amino acid transporter that was specific for Alanine, Serine, Cysteine (and Threonine) and that amino acid transport activity was accompanied by an inward current flow mediated by sodium ions. These results demonstrated that the novel amino acid transporter isolated herein was related to but distinct from other, known transporters, such as the so-called ASC amino acid transporters (Christensen ei al., ibid.).

EXAMPLE 4

Functional Expression of the Glutamate Amino Acid Transporter Genes in Xenogus Oocytes Similar series of experiments were performed using RNA synthesized in vitro from constructs containing each of the cloned glutamine transporter genes of the invention. In these experiments, each of the PCR primers used to amplify each of the glutamate transporter genes had the following sequence:

EAAT1 sense primer:

5'-CGCGGGTACCAATATGACTAAAAGCAATG-3'  (SEQ ID NO: 12);

EAAT1 antisense primer:

5'-CGCGTCTAGACTACATCTTGGTTTCACTG-3'  (SEQ ID NO: 13);

EAAT2 sense primer:

5'-CGCGGGTACCACCATGGCATCTACGGAAG-3'  (SEQ ID NO: 14);

EAAT2 antisense-primer:

5'-CGCGTCTAGATTATTTCTCACGTTTCCAAG-3'  (SEQ ID NO: 15);

EAAT3 sense primer:

5'-CGCGGGTACCGCCATGGGGAAACCGGCG-3'  (SEQ ID NO: 16);

EAAT3 antisense primer:

5'-CGCGGGATCCCTAGAACTGTGAGGTCTG-3'  (SEQ ID NO: 17).

As can be determined by inspection of these sequences, each of the sense primers contained a KpnI recognition sequence (GGTAC↓C), and each of the antisense primers contained an XbaI recognition sequence (T↓CTAGA) at the 5' terminus of each primer for EAAT1 and EAAT2. For EAAT3, the sense primer contained a KpnI recognition sequence, and the antisense primer contained a BamHI recognition sequence (G↓GATCC) at the 5' terminus of each primer.

PCR amplification was performed for 30 cycles, each cycle comprising 1 minute at 94° C., 30 seconds at 50° C. and 2 minutes at 72° C. Following the PCR, each of the PCR products was isolated and cloned into pOTV as described in Example 3, from which RNA encoding each glutamate transporter was synthesized in vitro as described.

Figure 12A:
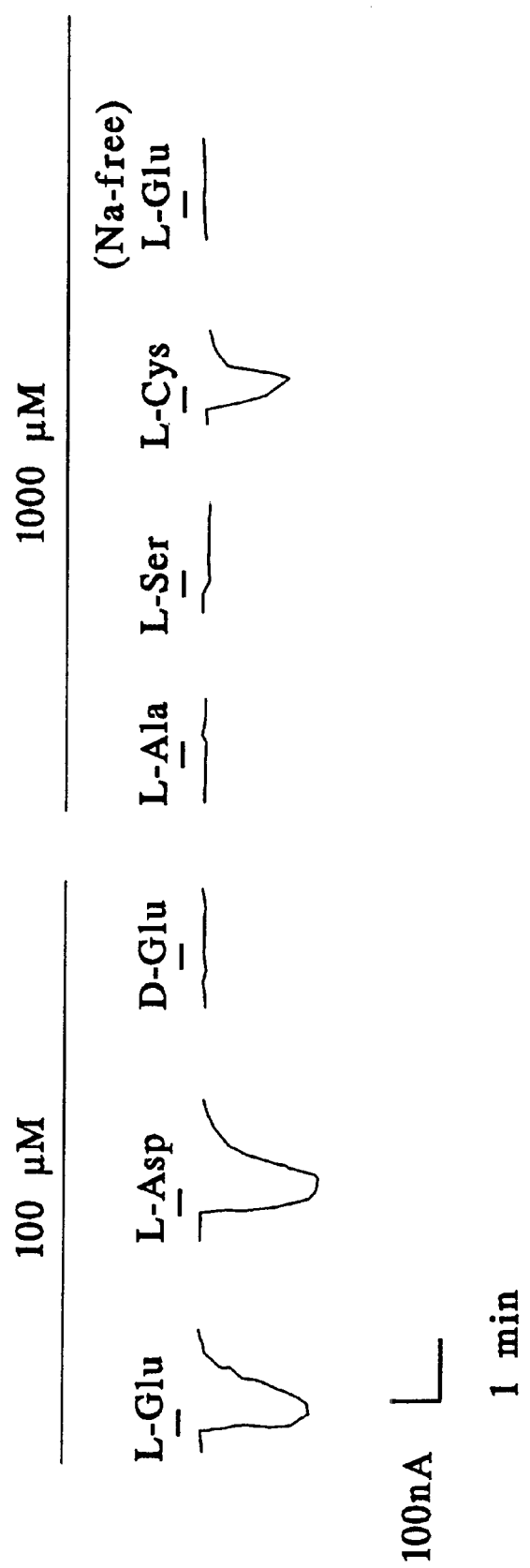
Figure 12C:
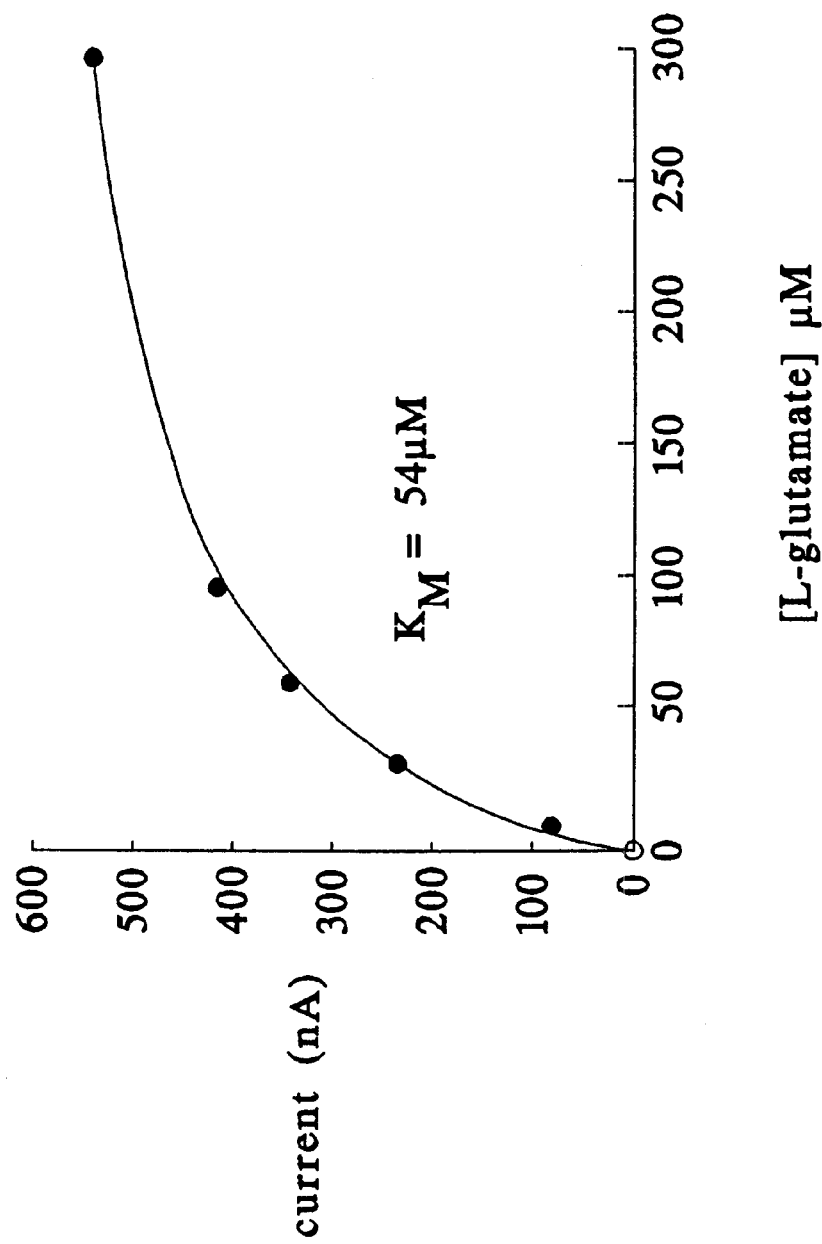

Such RNA preparations were each introduced into Xenopus oocytes as described in Example 3 to enable expression therein. Amino acid uptake experiments were performed on such oocytes expressing each of the glutamate transporters, also as described in Example 3. Results of such experiments are shown in FIGS. 12A through 12C. FIG. 12A shows electrogenic uptake of various amino acids in EAAT1-expressing oocytes. Both L-glutamate and L-aspartate caused inward currents as high as several microamps when added to the incubation media (ND-96) at a concentration of 100 $\mu$M. In contrast, incubation of EAAT1-expressing oocytes with L-alanine and L-serine at ten-fold higher concentrations (i.e., 1000 $\mu$M) did not result in electrogenic uptake of these amino acids. Uptake was found to be stereospecific, since L-glutamate incubation did not result in the generation of an inward electric current, and sodium-ion specific, since electrogenic uptake of L-glutamate was abolished by incubation in sodium ion-free media (choline was used to replace sodium in these incubations).

These experiments also demonstrated the surprising result that cysteine, when present at high enough extracellular concentrations (i.e., 1000 $\mu$M) was capable of being electrogenically transported by the EAAT1 transporter. Cysteine had not previously been reported to be a glutamate transporter substrate; however, amino acid sequence analysis of the EAAT1 transporter showed structural similarities between EAAT1 and the ASCT1 transporter, which was demonstrated herein to transport cysteine (see Example 3). As will be discussed in detail below, the EAAT1 transporter displays a $K_m$ for glutamate of 54 $\mu$M; in contrast, the $K_m$ for cysteine was found to be 300 $\mu$M. The EAAT1 transporter thus displays a pattern of substrate specificity that is distinct from that of any known glutamate transporter.

FIGS. 12B and 12C illustrate the results of biochemical analysis of substrate affinity of the EAAT1 transporter for glutamate, said results being plotted as current versus substrate concentration to yield an estimate of the $K_m$. These experiments were performed essentially as described for the ASCT1 transporter in Example 3. Patch-lamped oocytes expressing the EAAT1 transporter were incubated with varying extracellular concentrations of L-glutamate, and the magnitude of the resulting inward currents determined. From these experiments, the plotted relationship between the magnitude of the inward current and the extracellular L-glutamate concentration was determined, resulting in an estimate for $K_m$ equal to 54 $\mu$M for L-glutamate. These results were in good agreement with results obtained in COS-7 cells expressing the EAAT1 transporter, described hereinbelow (see Example 5).

EXAMPLE 5

Functional Expression of the Amino Acid Transporter Genes in COS-7 Cells

DNA fragments comprising the coding sequences of the novel glutamate transporter genes of the invention were excised from the POTV constructs described in Example 3 and subcloned into the mammalian expression plasmid pCMV5 (Anderson et al., 1989, J. Biol. Chem. 264: 8222–8229). These mammalian expression constructs were used for transient expression assays of glutamate transporter protein function after transfection of each of these constructs into COS-7 cells (Gluzman, 1981, Cell 23: 175–182).

Each of the pCMV5 constructs corresponding to EAAT1, EAAT2 and EAAT3 were introduced into COS-7 cells by DEAE-dextran facilitated transfection (see Sambrook et al., ibid.). Two day following transfection, the transfected cells were washed three times in phosphate-buffered saline (PBS) and then incubated with a mixture of radiolabeled amino acid ([$^3$H]-L-glutamate or [$^3$H]-D-aspartate; Dupont-NEN) and non-radiolabeled amino acid for 10 min. After incubation, the cells were washed three times with ice-cold PBS, solubilized with a solution of 0.1% sodium dodecyl sulfate (SDS) and the amount of radioactivity associated with the cells determined using standard liquid scintillation counting methods. The results of these experiments showed that cells transfected with each of the glutamate transporter constructs accumulated significantly-higher (between 10- and 100-fold higher) amounts of radioactivity than did mock (i.e., pCMV5 plasmid) transfected COS-7 cells (which accumulation represented endogenous COS-7 cell uptake of radioactive glutamate). The course of radioactive glutamate uptake was found to be linear for at least 20 min in assays performed at room temperature.

Figure 7A:
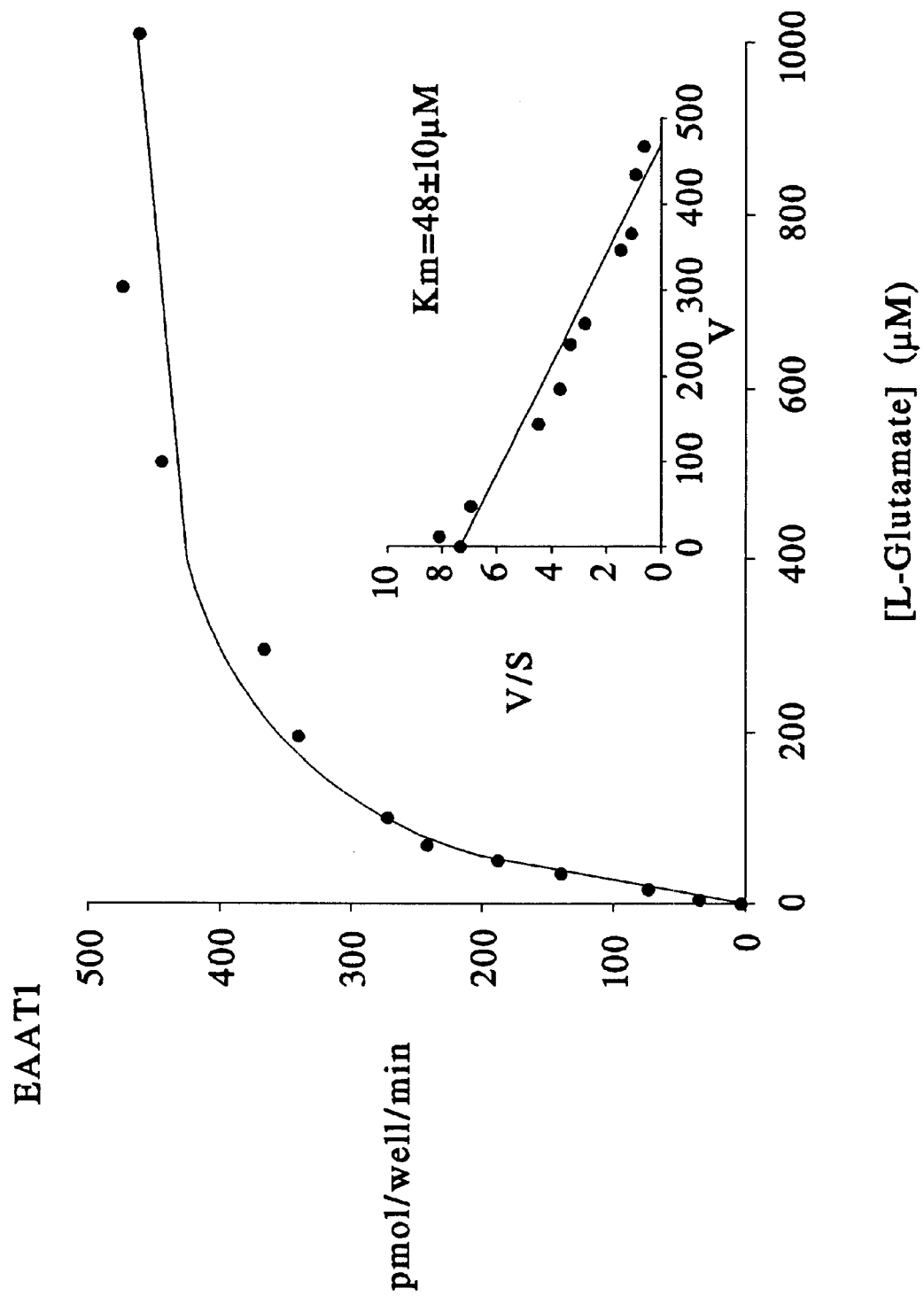
FIGS. 7A–7F presents glutamate transporter kinetics of EAAT1 (FIG. 7A & B), EAAT2 (FIG. 7C & D) and EAAT3 (FIG. 7E & 7F).
Figure 7B:
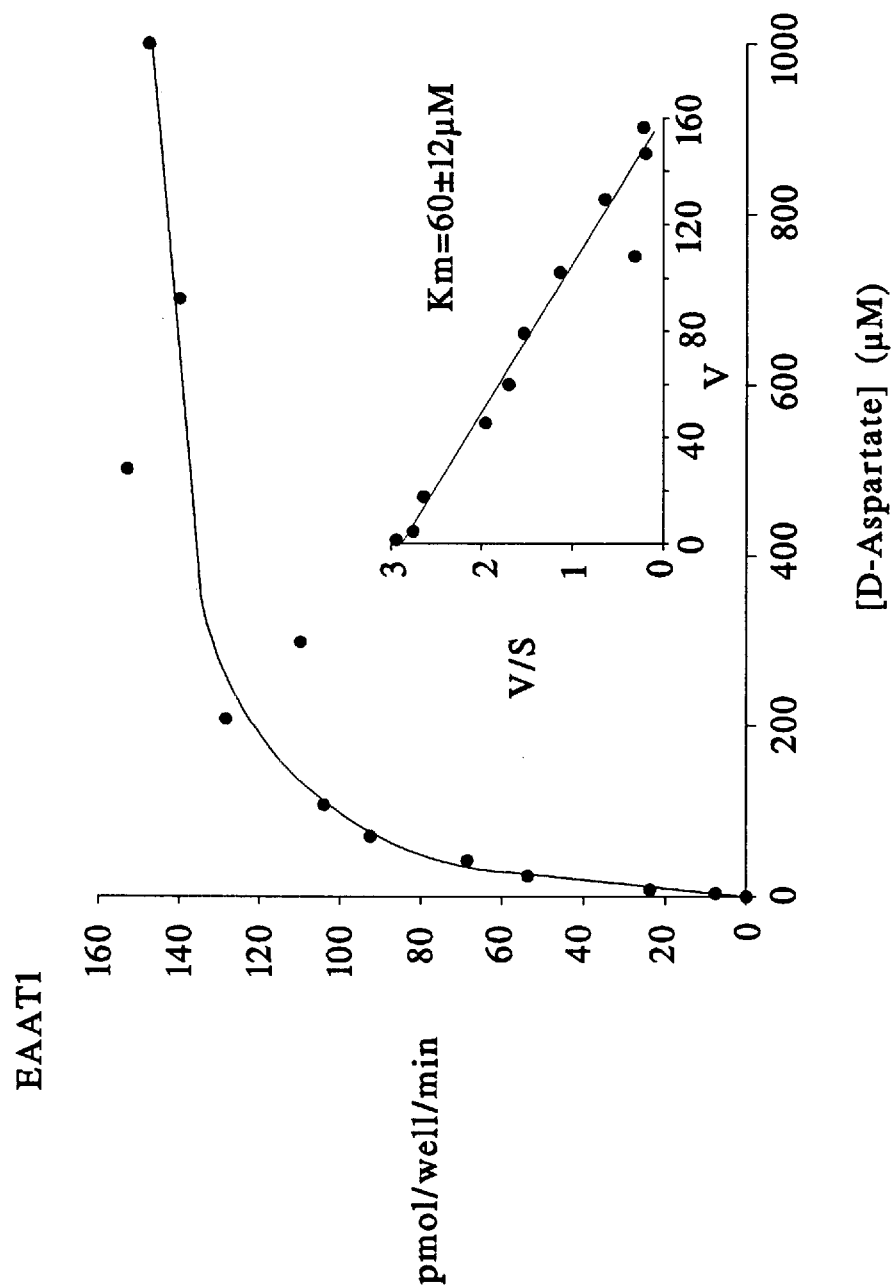
Figure 7C:
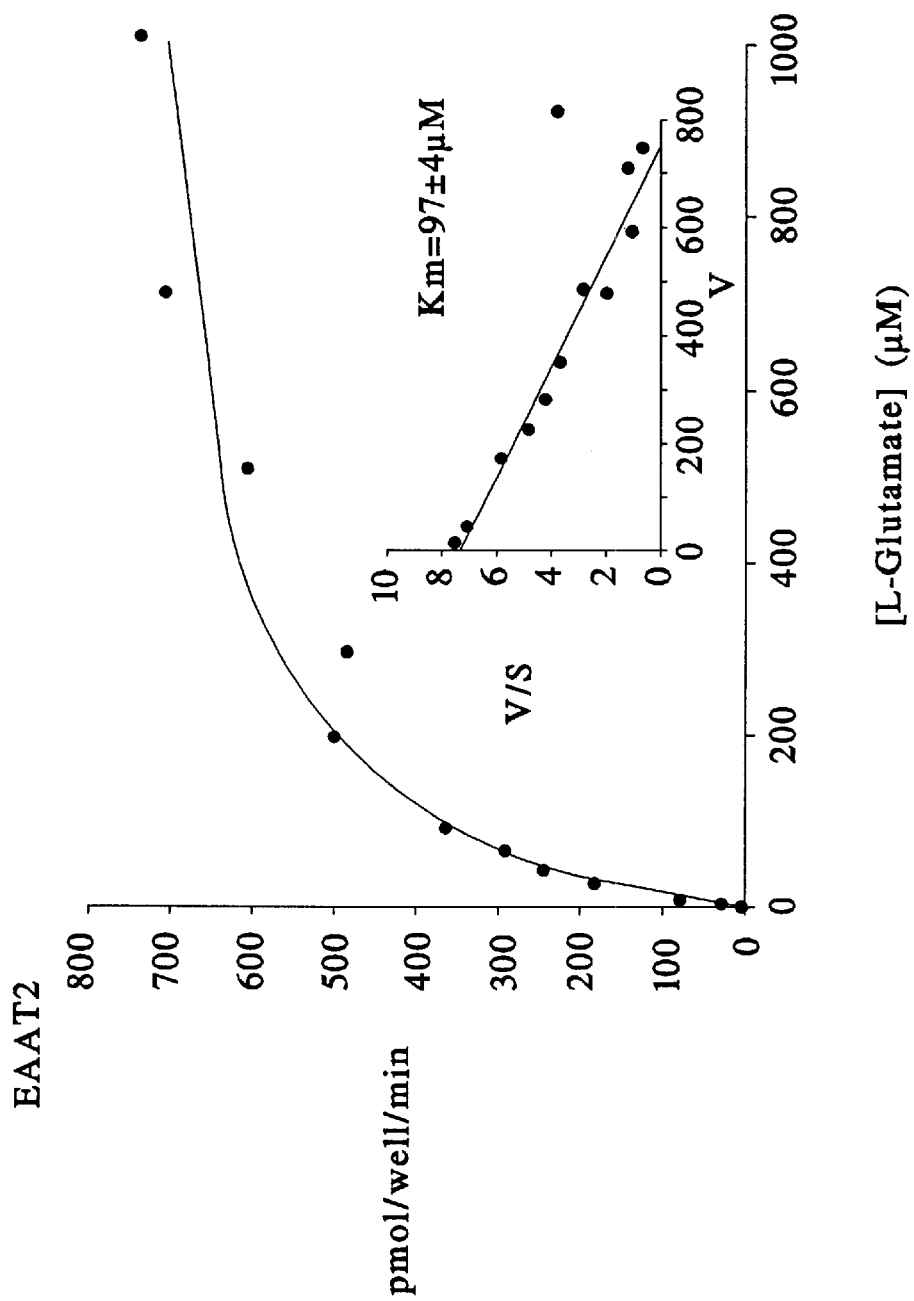
Figure 7D:
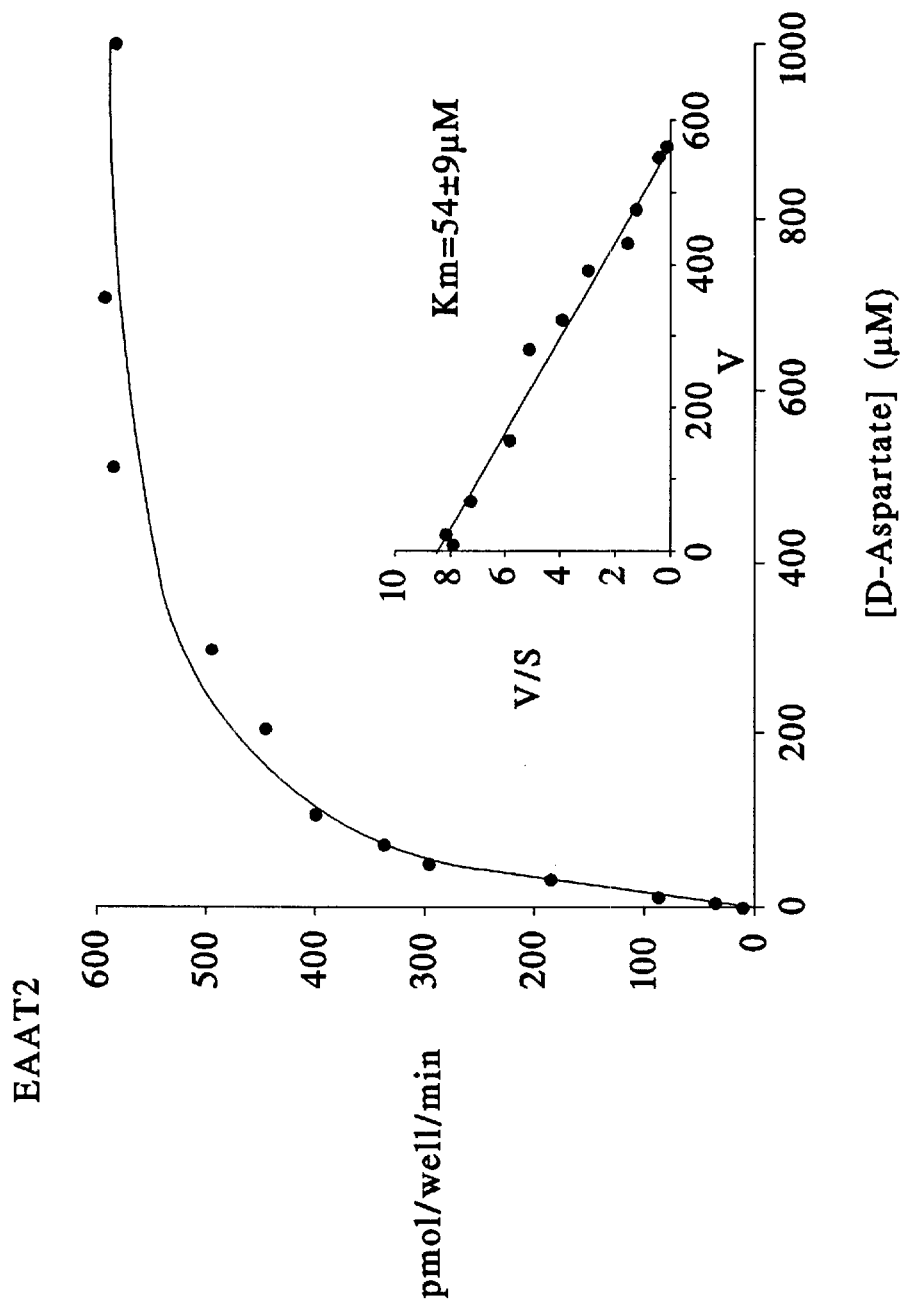
Figure 7E:
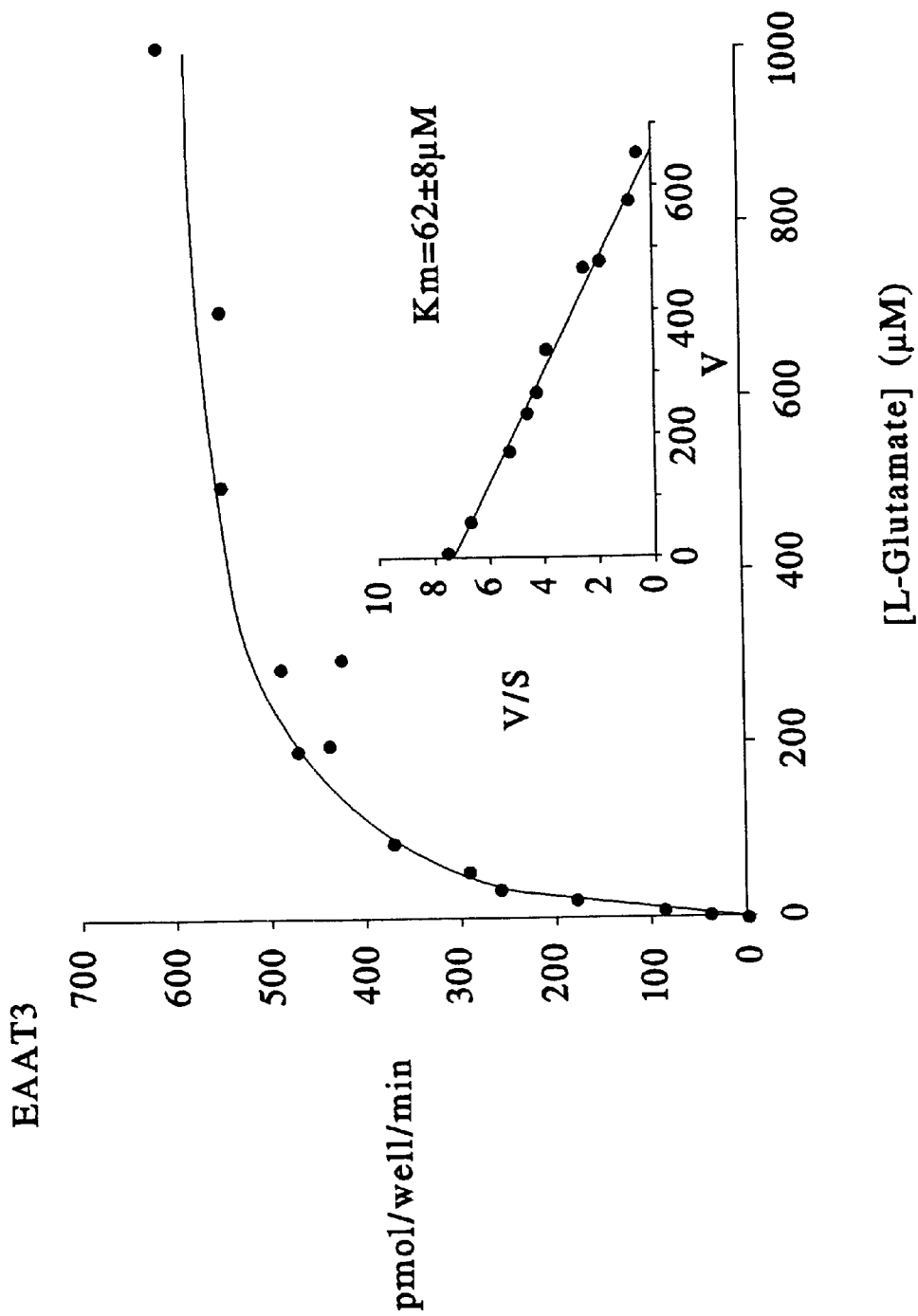
Figure 7F:
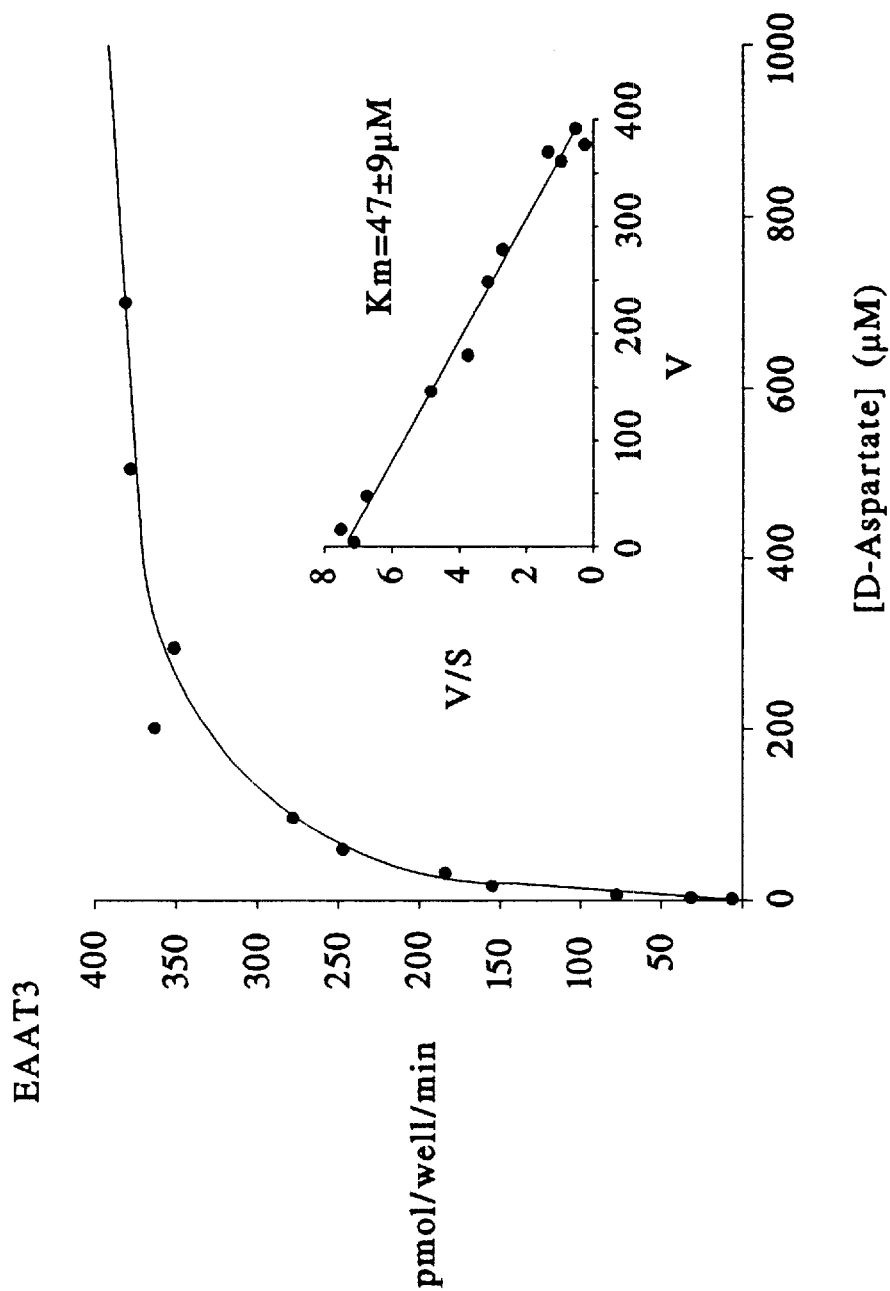

These results are shown in FIGS. 7A–7F. In the Figure, EAAT1 transporter kinetics of glutamate uptake are depicted in FIG. 7A and of aspartate are shown in FIG. 7B. Similarly, EAAT2 kinetics for glutamate and aspartate are shown in FIGS. 7C & 7D, respectively. Finally, EAAT3 kinetics are shown in FIG. 7E (glutamate) and FIG. 7F (aspartate). Each data point was determined by incubating a COS cell culture transfected with the appropriate pCMV5-glutamate transporter clone with 100 nM of radiolabeled amino acid and increasing amounts of unlabeled amino acid. Results are plotted as uptake velocity (in pmol/cell culture/min) minus endogenous uptake versus total amino acid concentration, and each data point was performed in triplicate. The results show that both glutamate and aspartate uptake mediated by each of the three novel human glutamate transporters is saturable. Insets in each Panel depict Eadie-Hofstee plots of initial velocity data, from which $K_m$ values were determined. The $K_m$ values are shown as the mean±standard error based on at least three independent experiments. These results show that each of the three novel transporter proteins comprising the instant invention is functionally competent as an amino acid transporter when expresed in a culture of mammalian cells, and that each of the novel transporters encoded by the cDNA clones EAAT1, EAAT2 and EAAT3 displays a collection of biochemical properties consistent with their designation as human glutamate transporter proteins.

EXAMPLE 6

Inhibitor Potency Analyses Using COS-7 Cells Expressing Amino Acid Transporter Proteins COS-7 cell cultures transformed with pCMVS-human glutamate transporter constructs as described in Example 4 were used to characterize the pharmacological properties of each of these transporter proteins relative to a variety of known glutamate transporter inhibitors. These assays were performed essentially as described in Example 4, with the exception that varying amounts of each of a number of known inhibitor compounds were included in the incubations.

Figure 8B:
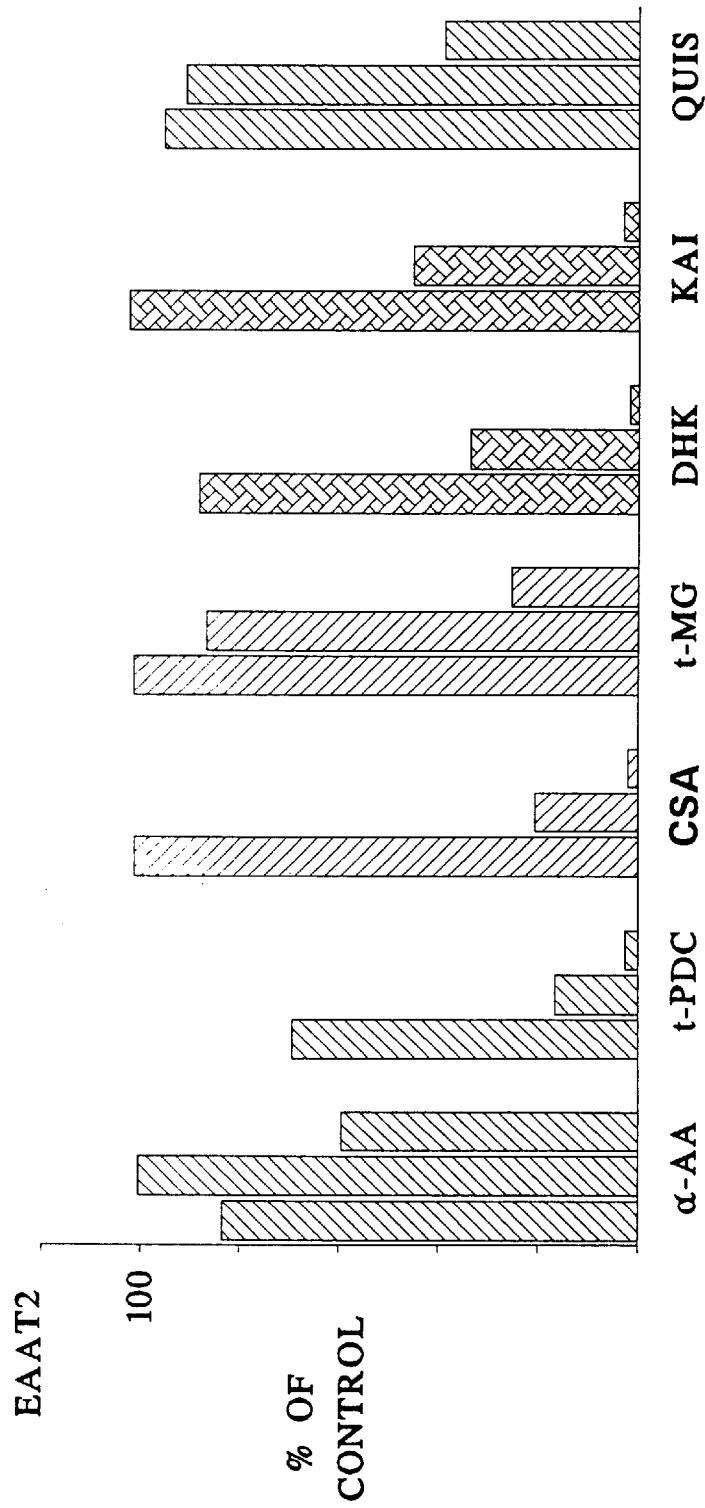
Figure 8C:
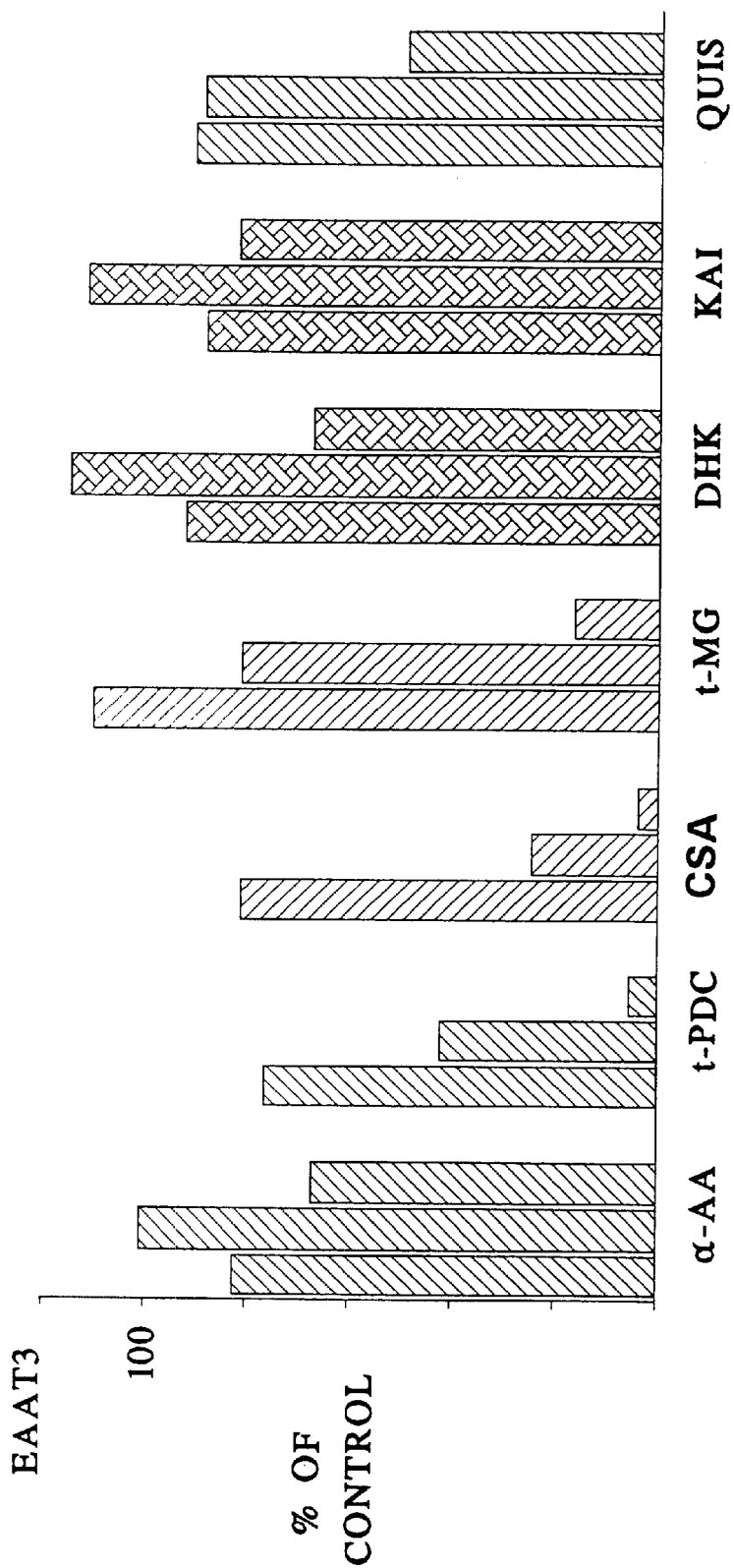

The results of these experiments are shown in FIGS. 8A–8C. The data in FIGS. 8A–8C represent the pharmacological responsiveness of glutamate transport by the human excitatory amino acid transporters EAAT1, EAAT2 and EAAT3 when contacted with the following competitors/inhibitors: L-threo-β-hydroxyaspartate (THA); L-trans-pyrrolidine-2,4-dicarboxylate (PDC); L-serine-O-sulfate (SOS); dihydrokainate (DHK); and kainate (KAI). In these experiments, uptake of 1 μM of [$^3$]-L-glutamate was determined in the presence of the indicated amounts of each of the inhibitors. As can be seen from the Figures, each of the glutamate transporter proteins of the invention displays a characteristic pattern of sensitivity to the inhibitors. Thus, the relative potency of inhibition of radiolabeled glutamate uptake was found to be as follows for the EAAT1 and EAAT3 transporter proteins:

THA<PDC<SOS<<DHK, KAI, whereas the inhibition pattern for EAAT2 was as follows:

PDC<TRA<DHK<KAI<SOS.

These results, as well as results obtained from similar experiments performed with L-cysteate, L-cysteine sulfinic acid, β-glutamate and L-aspartate-β-hydroxymate, are shown in Table III. Even though the relative pattern of inhibition was the same for EAAT1 and EAAT3, the results shown in the Table support the fining that each of the glutamate transporters of the invention is uniquely characterized by its sensitivity to this panel of glutamate uptake inhibitors.

In addition, a number of reported inhibitors were found to be ineffective when tested with COS cell culture expressing each of the novel glutamate transporter proteins of the invention. These include cis-1-aminocyclobutane-1,3-dicarboxylate, L-pyroglutamicacid, S-sulfo-L-cysteine, N-acetyl aspartylglutamate, N-methyl-D-aspartate (NMDA) and quisqualate. α-aminoadipate, a classical inhibitor of glutamate uptake, exhibited only low potency when tested against all three EAAT subtypes. These results of functional assays support the conclusion arrived at from structural analysis (i.e., nucleic acid and amino acid sequence analyses) that the glutamate transporter cDNAs and proteins of the invention are novel mammalian transporter species.

EXAMPLE 7

Tissue Distribution of Amino Acid Transporter Expression

The tissue distribution of mRNA corresponding to expression of the amino acid transporters disclosed herein was determined in various tissues by Northern hybridization experiments (see Sambrook et al., ibid.). The results of these experiments are shown in FIGS. 9 and 10.

A panel of tissue samples was examined by Northern hybridization analysis performed under high stringency conditions as follows. A nylon filter containing 2 μg human peripheral tissue poly(A)$^+$ RNA was obtained from Clonetech Laboratories (Palo Alto, Calif.), and a similar filter was prepared containing human brain region RNA as follows. Total RNA was isolated from human brain region tissue obtained from the Oregon Brain Repository and 20 μg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with $^{32}$P-labeled amino acid transporter-specific probes for each transporter to be analyzed. Probes were derived from amino acid transporter coding sequences and labeled using $^{32}$P-labeled dCTP by the random primer method (Boehringer-Mannheim, Indianapolis Ind.). Filters were hybridized overnight at 42° C. individually with each radiolabeled probe (at a concentration of 10$^6$ cpm/mL) in a solution of 5× SSPE/50% formamide/7.5× Denhardt's solution (comprising 0.15 g/100 mL each of Ficoll, polyvinylpyrrolidone and bovine serum albumin)/2% SDS and 100 μg/mL denatured salmon-sperm DNA. Following hybridization, filters were washed twice for 30 min at room temperature in 2× SSPE/0.1% SDS and twice for 20 min at 50° C. in 0.1× SSPE/0.1 % SDS. Hybridizing RNAs were visualized by autoradiography at −70° C. using intensifying screens. The filters were subsequently re-probed as described with a radiolabeled human β-actin probe (Clonetech) as a positive control.

Figure 9:
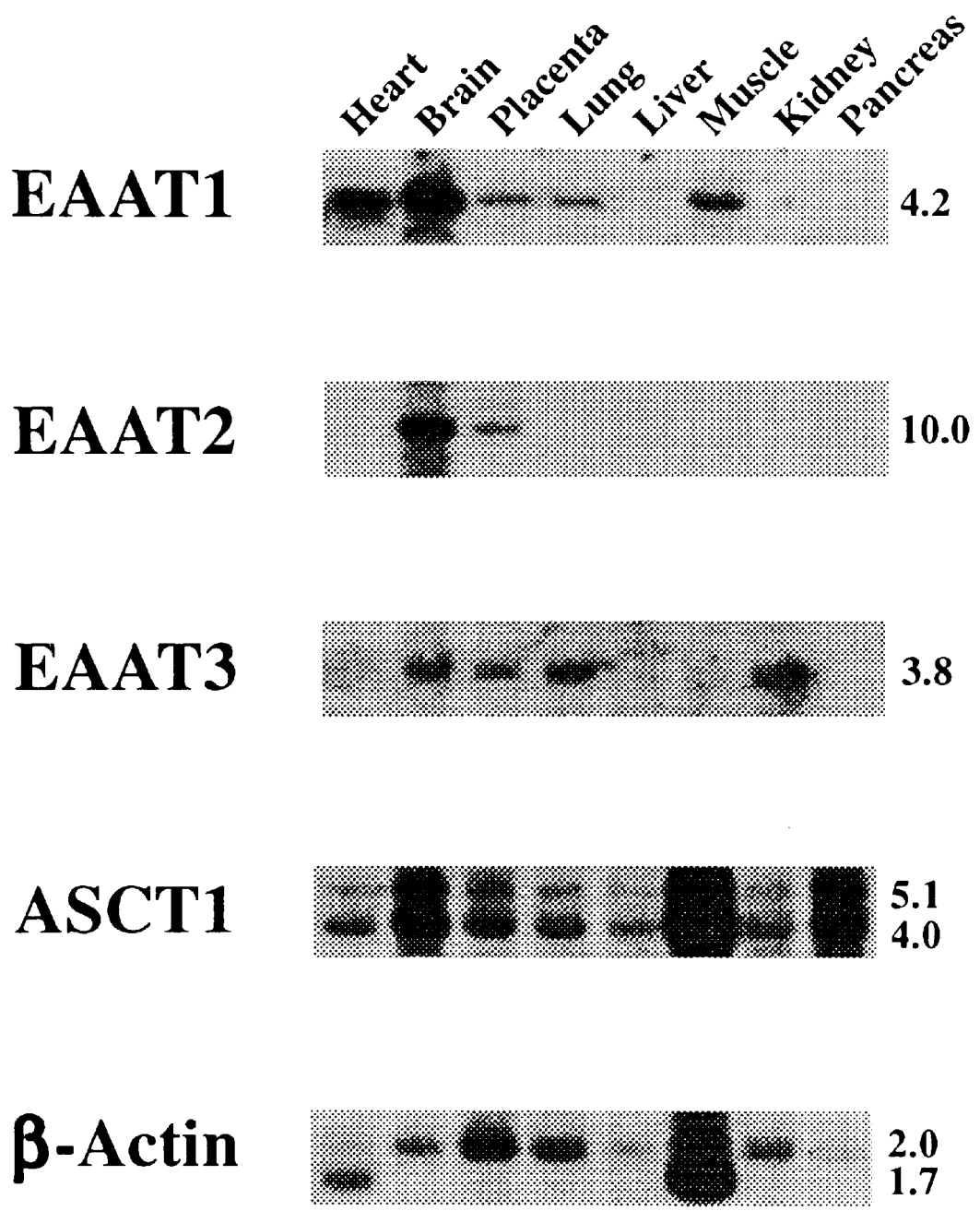
FIG. 9 shows the pattern of expression of EAAT1, EAAT2, EAAT3 and ASCT1 in human tissues; $\beta$-actin is shown as a control for amount of RNA in each lane.
Figure 10:
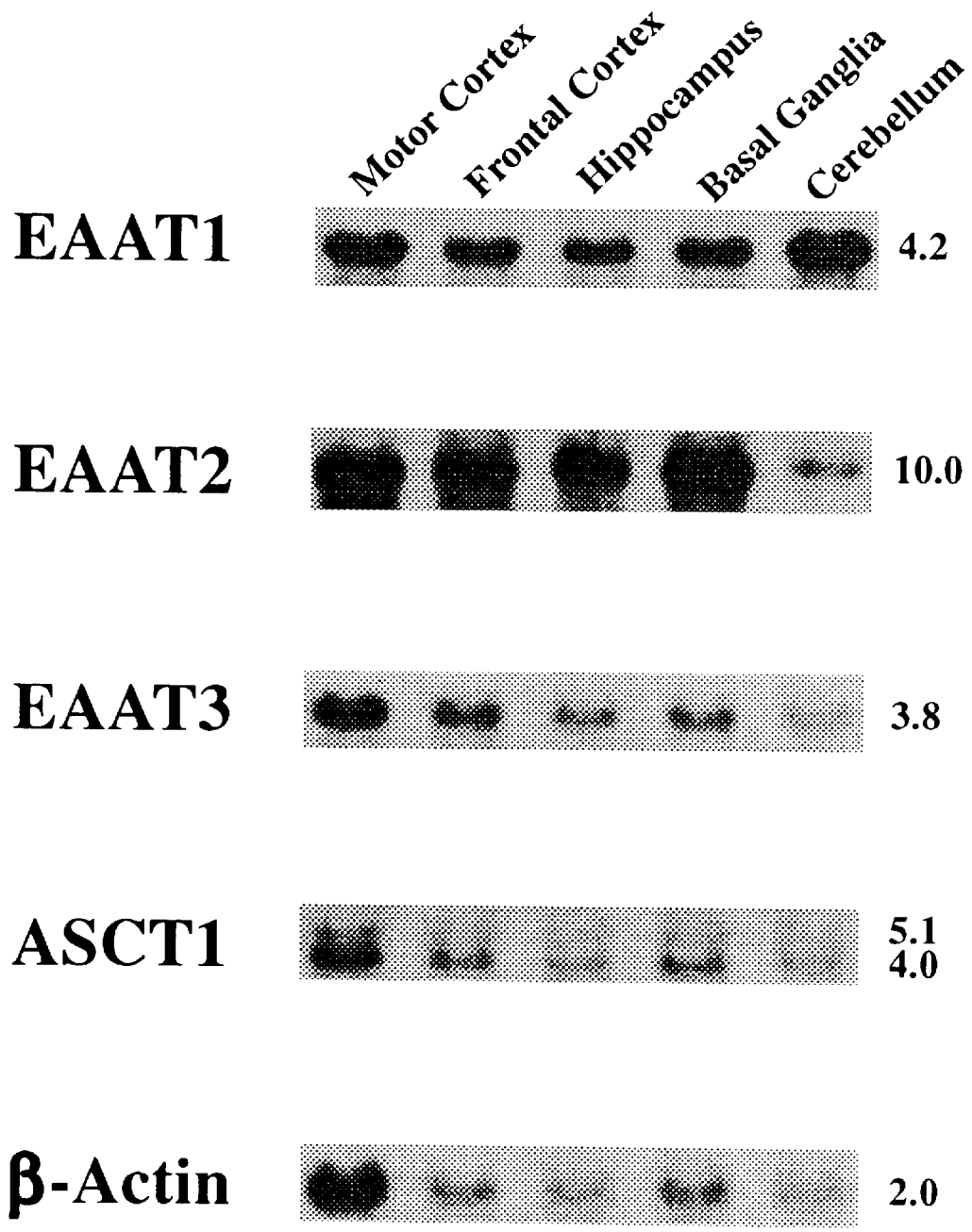
FIG. 10 shows the pattern of expression of EAAT1, EAAT2, EAAT3 and ASCT1 in human brain tissue; $\beta$-actin is shown as a control for the amount of RNA in each lane.

The results of these experiments are shown in FIGS. 9 and 10. FIG. 9 illustrates expression of each of the amino acid transporters in human heart, brain, placenta, lung, liver, muscle, kidney and pancreas. The size (in kb) of the transcripts corresponding to expression of each transporter are displayed along the right-hand border of each panel. As is seen from these autoradiographs, EAAT1 is expressed predominantly in brain, heart and muscle, to a lesser extent in placenta and lung, weakly in liver, and at levels below the ability of this assay to detect in kidney and the pancreas (if at all). EAAT2 is expressed in brain, and to a lesser extent in placenta; expression was not detected in any other tissue tested. EAAT3 is expressed predominantly in the kidney, but significant expression was also detected in brain, placenta, and lung. ASCT1 is expressed in all tissues tested as at least one of three differently-sized transcripts, possibly corresponding to differential RNA processing during expression of this transporter (which result might be due in the alternative to the utilization of alternative polyadenylation sites found in the 3' untranslated region). These results demonstrate that the amino acid transporters disclosed herein are encoded by separate and distinct, albeit related, genes and that each transporter has a unique pattern of tissue-specific expression.

FIG. 10 shows the distribution of these amino acid transporter transcripts in different human brain regions. Varying expression levels were found for each of the amino acid transporters in all brain regions examined. These results support the conclusion that the amino acid transporters of the invention may play an important role in normal brain function, and that disruption of amino acid transport by these transporter may be important determinants in organic brain dysfunction, as a result of ischemia or anoxia.

EXAMPLE 8

Construction of Vaccinia Virus-Recombinant Expression Constructs for Functional Expression of Amino Acid Transporters Using an alternative approach, the amino acid transporter proteins of the invention are expressed in human HeLa (vulval adenocarcinoma) cells via a vaccinia virus-based construct. In these experiments, each of the amino acid transporter cDNAs of the invention are excised from their respective pOTV-containing constructs and subcloned into a modified pBluescript (Strategene) vector wherein each of the amino acid transporter cDNAs described above is under the control of a bacteriophage T7 RNA polymerase promoter (as is described in Blakely et al., 1991, Anal. Biochem. 194: 302–308), termed pT7-AAT constructs. HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with each of the amino acid transporter constructs described above (i.e. the pT7-AAT constructs) using a lipofectin-mediated (Bethesda Research Labs, Gaithersburg, Md.) transfection protocol (see Felgner et al., 1987, Proc. Natl. Acad. Sci. USA 84: 7413–7417). Cells are then incubated for 12–24 h before being assayed for amino acid transporter expression as described in Example 5.

EXAMPLE 9

Construction of Fusion Proteins-Recombinant Expression Constructs for Expression of Immunologically-Active Epitopes of Amino Acid Transporters The amino acid transporter proteins of the invention are expressed as fusion proteins in bacteria to produce immunologically-active epitopes. In these experiments, each of the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNAs are translationally in-frame with sequences encoding glutathione-S-transferase (described in Arriza et al., 1992, J. Neurosci. 12: 4045–4055), termed PGST-AAT constructs. After introduction of the PGST-AAT constructs into bacterial cells (E. coli, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against each of the amino acid transporters of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual*, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

| Amino Acid (1 mM)* | ASCT1 RNA-injected Oocytes** | Water-injected Oocytes** |
| --- | --- | --- |
| Alanine | 18 ± 2 | 0.6 ± 0.1 |
| Serine | 20 ± 5.1 | 0.4 ± 0.1 |
| Cysteine | 19.2 ± 5.9 | 1.0 ± 0.3 |

*n = 5;
**pmol/min per oocyte:

TABLE II

| Amino Acid* | $K_m$ (μM) | $I_{max}$** |
| --- | --- | --- |
| Alanine | 71 ± 14 | (1.0) |
| Serine | 88 ± 11 | 1.2 ± 0.08 |
| Cysteine | 29 ± 6 | 1.0 ± 0.04 |
| Threonine | 137 ± 19 | 1.4 ± 0.03 |
| Valine | 390 ± 8 | 0.6 ± 0.11 |

NOTE:
data is expressed as the mean of at least 5 determinations ± standard error.
*All amino acids were the L-stereoisomer
**$I_{max}$ was determined by least squares fit to the equation:

$$I = I_{max} \times ([S]/(K_m + [S]))$$

where $I_{max}$ is the maximal current and $K_m$ is the transport constant

TABLE III

Glutamate uptake inhibition constants.

Ki (in μM) determined for each transporter[a]

| Compound | EAAT1 | EAAT2 | EAAT3 |
|---|---|---|---|
| THA (L-threo-β-hydroxyaspartate) | 32 ± 8 | 19 ± 6 | 25 ± 5 |
| PDC (L-trans-pyrrolidine-2,4-dicarboxylate) | 79 ± 7 | 8 ± 2 | 61 ± 14 |
| SOS (L-Serine-O-sulfate) | 107 ± 8 | 1157 ± 275 | 150 ± 52 |
| DHK (Dihydrokainate) | >1 mM | 23 ± 6 | >1 mM |

TABLE III-continued

Glutamate uptake inhibition constants.

Ki (in μM) determined for each transporter[a]

| Compound | EAAT1 | EAAT2 | EAAT3 |
|---|---|---|---|
| KAI (Kainate) | >1 mM | 59 ± 18 | >1 mM |
| L-cysteate | 10 ± 3 | 10 ± 2 | 19 ± 9 |
| L-cysteine sulfinic acid | 14 ± 7 | 6 ± 1 | 17 ± 2 |
| β-glutamate | 297 ± 118 | 156 ± 37 | 307 ± 48 |
| L-aspartate-β-hydroxymate | 369 ± 70 | 184 ± 27 | 133 ± 34 |

[a]Under the assay conditions used ([S] << Km). the Ki value does not differ significantly from the measured IC50.

What is claimed is:

1. An isolated 62.1 kilodalton human excitatory amino acid transporter produced by expressing in a cell a recombinant expression vector encoding human EAAT2.

2. The human excitatory amino acid transporter of claim 1 having an amino acid sequence identified as SEQ ID No.:7.

3. A cell membrane preparation comprising a 62.1 kilodalton human excitatory amino acid transporter that is EAAT2, produced by a cell that expresses a recombinant expression vector encoding human EAAT2.

4. The cell membrane preparation of claim 3, wherein the human excitatory amino acid transporter has an amino acid sequence identified as SEQ ID No.: 7.

* * * * *